US007828948B1

(12) United States Patent
Hatch et al.

(10) Patent No.: US 7,828,948 B1
(45) Date of Patent: Nov. 9, 2010

(54) PRECONCENTRATION AND SEPARATION OF ANALYTES IN MICROCHANNELS

(75) Inventors: Anson Hatch, Tracy, CA (US); Anup K. Singh, Danville, CA (US); Amy E. Herr, Fremont, CA (US); Daniel J. Throckmorton, Tracy, CA (US)

(73) Assignee: Sandia Corporation, Livermore, CA (US)

( * ) Notice: Subject to any disclaimer, the term of this patent is extended or adjusted under 35 U.S.C. 154(b) by 935 days.

(21) Appl. No.: 11/536,753

(22) Filed: Sep. 29, 2006

Related U.S. Application Data

(60) Provisional application No. 60/725,015, filed on Oct. 6, 2005.

(51) Int. Cl.
*B01D 57/02* (2006.01)
*B01D 61/58* (2006.01)
*B01D 63/00* (2006.01)
(52) U.S. Cl. .................. 204/455; 204/605
(58) Field of Classification Search ........... 204/451, 204/455, 601, 605
See application file for complete search history.

(56) References Cited

U.S. PATENT DOCUMENTS

| 6,007,690 | A | * | 12/1999 | Nelson et al. .............. 204/601 |
| 6,235,471 | B1 | * | 5/2001 | Knapp et al. ................ 435/6 |
| 6,319,469 | B1 | * | 11/2001 | Mian et al. ................. 422/64 |
| 2001/0044108 | A1 | | 11/2001 | Shih | |
| 2003/0116437 | A1 | * | 6/2003 | Burns et al. ................ 204/453 |
| 2004/0084370 | A1 | | 5/2004 | Singh | |

2004/0112751 A1 6/2004 Han

OTHER PUBLICATIONS

F. Helfferich; "Ligand Exchange. II. Separation of Ligands Having Different Coordinative Valences", Journal of the American Chemical Society, 1962. vol. 84, pp. 3242-3245.
Martin M. Chui; Ronald J. Phillips; Michael J. McCarthy; "Measurement of the Porous Microstructure of Hydrogels by Nuclear Magnetic Resonance", Journal of Colloid and Interface Science, 1995, vol. 174, pp. 336-344.
Daniel Figeys: Normal J. Dovichi; "Multiple separations of DNA sequencing fragments with a non-cross-linked polyacrylamide-filled capillary: capillary electrophoresis at 300 V/cm". Journal of Chromatography A, 1995, vol. 717, pp, 113-116.
A. S. Rathore: Cs. Horvath; "Axial Nonuniformities and Flow in Columns for Capillary Electrochromalography", Analytical Chemistry, 1998, vol. 70, pp. 3069-3077.
Julia Khandurina: Stephen C. Jacobson; Larry C. Waters; Robert S. Foote; J. Michael Ramsey; "Microfabricated Porous Membrane Structure for Sample Concentration and Electrophoretic Analysis", Analytical Chemistry. 1999, vol. 71, pp. 1815-1819.

(Continued)

*Primary Examiner*—Nam X Nguyen
*Assistant Examiner*—J. Christopher Ball
(74) *Attorney, Agent, or Firm*—Smith, Gambrell & Russell, LLP

(57) ABSTRACT

Disclosed herein are methods and devices for preconcentrating and separating analytes such as proteins and polynucleotides in microchannels. As disclosed, at least one size-exclusion polymeric element is adjacent to processing area or an assay area in a microchannel which may be porous polymeric element. The size-exclusion polymeric element may be used to manipulate, e.g. concentrate, analytes in a sample prior to assaying in the assay area.

21 Claims, 26 Drawing Sheets

OTHER PUBLICATIONS

David J. Beebe; Jeffrey S. Moore; Qing Yu; Robin H. Liu; Mary L. Kraft; Byung-Ho Jo; Chelladurai Devadoss; "Microfluidic tectonics; A comprehensive construction platform for microfluidic systems", Proceedings of the National Academy of Sciences, 2000, vol. 97, No. 25, pp. 13488-13493.

Yinglie Liu; Robert S. Foote; Stephen C. Jacobson; Roswitha S. Ramsey; J. Michael Ramsey; "Electrophoretic Separation of Proteins on a Microchip with Noncovalent, Postcolumn Labeling", Analytical Chemistry. 2000, vol. 72, No. 19, pp. 4608-4613.

Kelly Swinney; Darryl J. Bornhop; "Detection in capillary electrophoresis", Electrophoresis, 2000. vol. 21, pp. 1239-1250.

Sundaresh N. Brahmasandra; Victor M. Ugaz; David T. Burke; Carlos H. Mastrangelo; Mark A. Burns; "Electrophoresis, in microfabricated devices using photopolymerized polyacrylamide gels and electrode-defined sample injection", Electrophoresis, 2001, vol. 22, pp. 300-311.

Catherine R. Cabrera; Paul Yager; "Continuous concentration of bacteria in a microfluidic flow cell using electrokinetic techniques", Electrophoresis, 2001, vol. 22. pp. 255-362.

Lian Ji Jin; Braden C. Giordano; James P. Landers; "Dynamic Labeling during Capillary or Microchip Electrophoresis for Laser-Induced Fluorescence Detection of Protein-SDS Complexes without Pre- or Postcolumn Labeling", Analytical Chemistry, 2001, vol. 73, pp. 4994-4999.

Cong Yu; Mark H. Davey; Frantisek Svec; Jean M. J. Frechet; "Monolithic Porous Polymer for On-Chip Solid-Phase Extraction and Preconcentration Prepared by Photoinitiated in Situ Polymerization within a Microfluidic Device", Analytical Chemistry, 2001, vol. 73, pp. 5088-5096.

Tiemin Huang; Janusz Pawliszyn; "Microfabrication of a tapered channel for isoelectric focusing with thermally generated pH gradient", Electrophoresis, 2002, vol. 23, pp. 3504-3510.

Abebaw Belay Jemere; Richard D. Oleschuk; Fahima Ouchen; Festus Fajuyigbe; D. Jed Harrison;, "An integrated solid-phase extraction system for sub-picomolar detection", Electropheresis, 2002, vol. 23, pp. 3537-3544.

Darwin R. Reyes; Dimitri Iossifidis; Pierre-Alanin Auroux; Andreas Manz; "Micro Total Analysis Sytems. 1. Introduction, Theory, and Technology", Analytical Chemistry, 2002, vol. 74, pp. 2623-2636.

Pierre-Alain Auroux; Dimitri Iossifidis; Darwin R. Reyes; Andreas Manz; "Micro Total Analysis Systems. 2. Analytical Standard Operations and Applications", Analytical Chemistry, 2002, vol. 74, pp. 2637-2652.

Daniel J. Throckmorton; Timothy J. Shepodd; Anup K. Singh; "Electrochromatogrphy in Microchips: Reversed-Phase Separation of Peptides and Amino Acids Using Photopatterned Rigid Polymer Monoliths", Analytical Chemistry, 2002, vol. 74, pp. 784-789.

Ann Wainwright; Stephen J. Williams; Gary Ciambrone; Qifeng Xue; Jing Wei; Dennis Harris; "Sample pre-concentration by isotachophoresis in microfluidic devices", Journal of Chromatography A, 2002, vol. 979, pp. 69-80.

Olga Bilenko; Dmitri Gavrilov; Boris Gorbovitski; Vera Gorfinkel; Michael Gouzman; Georgy Guokov; Vyacheslav Khozikov; Olga Khozikov; Olga Kosobokova; Nadia Lifshitz; Serge Luryi; Andrew Stepoukhovitch; Marina Tcherevishinick; Georgy Tyshko; "Formation of a resistive region at the anode end in DNA capillary electrophoresis", Electrophoresis, 2003, vol. 24, pp. 1176-1183.

B. Scott Broyles; Stephen C. Jacobson; J. Michael Ramsey; "Sample Filtration, Concentration, and Separation Integrated on Microfluidic Devices", Analytical Chemistry, 2003, vol. 75, pp. 2761-2767.

Yan Li; Donald L. DeVoe; Cheng S. Lee; "Dynamic analyte introduction and focusing in plastic microfluidic devices for proteomin analysis", Electrophoresis, 2003, vol. 24, pp. 193-199.

Jongyoon Han; Anup K. Singh; "Rapid protein separations in ultra-short microchannels: microchip sodium dodecyl sulfate-polyacrylamide gel electrophoresis and isoelectric focusing", Journal of Chromatography A, 2004, vol. 1049, pp. 205-209.

Amy E. Herr; Anup K. Singh; "Photopolymerized Cross-Linked Polyacrylamide Gels for On-Chip Protein Sizing", Analytical Chemistry, 2004, vol. 76, pp. 4727-4733.

Jaisree Moorthy; Glennys A. Mensing; Dongshin Kim; Swomitra Mohanty; David T. Eddington; William H. Tepp; Eric A. Johnson; David J. Beebe; "Microfluidic tectonics platform: A colorimetric, disposable botulinum toxin enzyme-linked immunosorbent assay system", Electrophoresis, 2004, vol. 25, pp. 1705-1713.

Karel Kleparnik; Pavel Mikuska; "A continous-flow instrument for the determination of linear polyacrylamide stability", Electrophoresis, 2004, vol. 25, pp. 2139-2143.

Simon Song; Anup K. Singh; Timothy J. Shepodd; Brian J. Kirby; "Microchip Dialysis of Proteins Using in Situ Photopatterned Nanoporous Polymer Membranes", Analytical Chemistry, 2004, vol. 76, pp. 2367-2373.

Simon Song; Anup K. Singh; Brian J. Kirby; "Electrophoretic Concentration of Proteins at Laser-Patterned Nanoporous Membranes in Microchips", Analytical Chemistry, 2004, vol. 76, pp. 4589-4592.

Torsten Vilkner; Dirk Janasek; Andreas Manz; "Micro Total Analysis Systems. Recent Developments", Analytical Chemistry, 2004, vol. 76, pp. 3373-3386.

Robert S. Foote; Julia Khandurina; Stephen C. Jacobson; J. Michael Ramsey; "Preconcentration of Proteins on Microfluidic Devices Using Porous Silica Membranes", Analytical Chemistry, 2005, vol, 77, pp. 57-63.

Amy E. Herr; Daniel J. Throckmorton; Andrew A. Davenport; Anup K. Singh; "On-Chip Native Gel Electrophoresis-Based Immunoassays for Tetanus Antibody and Toxin", Analytical Chemistry, 2005, vol. 77, pp. 585-590.

Ronald F. Renzi; James F. Stamps; Brent A. Horn; Scott Ferko; Victoria A. Vandernoot; Jay A. A. West; Robert Crocker; Boyd Wiedenman; Daniel Yee; Julia A. Fruetel; "Hand-Held Microanalytical Instrument for Chip-Based Electrophoretic Separations of Proteins", Analytical Chemistry, 2005, vol. 77, pp. 435-441.

Ying-Chih Wang; Anna L. Stevens; Jongyoon Han; "Million-fold Preconcentration of Proteins and Peptides by Nanofluidic Filter", Analytical Chemistry, 2005, vol. 77, pp. 4293-4299.

Anson V. Hatch; Amy E. Herr; Daniel J. Throckmorton; James S. Brennan; Anup K. Singh; "Integrated Preconcentration SDS-PAGE of Proteins in Microchips Using Photopatterned Cross-Linked Polyacrylamide Gels", Analytical Chemistry, 2006, vol. 78, pp. 4976-4984.

* cited by examiner

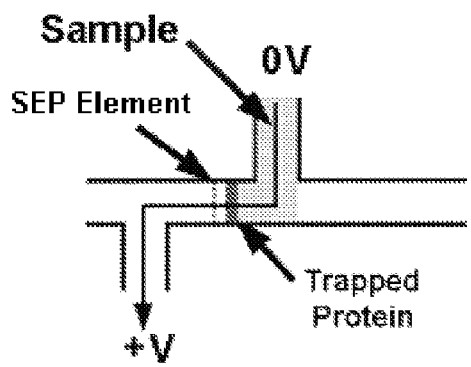
Figure 3A1
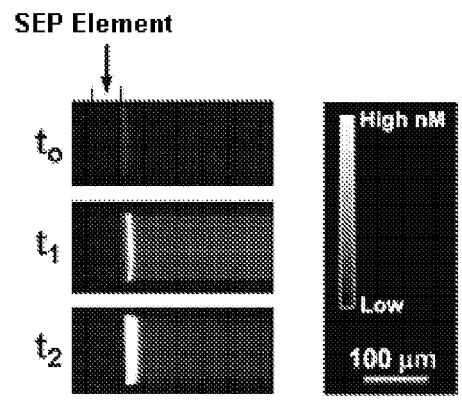
Figure 3A2
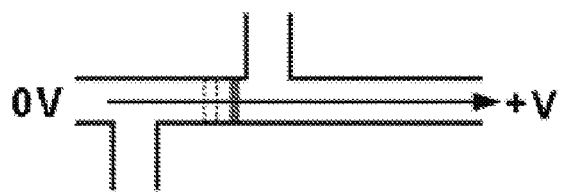
Figure 3B1
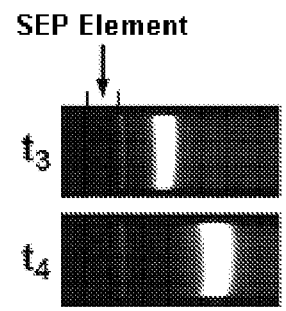
Figure 3B2
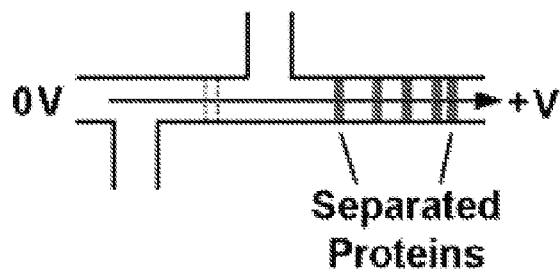
Figure 3C1
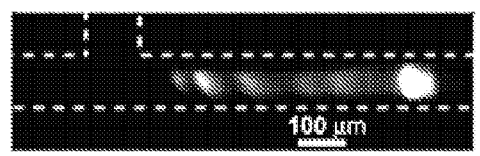
Figure 3C2

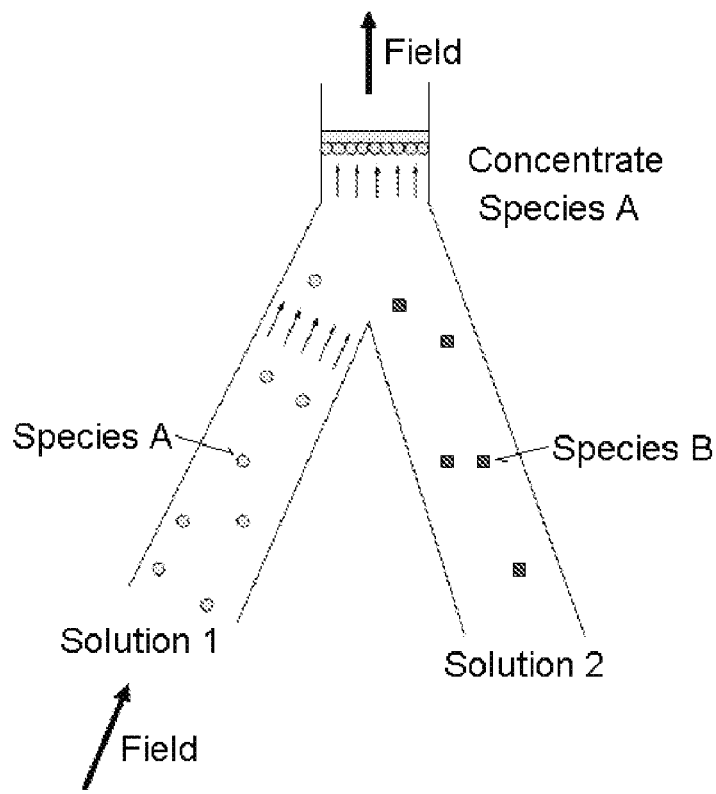
Figure 14A1
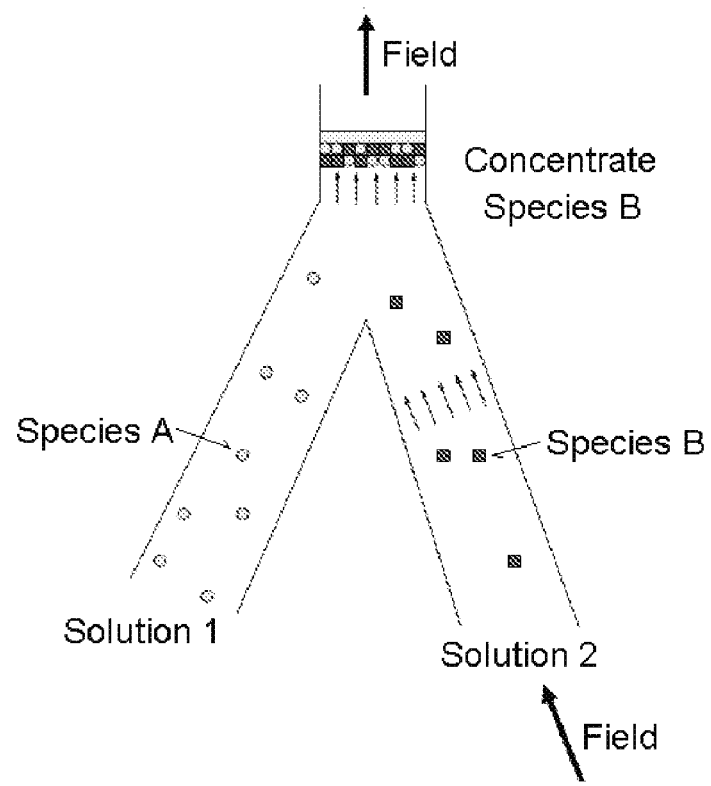
Figure 14A2

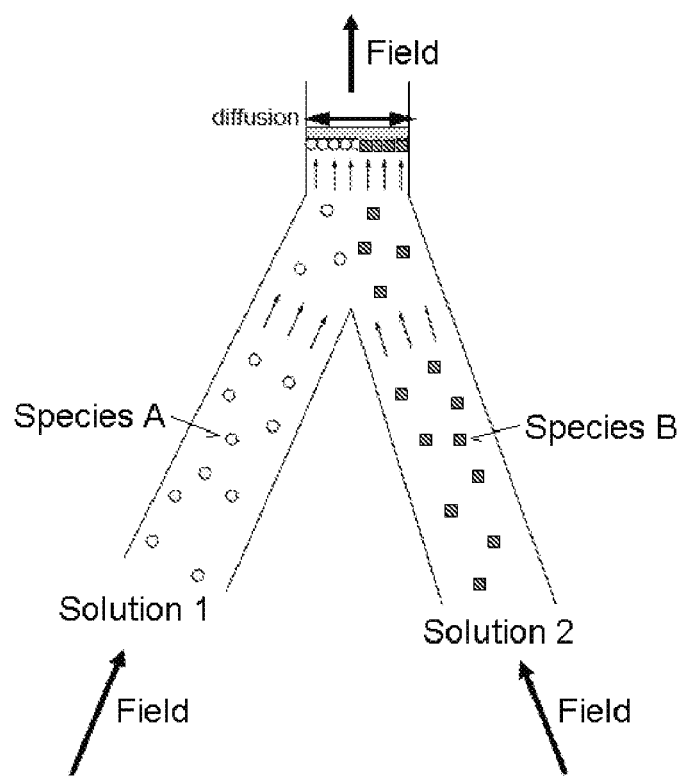
Figure 14B1
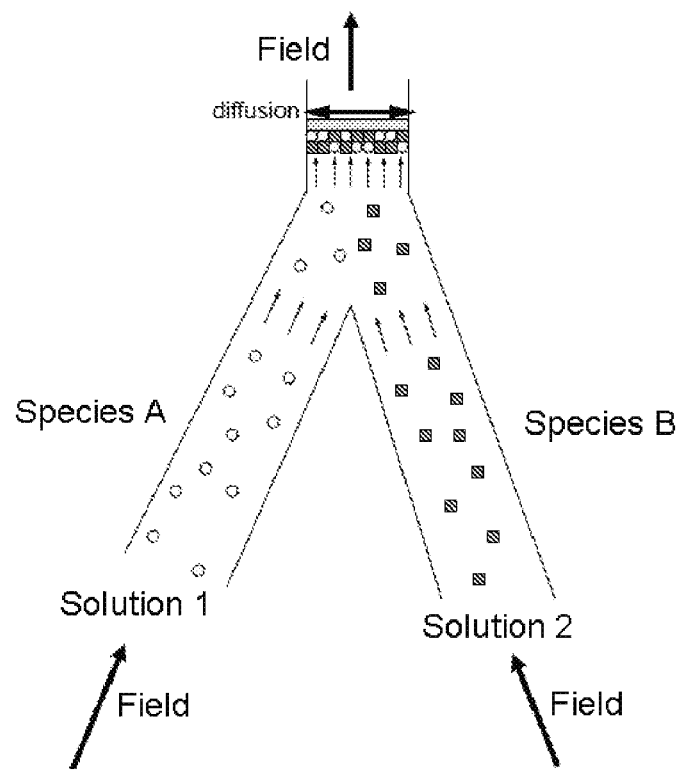
Figure 14B2

PRECONCENTRATION AND SEPARATION OF ANALYTES IN MICROCHANNELS

CROSS-REFERENCE TO RELATED APPLICATIONS

This application claims the benefit of U.S. Provisional Patent Application Ser. No. 60/725,015, filed 6 Oct. 2005, U.S. patent application Ser. No. 10/443,491 filed 22 May 2003, and U.S. patent application Ser. No. 10/646,808 filed 25 Aug. 2003, which are herein incorporated by reference in their entirety.

ACKNOWLEDGEMENT OF GOVERNMENT SUPPORT

This invention was made with Government support under government contract DE-AC04-94AL85000 awarded by the U.S. Department of Energy to Sandia Corporation. The Government has certain rights in the invention.

BACKGROUND OF THE INVENTION

1. Field of the Invention

The present invention generally relates to multidimensional electrophoresis devices and methods of making and using thereof.

2. Description of the Related Art

The advent of microfluidic chips has enabled miniaturization of many biochemical techniques resulting in faster and cheaper analysis using much smaller amounts of sample and reagents. Microfluidic devices have in many ways revolutionized the analytical capabilities available for chemistry, biology, and medicine. Microfluidic devices allow analysis using minute amounts of samples (crucial when analyzing body fluids or expensive drug formulations), are fast, and enable development of portable systems. One of the biggest advantages offered by microfluidic chips, analogous to microelectronics chips, is the potential for seamless integration of functions at the chip-scale.

While great advances have been made in integrating some functions such as injection and analysis; in most cases sample pretreatment is performed off-chip. Recently, approaches have been developed to incorporate functions such as sample cleanup, sample concentration, mixing, and reaction prior to analysis in microchips. See Auroux et al. (2002) Anal. Chem. 74:2637; Reyes et al. (2002) Anal. Chem. 74:2623; and Vilkner et al. (2004) Anal. Chem. 76:3373.

There are a number of reasons why sample concentration prior to analysis is a crucial step in development of multi-functional integrated microfluidic devices. For example, preconcentration of sample enables detection of trace or low-abundant species. This is of particular importance in many fields including clinical diagnostics, proteomics, forensics, environmental monitoring and biodefense applications. Also, micrometer dimensions of the fluidic channels lead to poorer sensitivities for optical detection than their conventional scale counterparts. Preconcentration not only improves detection sensitivity but also improves the reliability of analysis by significantly increasing signal-to-noise ratios. Further, the practical constraints on sample loading limit the minimum volume of sample inserted into a chip to the order of about 1 μl while the volume typically analyzed is on the order of about 1 nl. Hence, analytes in a sample can be concentrated up to 1000-fold without requiring additional sample.

Reported sample preconcentration methods can be categorized into many groups including surface-binding, electrokinetic equilibrium, and porous membrane techniques. Surface-binding techniques such as solid phase extraction or affinity columns use sample adsorption to surfaces for concentration and a solvent or surface property change for elution. See Broyles et al. (2003) Anal. Chem. 75:2761; Jemere et al. (2002) J. Electrophoresis 23:3537; and Yu et al. (2001) Anal. Chem. 73:5088. Electrokinetic equilibrium techniques concentrate sample by bringing species transport to a local equilibrium state electrokinetically and examples include isoelectric focusing (IEF) and field amplified sample stacking (FASS) or isotachophoresis (ITP). See Li et al. (2003) J. Electrophoresis 24:193; Cabrera & Yager (2002) J. Electrophoresis 22:355; Huang & Pawliszyn (2002) J. Electrophoresis 23:3504; and Wainright et al. (2002) J. Chromatography A 69:979.

Approaches have also been developed that rely on the concept of size-based exclusion to concentrate macromolecules using a porous membrane that excludes species of interest from the membrane pores. See Foote et al. (2005) Anal Chem. 77:57; Song et al. (2004) Anal Chem. 76:4589; Khandurina et al. (1999) Anal. Chem. 71:1815; and U.S. Publication No. 20040084370. Each of these approaches has its own advantages and drawbacks. For example, sample stacking methods require insertion and maintenance of multiple buffer zones and can be difficult to implement with samples of unknown conductivity. Affinity-based preconcentration requires a change in buffer conditions for elution. A size-exclusion or filtration-based approach is arguably the easiest to implement as it avoids complications of specifically arranging zones of buffer and reagents or the need for selective binding and release of analytes while offering high sample capacities with concentration factors greater than 1,000-fold.

However, a size-exclusion or filtration-based approach requires placement of nanoporous membranes or filters inside specific channels. Khandurina et al. demonstrated a size-exclusion approach for concentrating DNA and more recently for concentrating proteins, wherein a silicate membrane was deposited between the glass cover plate and silicon substrate of a microchip. See Khandurina et al. (1999) Anal. Chem. 71:1815. While a 600-fold signal increase was reported for proteins electrophoretically driven against the silicate membrane, the authors reported that (1) the chips are hard to fabricate in a reproducible manner, and (2) the silicate membrane often has defects adversely affecting the concentration. The requirement on fabrication is that channels bridged by the silicate membrane must be etched such that their edges are separated by a few microns. This required precision can be a demanding and limiting fabrication requirement, especially when etching deep channels with an isotropic etch process. Another limitation is that the surface area of the membrane face is a very thin line of contact between the channel lid and the top of the channel wall. The maximum flux and trapping area are dependent on the surface area of the face.

Recently, Wang et al. reported a novel preconcentrator approach with up to million-fold concentration of proteins and peptides using a nanofluidic filter that requires fabrication of micro- and nano-channels in the same chip. See Wang et al. (2005) Anal. Chem. 77:4293-4299. The nanofluidic filter described by Wang et al. requires labor intensive and demanding fabrication process to make the nanometer size channels. There are other aspects of the nanofilter that pose difficulties for integrated processing and analysis. For example, the trapping mechanism relies not on size-exclusion to trap species, but on generating an ion depletion zone that begins trapping all charged species. This means there is no option for size-selective trapping or filtering and that small buffer ions are stacked along with larger analyte which can be detrimental for downstream processing, analysis or both, e.g. if the concentrated species were directed into a gel electrophoresis channel, sample destacking would prohibit useful separations.

Further, non-linear concentration factors and lack of reproducibility are problematic with a membrane based approach to preconcentration. See Foote et al. (2005) Anal. Chem. 77:57. This behavior results from concentration polarization that can lead to sample destacking. In the pores of a size-exclusion membrane the thickness of the electrical double layer (EDL) can be on the same order of magnitude as the pore radius. For a negatively-charged membrane such as glass or (and to a lesser degree) polyacrylamide, this results in selective enrichment of cations in the pores. In the absence of an applied electric field, a boundary potential (Donnan potential) exists between bulk and the membrane to equalize the concentrations of ions. When an applied electric field is superimposed, concentration polarization results where concentrations of ions increases on the cathodic side and decreases on the anodic side. The steep concentration gradients in the depleted concentration polarization zone results in diffusion-limited transport of ions. This leads to a drop in current as a function of time upon application of the external electric field. At the diffusion limit, the current reaches a steady value referred to as "limiting current". Localized increase in ion concentrations lead to sample destacking and other non-linear effects resulting in band-broadening and irreproducible migration over time.

Thus, a need exists for methods and devices for preconcentrating a sample on a microchip that are readily and easily fabricated, produce consistent results and do not suffer from concentration polarization problems.

SUMMARY OF THE INVENTION

The present invention provides methods and devices for concentrating and then assaying an analyte in a sample on or in the same device.

In some embodiments, the present invention provides a microfluidic channel comprising at least one in situ polymerized size-exclusion polymeric element adjacent to at least one processing area. The microchannel may comprise two or more size-exclusion polymeric elements, preferably in situ polymerized. In some embodiments, the first size-exclusion polymeric element has pores that are larger than the pores of a second size-exclusion polymeric element, etc. In some embodiments, the first size-exclusion polymeric element has a cross-sectional area that is greater than the cross-sectional area of a second size-exclusion polymeric element. In some embodiments, the size-exclusion polymeric elements are arranged in series. In some embodiments, the processing area is a section of the microfluidic channel, preferably where at least one secondary microchannel interfaces with the microfluidic channel. In some embodiments, the assay area comprises a porous polymeric element, a liquid sieving gel, or the like. In some embodiments, the microfluidic channel comprises at least one size-exclusion polymeric element in between at least one processing area and at least one assay area. In some embodiments, the microfluidic channel further comprises electrodes attached thereto to provide a mobilization field such as an electric field.

In some embodiments, the present invention provides a device which comprises a microfluidic channel comprising at least one in situ polymerized size-exclusion polymeric element adjacent to at least one processing area. The microchannel may comprise two or more size-exclusion polymeric elements, preferably in situ polymerized. In some embodiments, the first size-exclusion polymeric element has pores that are larger than the pores of a second size-exclusion polymeric element, etc. In some embodiments, the first size-exclusion polymeric element has a cross-sectional area that is greater than the cross-sectional area of a second size-exclusion polymeric element. In some embodiments, the size-exclusion polymeric elements are arranged in series. In some embodiments, the processing area is a section of the microfluidic channel, preferably where at least one secondary microchannel interfaces with the microfluidic channel. In some embodiments, the assay area comprises a porous polymeric element, a liquid sieving gel, or the like. In some embodiments, the microfluidic channel comprises at least one size-exclusion polymeric element in between at least one processing area and at least one assay area. In some embodiments, the device further comprises electrodes for applying a mobilization field such as an electric field.

In some embodiments, the present invention provides a method for assaying an analyte in a sample which comprises subjecting the sample to the microfluidic channel or device described herein to concentrate the analyte, filter the sample, exchange buffer, mix, react or bind the analyte with a reagent, or a combination thereof and then assaying the analyte in the assay area by electrophoretic separation, chromatography, electrochromatography, immunochemistry, or a combination thereof, using methods known in the art. In some embodiments, the method further comprises assaying the analyte by mass spectrometry according to methods known in the art. In some embodiments, the electrophoretic separation is capillary zone electrophoresis, capillary gel electrophoresis, native PAGE, SDS-PAGE, or a combination thereof. In some embodiments, the microfluidic channel comprises at least two size-exclusion polymeric elements. The size-exclusion polymeric elements may be the same or different. In some embodiments, the analyte is concentrated on or adjacent to the size-exclusion polymeric element by applying a mobilization field, such as an electric field. In some embodiments, the analyte is assayed by applying a mobilization field such as an electric field to separate the analyte in the assay area. In some embodiments, the analyte is detected in the assay area. In some embodiments, the assay further comprises loading the sample into a segment of the microfluidic channel that is adjacent to the size-exclusion polymeric element with a mobilization field that does not cross the size-exclusion polymeric element and wherein a mobilization field that crosses the size-exclusion polymeric element is used to concentrate the analyte on or adjacent to the size-exclusion polymeric element. In some embodiments, the assay further comprises eluting the sample from the size-exclusion polymeric element with a mobilization field that does not cross the size-exclusion polymeric element. In some embodiments, the assay further comprises eluting the sample from the size-exclusion polymeric element by applying a mobilization filed across the size-exclusion polymeric element for a given period of time and then bypassing the size-exclusion polymeric element with a second mobilization field. In some embodiments, the assay further comprises using the size-exclusion polymeric element to remove or add molecules, such as labels, reagents, compounds, biomolecules, and the like. In some embodiments, the assay further comprises enhancing a reaction between the analyte and a reagent by concentrating an amount of the analyte on or adjacent to the size-exclusion polymeric element and then adding an amount of the reagent. In preferred embodiments, the amount of the analyte and the amount of the reagent are provided in amounts which result in the optimal ratio of analyte to reagent concentration for a given reaction. Such reaction kinetics and analyte to reagent concentration ratios are known in the art. In some embodiments, additional reagents, i.e. chemicals and biomolecules, may be added.

In some embodiments, the concentration polarization effects are reduced by using a narrow, about 10 to about 50 µm, preferably about 10 to about 40 µm, more preferably about 10 to about 30 µm, size-exclusion polymeric element with respect to the field direction, using an size-exclusion polymeric element that has minimal surface charge (for example polyacrylamide/bisacrylamide, or the like) or close to net zero charge with a zwitterionic polymer (for example SPE/bisacrylamide or the like), introducing a porous polymeric element only within the assay area, generating fluid flow on one or both sides of the size-exclusion polymeric element to replenish ions, or a combination thereof.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIGS. 3A-3C schematically show the sequential preconcentration, elution and separation of proteins according to the present invention. The fluorescence micrographs show the distribution of labeled analyte, i.e. BSA (which is visible only after preconcentration) at different time-points.

FIG. 3A1 schematically shows preconcentration of analytes in a sample. During the preconcentration step, an electric field drives the transport of the protein SDS complexes toward the SEP element where they become trapped and accumulate as long as the field is applied. The fluorescence micrographs show labeled BSA accumulating at the SEP element ($t_0=0$ s, $t_1=30$ s, and $t_2=120$ s preconcentration time).

FIG. 3A2 is the fluorescence micrograph of FIG. 3A1.

FIG. 3B1 schematically shows elution of the analytes. Immediately following the preconcentration step, the field across the SEP element is reversed, redirecting proteins away from the SEP element ($t_3=120.5$ s, $t_4=121$ s).

FIG. 3B2 is the fluorescence micrograph of FIG. 3B1.

FIG. 3C1 schematically shows separation of the analytes. During SDS-PAGE, proteins migrate into the separation channel where they are size-separated. Proteins were observed to begin separating almost immediately after field reversal as the porous polymeric element is immediately adjacent to the SEP element.

FIG. 3C2 is the fluorescence micrograph of FIG. 3C1 which shows the separation of a 7-protein size ladder within a 1-mm distance of the SEP element.

FIG. 4A is a graph showing the change in electrical current as an electric field was applied across (e.g. from B to BW of FIG. 2) the SEP element (B=ground, BW=+400 V, other leads=float) for 15 minutes. Typically, fields are applied less than about 3 minutes for chip based SDS-PAGE or native PAGE separations, but some preferred embodiments bypass the SEP element during most of the separation step by applying the field across the SEP element for only the first about 1 to about 10 seconds and then electrically bypassing the SEP element for the remainder of the separation. The current dropped only when the fields were applied across the SEP element and not when fields bypassed the SEP element (e.g. from S to BW of FIG. 2).

FIG. 4B is an illustration of concentration polarization caused by slight cation selectivity of the SEP element. Depletion of ions resulted in the increase in resistance on the anode side of the SEP element which was coincident with the current drop from FIG. 4A.

FIG. 4C is a graph showing poor reproducibility prior to minimization of concentration polarization effects. Consecutive replicates of native PAGE separations of fluorescently labeled monoclonal IgG antibody is shown. Large variations in concentration factor and elution time were observed due to concentration polarization effects.

FIG. 5A is an electropherograms for different preconcentration times (1 to 4 minutes). The concentrated mixtures of 4 proteins were separated by SDS-PAGE. Without preconcentration, the proteins were just above the detector threshold (control). The peak heights increased in proportion to the time allowed for preconcentration (1 to 4 minutes) and in proportion to protein mobility.

FIG. 5B shows the concentration factors for each protein as a function of loading time. Proteins were concentrated about 400-fold (BSA) to greater than about 1,600-fold (PA) with about 4 minutes of preconcentration. A linear trend was observed between concentration factors and loading time with the slope directly related to the mobility of SDS-protein complexes.

FIG. 5C show the plots for each preconcentration time are linear between log molecular weight and electrophoretic mobilities which is necessary for protein sizing applications. The linear relationship was observed even when protein was concentrated over about 1,000-fold, although with longer preconcentration times, separation mobilities and resolution were reduced.

FIG. 6A is a schematic of the functional layout of device used to assay MMP-8 according to the present invention. The inset shows a 40× brightfield image of the SEP element (visible due to diffraction of incident light).

FIG. 6B is a schematic depicting operation of the device according to FIG. 6A. After a priming step (not depicted), 1 nM Ab* is loaded against the SEP element for 2 minutes. The saliva sample is then loaded against the SEP element and both the Ab* and sample channels are flushed with buffer while the Ab* and sample fluids incubate at the SEP element. An electric potential is then applied across the SEP element, causing the sample and antibody to elute into the separation channel. The potential is then switched, omitting the SEP element from the current path, and the analytes separate and move past the detector.

FIG. 6C shows electropherograms of immunoassay reaction product after mixing, preconcentration, and binding reaction at the SEP. Antibody was loaded first at the SEP followed by sample and binding was specifically between antibody and MMP-8 protein analyte.

FIG. 6D shows a calibration curve for the MMP-8 assay. The detection limit for these assay conditions was about 20 ng/ml and the dynamic range was about 20-1200 ng/ml. Separation was under native PAGE conditions.

FIG. 8A schematically shows a design wherein a sample is loaded into a holding volume defined by the holding channel length and cross-sectional area. Proteins in the holding channel are then swept to the SEP element (the SEP element is in the same location as indicated in FIG. 2).

FIG. 8B show electropherograms for a concentrated mixture of 4 proteins size separated by SDS-PAGE. Without preconcentration, the proteins were just above the detector threshold (control).

FIG. 8C is a graph showing that the peak areas increased in direct proportion to the length of the sample holding segment (about 1 to about 12 mm) that was swept (in this case, corresponding to the number of times a 1 mm holding section was swept). Concentration factors were greater than about 200 by sweeping 12 mm of holding segment. With volume loading, the concentration factors were independent of the mobility of SDS-protein complexes and were also more reproducible than for direct loading of protein (compare to FIG. 5).

FIG. 11A shows analytes being concentrated at SEP A.

FIG. 11B shows the concentrated analytes from SEP A further being concentrated at SEP B.

FIGS. 14A1-14B2 are schematics of a processing area for mixing in an area adjacent to the SEP element.

FIG. 14A1 shows a processing area having two inlet microchannels adjacent to an SEP element and a field being applied to the first inlet microchannel to concentrate an analyte, Species A, at the SEP element.

FIG. 14A2 shows a field being applied to the second inlet microchannel of the processing area to concentrate a second analyte, Species B, at the SEP element after Species A is concentrated according to FIG. 14A1.

FIG. 14B1 shows a processing area having two inlet microchannels adjacent to an SEP element and fields being simultaneously applied to a first inlet microchannel and the second inlet microchannel of the processing area to concentrate two analytes, Species A and Species B, at the SEP element.

FIG. 14B2 shows that lateral diffusion may be necessary for mixing Species A and B at the SEP element after being simultaneously concentrated according to FIG. 14B1.

FIG. 20A shows the concentrated reporter protein (fluorescently labeled anti-CRP, initial concentration of 100 nM) trapped against a SEP element.

FIGS. 20B-20D show snapshots of about a 170-fold concentrated antibody eluting from the membrane after 3 minutes of preconcentration.

DETAILED DESCRIPTION OF THE INVENTION

Figure 1:
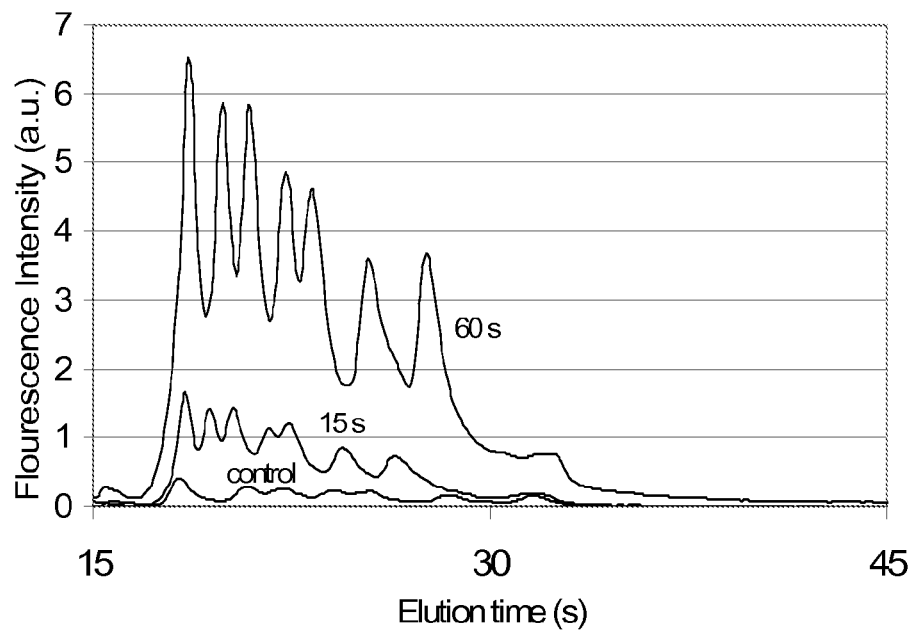
FIG. 1 shows electropherograms of proteins that were concentrated at SEP and separated in liquid sieving gel under SDS denaturing conditions.

The present invention provides methods and devices for preconcentration and separation of analytes in a sample on a microfluidic chip. In particular, the present invention provides microfluidic devices comprising at least one microchannel having at least one polymeric element, a size-exclusion polymeric (SEP) element adjacent to an assay area. In some embodiments, the present invention provides at least one SEP element and at least one second polymeric element, a porous polymeric (PP) element. In some embodiments, the polymeric elements are contiguous to each other. In preferred embodiments, the polymeric elements are polymerized in the microchannel, i.e. in situ fabricated. The polymeric elements described herein are comparatively simpler to fabricate than prior art preconcentration methods. In some embodiments, the SEP element, the PP element or both are cross-linked.

As used herein, "microfluidic" refers to a system or device having one or more fluidic channels, conduits or chambers that are generally fabricated at the millimeter to nanometer scale which allow a fluid to pass through. As used herein, "channel" refers to a structure wherein a fluid may flow. A channel may be a capillary, a conduit, a strip of hydrophilic pattern on an otherwise hydrophobic surface wherein aqueous fluids are confined, and the like. Thus, the "microfluidic channels" or alternatively referred to herein as "microchannels" of the present invention generally have cross-sectional dimensions ranging from about 1 mm or less, preferably between about 1,000 µm and about 1 µm, more preferably between about 500 µm and about 1 µm, most preferably between 100 µm and about 5 µm. As used herein, "a microfluidic channel" is intended to mean one or more channel segments which are in fluidic communication, i.e. a fluid may pass there between. Thus, a second channel segment may be oriented at an angle to a first channel segment, but because the two segments are in fluidic communication, the channel segments are considered to be "a microfluidic channel".

As used herein, a "fluid" refers to a continuous amorphous substance that tends to flow and to conform to the outline of a container such as a liquid or a gas. Fluids include blood, plasma, urine, bile, breast milk, semen, water, liquid beverages, air, saliva and the like. If one desires to test a solid sample for a given protein according to the present invention, the solid sample may be made into a fluid using methods known in the art. For example, a solid sample may be dissolved in an aqueous solution, ground up or liquefied, dispersed in a liquid medium, and the like. Alternatively, the surface of the solid sample may be tested by washing the surface with a solution such as water or a buffer and then testing the solution for the presence of a given analyte. In some situations where the analyte is a protein attached to the surface of a material, the protein may be treated with a proteolytic agent known in the art to cleave the protein or a fragment of the protein from the surface. The sample can be a biological fluid such as urine, breast milk, blood, plasma, saliva, and the like. The sample may be a prepared sample such as a cell extract or an unprepared sample of substance taken in the field, such as water suspected of being contaminated with biological warfare agents and the like.

As used herein, an "analyte" refers to a particle that may be natural or synthetic and includes natural or synthetic chemicals and biomolecules, such as polymers, environmental pollutants, pesticides, insecticides, drugs such as cocaine and antibiotics, magnetic particles, high-magnetic-permeability particles, metal ions, metal ion complexes, inorganic ions, inorganic ion complexes, organometallic compounds, metals including aluminum, arsenic, cadmium, chromium, selenium, cobalt, copper, lead, silver, nickel, and mercury, and the like, amino acids, peptides, proteins, nucleotides, nucleic acids, carbohydrates, lipids, cells, viruses, viral particles, bacteria, organelles, spores, protozoa, yeast, mold, fungi, pollen, diatoms, and the like, and ligands, toxins, biotoxins, hormones, steroids, immunoglobulins, antibodies, supermolecular assemblies, catalytic particles, zeolites, and the like, and biological and chemical warfare agents, agents used in explosives, and the like. As provided herein, a "biomolecule" includes those known in the art, see for example, Wikipedia.org and biological cells. In preferred embodiments, analytes that are concentrated and separated according to the present invention are polypeptides and nucleic acid molecules.

As provided herein, a mobilization field is used to concentrate an analyte and then another mobilization field is used to assay the analyte. As used herein, "mobilization field" refers to any force field that influences a particle to pass through a channel or region of a channel. Mobilization fields include hydrodynamic flow fields produced by pressure differences, gravity, linear or centripetal acceleration, electrokinetic flow fields, electroosmotic flow fields, magnetophoretic and thermophoretic flow fields, electric fields, optical fields, centrifugal fields, gravitational fields, combinations thereof, and the like. In some embodiments, the mobilization fields are electric fields formed by electric current between electrodes operably attached to the microfludic channels and devices described herein.

In some embodiments, the analyte is a biomarker for a given disease, e.g. tumor necrosis factor α (TNFα), interleukin-6 (IL6), C-reactive protein (CRP), or the like, which in amounts that are higher normal amounts are indicative of the disease, such as an inflammatory disease. For example, abnormally high amounts of TNFα, IL6, or CRP in a saliva sample obtained from a subject would indicate that the subject suffers from periodontal disease.

As used herein, a "polypeptide" is used interchangeably with "protein" and "peptide" to refer to a polymeric molecule comprising two or more amino acids linked together.

As used herein, a "nucleic acid molecule" is used interchangeably with "polynucleotide" to refer to a polymer of nucleotides, either single or double stranded.

Generally, as provided herein, analytes are concentrated by the SEP element and then separated using the PP element according to the present invention. As used herein, "concentrating" refers to the reduction of fluid volume per particle in the fluid. When the methods and devices are used to concentrate a fluid, particles in one portion of the fluid become "concentrated" and that particles in the second portion of the fluid become "diluted".

Although successful concentration using SEP elements by size exclusion alone are exemplified herein, the SEP elements of the present invention may be used as a nanofilter for ion-depletion based preconcentration as described by Wang et al. The extent of ion depletion may also be controlled by the choice of monomer elements used to fabricate the SEP element as higher surface charge of the SEP element magnifies concentration polarization effects.

As exemplified herein, analytes may be separated by their electrical charge and size in the PP element. Analytes may be assayed using methods known in the art. See e.g. U.S. Patent Publication No. 20010044108, which is herein incorporated by reference. As used herein, "assaying" is used interchangeably with "detecting", "measuring", "monitoring" and "analyzing".

As used herein an "assay area" is an area in a microfluidic device wherein analytes may be assayed. An assay area includes a microchannel or a section thereof, a PP element, a liquid sieving gel, a surface-coated channel (e.g. a section of a microchannel coated with a chemical or a biomolecule such as an antibody, enzyme, aptamer, nucleic acid molecule, peptide, polypeptide, protein, and the like which may be provided in an array), a polymer containing a chemical or a biomolecule, a microchannel or a section thereof comprising an immobilized biological cell, an area where a secondary microchannel interfaces with a primary microchannel wherein reagents used for assaying the analyte may be added to or mixed with the analyte.

As exemplified herein, a given sample or analyte may be processed in an area adjacent to an SEP element. As used herein, "processing" is used interchangeably with "modifying", "treating", "converting", "changing" and "altering". As used herein, a "processing area" is an area in a microfluidic device wherein a given sample or analytes may be processed. As provided herein a processing area includes an assay area. Sample processing includes adding or removing salt or buffer ions in the sample, altering the pH of the sample, and filtering (adding or removing components of a certain size range) the sample using methods known in the art. Analyte processing includes separating or concentrating an analyte, mixing an analyte with a chemical or biomolecule, reacting an analyte with a reagent, and the like using methods known in the art. The result of analyte processing includes modifying the analyte (e.g. labeling with a dye, cleaving or digesting the analyte, etc.) with a chemical or biological reagent and reversibly binding the analyte (e.g. DNA hybridization, antibody-antigen, protein-protein, protein-DNA, protein-small molecule binding, etc.) using methods known in the art. In some embodiments, a processing area includes an area of a primary microchannel adjacent to an SEP element where at least one secondary microchannel interfaces with the primary microchannel and any chemical or biomolecule delivered therein is mixed or reacted with the analyte.

The present invention provides a simple and inexpensive in situ method for fabricating at least two polymeric elements, e.g. a SEP element contiguous with a PP element, in a microchannel. The microchannels of the present invention may be fabricated on a suitable substrate using methods known in the art. For example, the microfluidic channels can be formed on the surface of the substrate by (1) bulk micromachining, (2) sacrificial micromachining, (3) LIGA (high aspect ratio plating) or (4) other techniques known in the art, or any combination thereof. Such techniques are well known in the semiconductor and microelectronics industries and are described in, for example, Ghandi, VLSI Fabrication Principles, Wiley (1983) and Sze, VLSI Technology, 2nd Ed., McGraw-Hill (1988); Wolf and Taube, Silicon Processing for the VLSI Era, Vol. 1, Lattice Press (1986), and Madou, Fundamentals of Microfabrication, CRC Press (1997); which are herein incorporated by reference.

Substrate Materials

The substrate is preferably made of a material that is suitable for micromachining or microfabrication. In preferred embodiments, the substrate is optically transparent to allow optical detection of analytes in the microchannels. Suitable substrates include silicon, silica, quartz, glass, controlled pore glass, carbon, alumina, titania, tantalum oxide, germanium, silicon nitride, zeolites, gallium arsenide, gold, platinum, aluminum, copper, titanium, Zeonor, TOPAS, polystyrene; poly(tetra)fluoroethylene (PTFE); polyvinylidenedifluoride; polycarbonate; polymethylmethacrylate; polyvinylethylene; polyethyleneimine; poly (etherether)ketone; polyoxymethylene (POM); polyvinylphenol; polylactides; polymethacrylimide (PMI); polyalkenesulfone (PAS); polypropylene; polyethylene; polyhydroxyethylmethacrylate (HEMA); polydimethylsiloxane (PDMS); polyacrylamide; polyimide; and block-co-polymers, and the like, and combinations thereof.

Polymeric Element Materials

Suitable polymers for the polymeric elements include acrylamide (such as linear acrylamide, polyacrylamide, polydimethylacrylamide, polydimethylacrylamide/coacrylic acid, and the like), agarose, methyl cellulose, polyethylene oxide, hydroxycellulose, hydroxy ethyl cellulose, and the like. The polymeric elements of the present invention are preferably solid sieving polymer gels such as those commonly used to separate nucleic acid molecules and proteins.

The polymeric elements may be in situ fabricated in microchips using methods known in the art. See e.g. Song et al. (2004) Anal. Chem. 76:4589; Throckmorton et al. (2002) Anal. Chem. 74:784-789; Herr et al. (2004) Anal. Chem. 76:4727-4733; Han & Singh (2004) J. Chrom. A 1049:205-209; Song et al. (2004) Anal. Chem. 76:2367; Song et al. (2004) Anal. Chem. 76:4589; Yu et al. (2001) J. Electrophoresis 73:5088; Beebe et al. (2000) PNAS USA 97:13488; Brahmasandra et al. (2001) J. Electrophoresis 22:300-311; and Moorthy et al. (2004) J. Electrophoresis 25:1705, which are herein incorporated by reference. Specifically, the microchannels may be filled with a monomer solution and then polymerized in situ. In these embodiments, the monomer solution may contain a photoinitiator and the polymerization is initiated by UV-light and using a mask or a shaped beam, thereby resulting in polymerization that is restricted to UV-exposed regions. See e.g. U.S. Patent Publication No. 20040112751, which is herein incorporated by reference. The unpolymerized monomer solution that was not exposed to UV-light may be removed using methods known in the art. Then the microchannels may be filled with solutions that may be used for chip operations and assay methods such as buffers, reagents, chemicals for reactions, sample containing analyte, and the like.

In preparing the desired polymeric element, various monomers and solvents known in the art may be chosen to provide a polymerized element having a specific distribution of pore size and one which incorporates specific molecules into the polymeric element that impart a specific property the polymeric element and its pore structure. For example, those skilled in the art may readily select a monomer/solvent combination to obtain desired polymer properties such as (i) pore size; (ii) mechanical strength, which can be enhanced by using high polymer cross-linking density (using for example, 1% to 100% of polyfunctional acrylates such as pentaerythritol triacrylate, polyfunctional methacrylate, such as 1,3 butanediol dimethacrylate, or polyfunctional acrylamide, such as methylene bisacrylamide); (iii) hydrophobicity/hydrophilicity, which can be controlled through the choice of monomers, e.g., acrylamide, ethylene glycol diacrylate, or zwitterionic molecules, for hydrophilicity, and alkyl-acrylates for hydrophobicity; (iv) polymer charge, which can be controlled through incorporation of charged monomers into the polymeric element, such as, for example, 2-(acryloyloxy) ethyl ammonium methyl sulfate salt (MOE) for positive charge, 2-acrylamido-2-methyl-1-propanesulfonic acid (AMPS) for negative charge; and (v) substrate specific binding or modification, which can be controlled by adding components such as proteins, antibodies, DNA, enzymes, and the like to the monomer mixture. The added components can be covalently attached to polymer during the polymerization reaction or trapped or encapsulated within the polymer by virtue of small pore size using methods known in the art.

Table 1 provides a few examples wherein a given monomer and solvent ration results in a certain pore size.

TABLE 1

| SOLVENT | MONOMER CROSS-LINKER | SOLVENT MONOMER RATIO | PORE SIZE |
|---|---|---|---|
| Water | 94:6 acrylamide:N,N'-Methylene bisacrylamide | 78:22 | 1-3 nm |
| 20:60:20 Ethanol:Acetonitrile:5 | 70:30 Butylacrylate:1,3 | 67:33 | 1000 nm |
| mM Phosphate buffer pH 6.8 | Butanediol diacrylate | | |
| 1-Propanol | Pentaerythritol triacrylate | 27:73 | 30 nm |
| 96:2:2 Water: 2-Methoxyethanol:10 mM Phosphate buffer pH 5.5 | 95:2 95:2 SPE:N,N'-Methylene bisacrylamide | 60:40 | 1-3 nm |

For example, a monomer such as N,N-dimethyl-N-(2 methacryloyl oxyethyl)-N-(3 sulfopropyl) ammonium betaine (SPE) and a solvent such as water may be employed to obtain an average pore size of about 1 nm to about 3 nm or a monomer such as pentaerythritol triacrylate with a solvent such as 1-propanol may be employed to give an average a pore size of about 30 nm. As another example, the monomers acrylamide and N,N-methylene bisacrylamide and aqueous solvent may be used to give an average pore size ranging from about 1 nm to about 50 nm by adjusting the total percentage of monomer and the ratio of acrylamide bisacrylamide. See e.g. Chui et al. (1995) J. Colloid and Interf. Sci. 174:336-344; Gordon A. H. Lab Techniques in Biochemistry and Molecular Biology, vol. 1 (1971); and Holmes and Stellwagen (1991) Electrophoresis 12:612-619, which are herein incorporated by reference.

In some embodiments, the SEP element is polyacrylamide having a pore size of about 1 nm to about 100 nm. Those skilled in the art may readily obtain a desired pore size by adjusting the acrylamide mixture. For example, the pore size may be adjusted by simply changing the total monomer concentration (% T), while leaving the cross-linker ratio (% C) fixed, according to the equation $r=a/T^{0.5}$ where "r" is the radius "a" is an empirical constant and T is % T. As % T is increased, pore size decreases in a non-linear but predictable manner according to the equation. The pore size can also be adjusted by changing the crosslinker percentage (% C) and increasing % C will decrease the value of "a" (meaning a decrease in pore size for a given % T) in the above equation.

In some embodiments, a second monomer solution may be introduced in the area of the microchannel adjacent to the SEP element and polymerized to give two contiguous polymeric elements in the microchannel. The second polymeric element may be another SEP element or a PP element comprised of a sieving medium. The PP element need not be a solid polymer gel, but may be a liquid sieving gel. The liquid sieving gel can be a high viscosity solution known in the art such as a buffer containing a high percentage of a polysaccharide, e.g. sucrose or dextran, or a solution of entangled linear polymers such as linear polyacrylamide, polyethylene oxide, and the like.

FIG. 1 is an electropherogram for SEP preconcentration and SDS capillary gel electrophoresis (CGE) based separation using a liquid entangled polymer solution. For these experiments, a 7 protein fluorescent sodium dodecyl sulfate polyacrylamide gel electrophoresis (SDS-PAGE) sizing standard (Benchmark™ molecular weight ladder, Invitrogen, Carlsbad, Calif.) was concentrated at a 22% T, 6% C SEP element for the times shown. The concentrated proteins were then separated with a liquid sieving gel (SDS 14-200, Beckman Coulter Inc., Fullerton, Calif.) and detected by laser induced fluorescence at a distance of 10 mm from the SEP element. Much higher protein levels were detected with 15 and 60 second preconcentration times compared to the control condition where a standard t-injection of protein (without an SEP element) was separated under the same conditions.

Other sieving mediums known in the art may be used as the PP element. For example, sieving mediums suitable for use in chromatography, gel electrophoresis, and other liquid phase separations may be used. See e.g. Weiss (1995) Ion Chromatography VCH Publishers Inc.; Baker (1995) Capillary Electrophoresis John Wiley and Sons; Kuhn (1993) Capillary Electrophoresis: Principles and Practice Springer Verlag; Righetti (1996) Capillary Electrophoresis In Analytical Biotechnology CRC Press; Hill (1992) Detectors For Capillary Chromatography John Wiley and Sons; Gel Filtration: Principles and Methods (5th Edition) Pharmacia; Gooding and Regnier (1990) HPLC of Biological Macromolecules: Methods and Applications (Chrom. Sci. Series, volume 51) Marcel Dekker and Scott (1995) Techniques and Practices of Chromatography Marcel Dekker, Inc.; Affinity Chromatography—a Practical Approach, Dean et al. (Eds.) IRL Press, Oxford (1985); and Chromatographic Methods, 5th Edition, Braithwaite et al. (1996), which are herein incorporated by reference.

Other media may be incorporated into the polymeric elements such as non-ionic macroreticular and macroporous resins, sephacryl, sephadex, sepharose, superdex, superose, toyopearl, agarose, cellulose, dextrans, mixed bead resins, polystyrene, nuclear resins, DEAE cellulose, Benzyl DEA cellulose, TEAE cellulose, silica gels, agarose based gels, acrylamide based gels, Genescan polymers, colloids and colloidial solutions, such as protein colloids (gelatins), and hydrated starches, and the like. Other media that may be incorporated into the polymeric elements may also include affinity media for purification and separation of molecular components, such as acrylic beads, agarose beads, cellulose, sepharose, sepharose CL, toyopearl, or the like, chemically linked to an affinity ligand, such as a biological molecule. A wide variety of activated matrixes, amino acid resins, avidin and biotin resins, carbohydrate resins, dye resins, glutathione resins, hydrophobic resins, immunochemical resins, lectin resins, nucleotide/coenzyme resins, nucleic acid resins, and specialty resins are available and may also be used in the present invention.

Monomers may be polymerized using methods known in the art. Photopolymerization is a preferred method to obtain a desired thickness, shape, or both of the polymeric element since the shape and thickness of a polymeric element may be controlled by controlling the excitation light beam focus and collimation. Since photo-initiated radical diffusion, solvent-phase polymer diffusion, and bulk fluid motion within the microchannel negatively effect the thickness of the polymeric element, they can be controlled by eliminating bulk fluid flow before initiating polymerization, and by the incorporation of polymerization inhibitors to minimize radical diffusion using methods known in the art.

Free-radical polymerizable monomers that photopolymerize, or can be made photopolymerizeable by the addition of, e.g. energy transfer dyes may be used according to the present invention. For example, free-radical polymerizable monomers such as acrylamide, substituted acrylamides, acrylate, methacrylate, vinyl ester functionalized materials, and the like may be used as well as monomers and/or oligomers of (meth)acrylates (meth)acrylamides, acrylamides, vinyl pyrrolidone and azalactones such as mono-, di-, or poly-acrylates and methacrylates such as methyl acrylate, methyl methacrylate, ethyl acrylate, isopropyl methacrylate, isooctyl acrylate, isobornyl acrylate, isobornyl methacrylate, acrylic acid, n-hexyl acrylate, stearyl acrylate, allyl acrylate, glycerol diacrylate, glycerol triacrylate, ethylene glycol diacrylate, diethyleneglycol diacrylate, triethyleneglycol dimethacrylate, 1,6-hexanediol diacrylate, 1,3-propanediol diacrylate, 1,3-propanediol dimethacrylate, trimethanol triacrylate, 1,2,4-butanetriol trimethylacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyl-dimethylmethane, bis[1-(3-acryloxy-2-hydroxy)]-propoxyphenyl dimethylmethane, tris-hydroxyethyl isocyanurate trimethacrylate; the bis-acrylates and bis-methacrylates of polyethylene glycols of molecular weight 200-500, copolymerizable mixtures of acrylated monomers, acrylated oligomers, PEG diacrylates, and the like. Strongly polar monomers such as acrylic acid, acrylamide, itaconic acid, hydroxyalkyl acrylates, or substituted acrylamides or moderately polar monomers such as N-vinyl-2-pyrrolidone, N-vinyl caprolactam, and acrylonitrile may also be used.

Proteins such as gelatin, collagen, elastin, zein, and albumin, whether produced from natural or recombinant sources, which are made by free-radical polymerization by the addition of carbon-carbon double or triple bond-containing moieties, including acrylate, diacrylate, methacrylate, ethacrylate, 2-phenylacrylate, 2-chloroacrylate, 2-bromoacrylate, itaconate, oliogoacrylate, dimethacrylate, oligomethacrylate, acrylamide, methacrylamide, styrene groups, and other biologically acceptable photopolymerizable groups, can also be used according to the present invention.

Photoinitiators known in the art including 2,2'-azobis (2-amidinopropane) dihydrochloride; 2,2'-azobis 2-methyl-N-(2-hydroxyethyl) propionamide; 2,2'-azobisisobutyronitrile; 2,2'-azobis(N,N'-dimethyleneisobutyramidine) dihydrochloride; 2,2'-azobis (N,N'-dimethyleneisobutyramidine); 4,4'-azobis(4-cyanopentanoic acid); 2-(carbamoylazo) isobutyronitrile; 2,2'-azobis(4-methoxy 2,4-dimethylvaleronitrile); dimethyl 2,2"-azobisisobutyrate; 2,2'-azobis(2-methyl butyronitrile); and IRGACURE™ photoiniators (Ciba Specialty Chemicals Inc., Tarrytown, N.Y.) may be used according to the invention.

Dye-sensitized polymerization methods known in the art may also be used according to the present invention. For example, light from an argon ion laser (514 nm), in the presence of a xanthin dye and an electron donor, such as triethanolamine, to catalyze initiation, may be used to induce a free radical polymerization of acrylic groups in a reaction mixture. See Neckers, et al. (1989) Polym. Materials Sci. Eng. 60:15; and Fouassier, et al. (1991) Makromol. Chem. 192: 245-260, which are herein incorporated by reference. Suitable photosensitive dyes for initiating polymerization include ethyl eosin, eosin Y, fluorescein, 2,2-dimethoxy-2-phenyl acetophenone, 2-methoxy, 2-phenylaceto-phenone, camphorquinone, rose bengal, methylene blue, erythrosin, phloxime, thionine, riboflavin, methylene green, acridine orange, xanthine dye, thioxanthine dye, and the like.

Cocatalysts known in the art may also be employed according to the present invention. Suitable cocatalysts include primary, secondary, tertiary or quaternary amines, triethanolamine, triethylamine, ethanolamine, N-methyl diethanolamine, N,N-dimethyl benzylamine, dibenzyl amine, N-benzyl ethanolamine, N-isopropyl benzylamine, tetramethyl ethylenediamine, potassium persulfate, tetramethyl ethylenediamine, lysine, ornithine, histidine, arginine, and the like.

Examples of a dye/photoinitiator system include ethyl eosin with an amine, eosin Y with an amine, 2,2-dimethoxy-2-phenoxyacetophenone-, 2-methoxy-2-phenoxyacetophenone, camphorquinone with an amine, and rose bengal with an amine. In some cases, the dye may absorb light and initiate polymerization, without any additional initiator such as an amine. In these cases, only the dye and a monomer need be present to initiate polymerization upon exposure to light. The generation of free radicals is terminated when the laser light is removed. For example, 2,2-dimethoxy-2-phenylacetophenone does not require any auxiliary amine to induce photopolymerization.

A "label" is a moiety that is detectable by spectroscopic, photochemical, biochemical, immunochemical, or chemical methods known in the art and includes dyes, radiolabels, fluorophores, chemophores, quantum dots, enzymes, isotopes, and the like.

As disclosed herein, polypeptides were concentrated on the upstream side of the SEP element having a molecular weight cut-off of about 10 kDa. Other molecular weight cut-off values are contemplated herein and such values are only dependent on the size of the analyte to be sieved. For example, to assay only polypeptides of about 15 kDa in a sample which also comprises fragments ranging from less than 15 kDa, a SEP element having a molecular weight cut-off of about 15 kDa may be used. Fragments smaller than about 15 kDa will pass through the SEP element and may be collected in a collection reservoir while the polypeptides of interest are concentrated on the upstream side of the SEP element. Then the polypeptides to be analyzed are eluted away from the SEP element by reversing the electric field and separated in the PP element.

The mobilities of the concentrated polypeptides were log-linear with respect to their molecular weights, thereby demonstrating the suitability of this approach for protein sieving. The methods and devices of the present invention provided rapid (less than about 5 minutes) analyte preconcentration with concentration factors over about 1,000 (e.g. a 30-minute concentration affords about a 10,000-fold concentration factor) and separation. The methods and devices also provided detection and baseline resolution of proteins at concentrations as low as about 50 fM with a 30 minute preconcentration time. Therefore, the methods and devices of the present invention allow the analysis of samples comprising low-abundant polypeptides and other analytes such as nucleic acid molecules that are not readily detectable using conventional methods known in the art.

The contiguous arrangement of the SEP element and the PP element in the same channel resulted in a zero dead-volume integration of the protein preconcentration and separation functions which avoids band-broadening resulting from flow variations due to differences in zeta potential and tortuosity in the open and polymer-filled segments. See Rathore & Horvath (1998) Anal. Chem. 70:3069, which is herein incorporated by reference. The resolution of polymeric elements in channels was determined by the photopatterning technique used to fabricate them as disclosed herein. As provided herein, the SEP element had about a 5 to about a 10-fold higher electrical resistance than the PP element based on current and voltage probe measurements at nodes on either side of the T-junction (R=V/I).

To minimize the voltage drop across the SEP element and thereby retain a high field for separation, the SEP element was fabricated with a short axial length (about 50 μm) compared to the PP element (about 15 mm). Nevertheless, in preferred embodiments, the SEP element is thinner than the PP element. Preferably the SEP element is about 1 μm to about 1 mm, preferably about 1 μm to about 100 μm, more preferably about 10 μm to about 50 μm and the PP element about 1 mm to about 100 cm, preferably about 1 mm to about 5 cm, more preferably about 3 mm to about 2 cm.

While projection lithography enables fabrication of features having dimensions of about 10 μm or less (dependent on the wavelength and the numerical aperture of the focusing lens), mechanical robustness constraints and ease of fabrication led to the choice of a slightly larger minimum SEP element dimension. See Madou, M. (1997) Fundamentals of Microfabrication, CRC Press, New York, which is herein incorporated by reference. However, those skilled in the art may readily optimize the dimension using methods known in the art including photolithography. The PP element does not require high resolution and was made by contact photolithography where resolution, dependent on the wavelength of light used as well as the thickness of the glass wafer, was about 60 μm. See Holmes & Stellwagen (1991) J. Electrophoresis 12:612, which is herein incorporated by reference.

Cross-linked polyacrylamide, was used as the sieving material for the SEP element and the PP element as polyacrylamide is hydrophilic, inert, shows minimal non-specific adsorption of proteins, and can be polymerized in an aqueous buffer avoiding organic solvents that may leave a residual or suffer from incompatibility with chip materials or biological samples. However, other polymers known in the art may be employed. The PP element exemplified herein was an 8% polyacrylamide (2.5% C) solution tailored for size-based separation of proteins in the molecular weight range of about 20 to about 200 kDa. However, a desired pore size of an acrylamide polymeric element may be readily selected and implemented using methods known in the art. See Holmes & Stellwagen (1991) J. Electrophoresis 12:612; Holmes & Stellwagen (1991) J. Electrophoresis 12:253; and Chui et al. (1995) J. Colloid and Interface Science 174:336, which are herein incorporated by reference.

The percentage of acrylamide and bisacrylamide used to fabricate a SEP element (both total monomer (% T) and crosslinker (% C)) should be higher than that used for a typical PP element so that pore sizes are small enough to exclude larger analytes (e.g. proteins greater than about 10 kDa) but pore sizes must also be large enough to maintain permeability to buffer ions and other smaller analytes as desired. Thus, acrylamide/bisacrylamide SEP elements from about 15 to about 27% T and about 5 to about 9% C are preferred. However, those skilled in the art may readily optimize and obtain polymeric elements of desired size-exclusion cut-off characteristics using methods known in the art. In addition to size exclusion, one skilled in the art may readily select a polymer concentration to limit the electrical resistance of the SEP element which (1) contributes to joule heating and (2) lowers the applied fields available to neighboring channels due to voltage division, reduce concentration polarization, or both.

Figure 2:
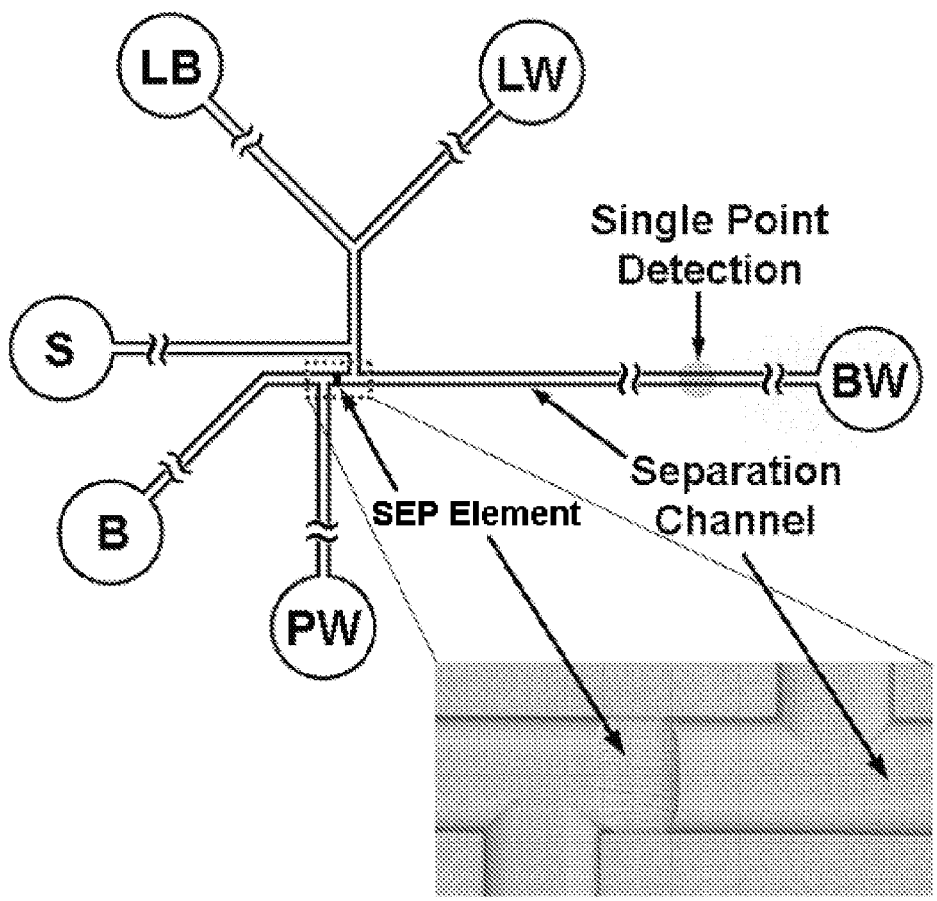
FIG. 2 shows an example of a microfluidic device design for integrated preconcentration and separations according to the present invention. The inset shows a bright-field image of a photopolymerized size-exclusion polymeric (SEP) element (visible due to light scattering) positioned in the offset-T junction. A polyacrylamide porous polymeric (PP) element was photopolymerized contiguous with the SEP element in the microfluidic channel (separation channel). Analytes are detected in the separation channel. The microfluidic reservoirs are labeled as follows: sample (S), buffer (B), preconcentration waste (PW), buffer waste (BW), load buffer (LB), load waste (LW).

Acrylamide/bisacrylamide SEP elements of about 22% T and 6% C were exemplified herein for DNA and protein preconcentration as the pore sizes were empirically determined to be close to the size-exclusion cutoff for proteins greater than about 10 kDa (data not shown), however, the preconcentration and analysis of other biomolecules known in the art are also contemplated herein. With 20% T 5% C SEP elements, a significant fraction of protein reaching the SEP element became entangled within the SEP element. All polymeric elements tested were optically clear except for a 27% T 9% C gel, presumably because the high cross-linker percentage resulted in a different regime of polymerization where pore sizes have been shown to increase by raising the crosslinker percentage too high. See Margolis & Wrigley (1975) J. Chromatography 106:204, which is herein incorporated by reference. A bright-field micrograph of an integrated chip with a photopolymerized SEP element and PP element is shown in FIG. 2 (inset).

The SEP element was found to trap not only SDS-denatured proteins, but also pure SDS micelles which results in slower migration of eluted proteins at longer preconcentration times by destacking Concentration polarization and ion depletion on the anode side of the SEP element were also found to give poor reproducibility in concentration factors and elution times. Furthermore, the stacking of SDS micelles during preconcentration was found to dramatically enhance ion selectivity of the SEP element leading to more pronounced concentration polarization. Therefore, the likelihood of concentration polarization effects should be considered even when using SEP elements presumed to rely on a size-exclusion mechanism for trapping proteins (i.e. have very low surface charge density) particularly for typical SDS-PAGE conditions.

Figure 6A:
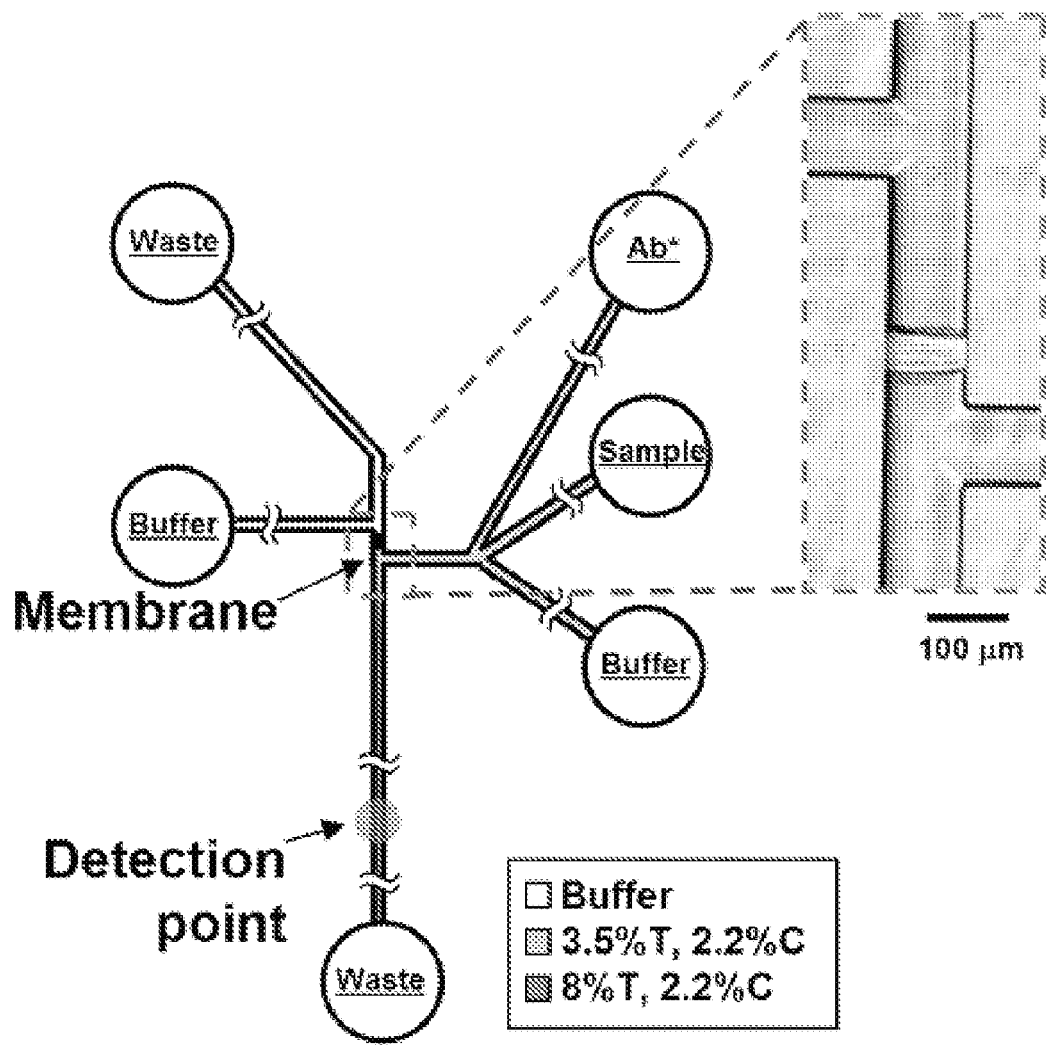
FIGS. 6A-6D exemplifies an assay conducted in accordance with the present invention and the results. Fluid wells are labeled by their contents, where "Ab*" refers to fluorescently labeled antibody to MMP-8, "Sample" refers to 1:5 diluted saliva, and all other wells contain buffer. Polyacrylamide gel characteristics are indicated by the grayscale channel color where % T is the fraction of total acrylamide and % C is percentage of bis-acrylamide cross-liker.
Figure 6B:
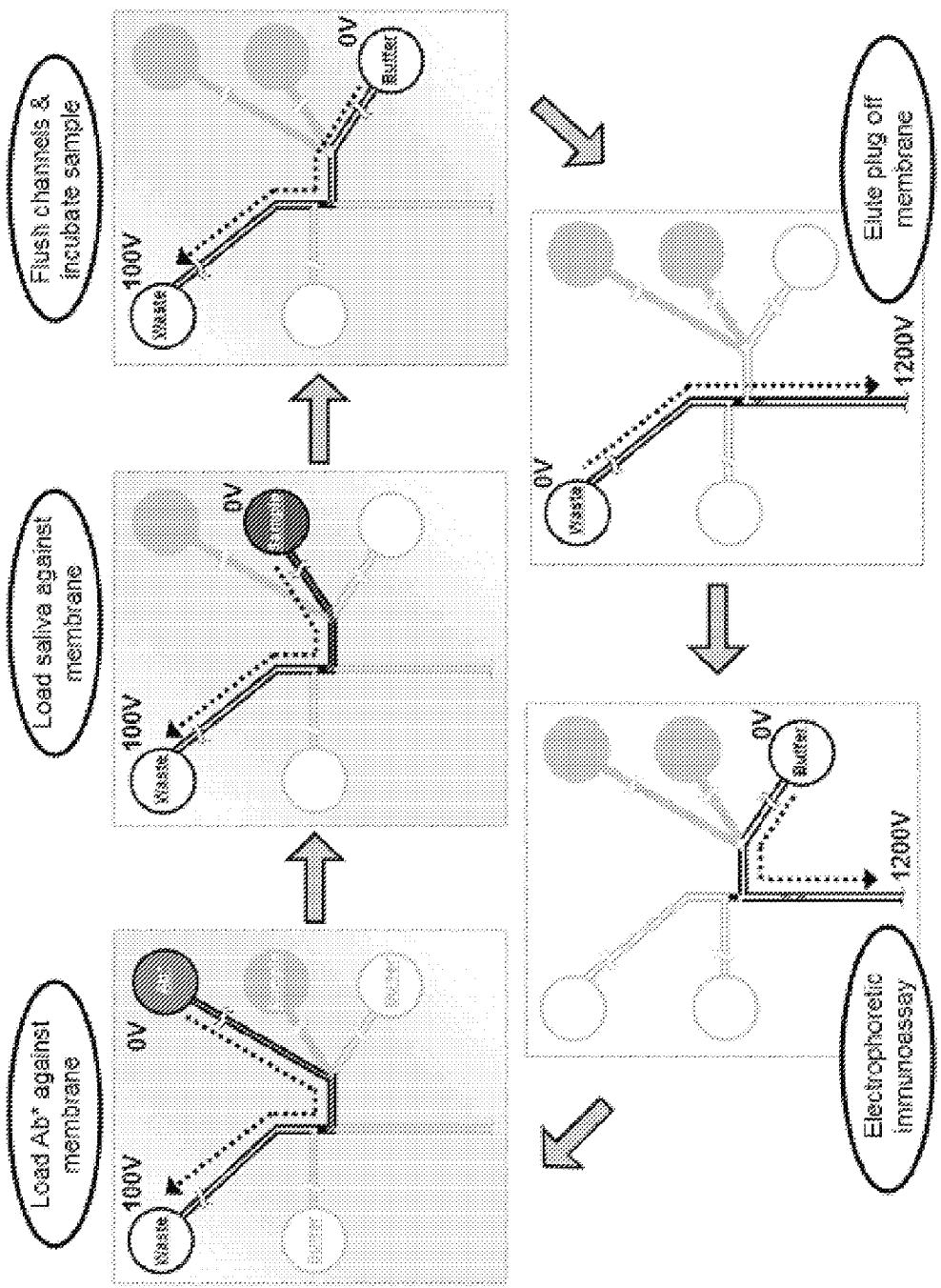
Figure 6C:
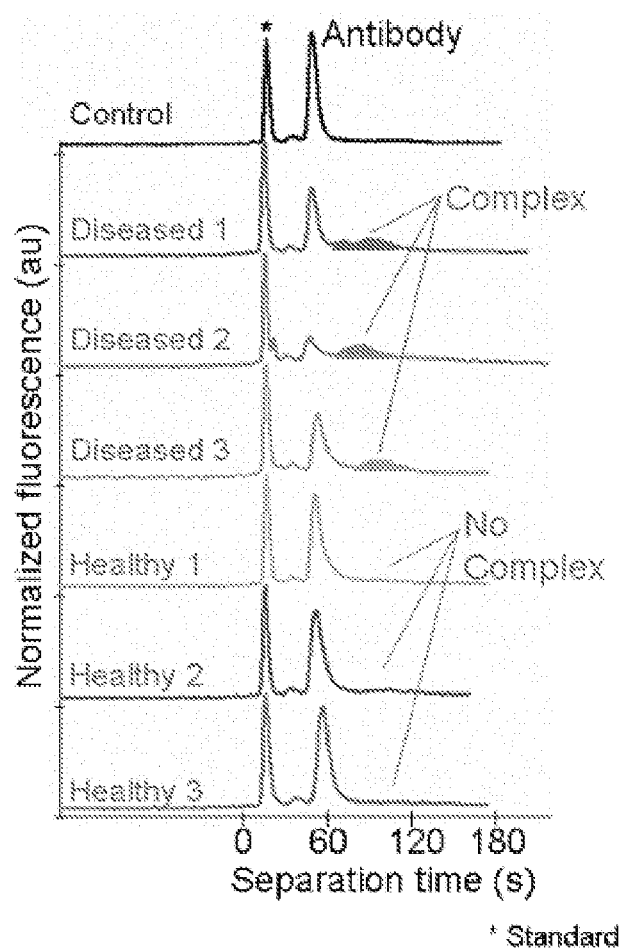
Figure 6D:
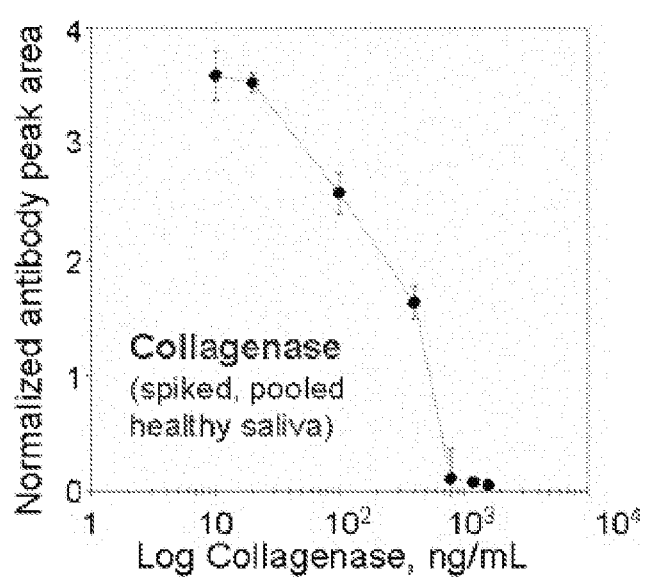

As disclosed herein, concentration polarization was minimized by (1) using an open channel on the preconcentration-waste side of the SEP element which allows fluid flow to replenish buffer ions during the preconcentration step, and also by (2) bypassing the SEP element, i.e. changing the electric field as exemplified in FIG. 6B, during most of the separation step. When the field is applied from waste side (the side opposite along the field lines to where the analyte is trapped and molecules that co-electrophoreses with analyte and are not excluded from the pores of the SEP element would end up on the waste side) to the end of the separation channel it is crossing the SEP element which results in concentration polarization. Immediately after the concentrated analyte is injected into the separation channel, the field is switched to "bypass" the SEP shown in FIG. 6B as going from buffer through the separation channel a high field can then be maintained for most of the time required to separate the proteins.

The dependence of concentration factors on analyte mobilities was also eliminated by using a swept-volume approach to sample loading. This swept-volume approach showed significantly less deviation in concentration factors as compared to direct loading by overcoming concentration polarization effects. Further, the swept-volume approach is less dependent on sample conductivity, pH, viscosity, and other factors that could alter the rate of analyte loading as is direct loading.

Thus, the present invention provides robust methods and devices for assaying low abundance analytes, even those in complex sample matrices, which cannot be analyzed by conventional sizing techniques.

I. Fabrication

The following reagents were used to fabricate and test devices and methods of the present invention: N,N methylene bisacrylamide powder and solutions of 3-(trimethoxysilyl) propyl methacrylate (98%), 40% acrylamide, and 30% (37.5:1) acrylamide/bisacrylamide solutions were from Sigma (St. Louis, Mo.). 10× Tris/glycine/SDS electrophoresis buffer (25 mM Tris, 192 mM glycine, 0.1% SDS, pH 8.3 at 1×) was from BioRad (Hercules, Calif.). The water soluble photoinitiator 2,2'-azobis(2-methyl-N-(2-hydroxyethyl)propionamide) (VA-086) was from Wako Chemicals (Richmond, Va.). Glacial acetic acid was also from Sigma. The Alexa Fluor 488-labeled proteins parvalbumin (PA), trypsin inhibitor (TI), ovalbumin (OA), and bovine serum albumin (BSA), as well as NuPAGE sample reducing buffer were from Invitrogen (Carlsbad, Calif.). A stock solution of 22% (15.7:1) acrylamide/bisacrylamide was prepared by combining bisacrylamide powder, 40% stock acrylamide, and water and filtering with a 0.2 µm syringe filter.

Photolithography, wet etching, and bonding techniques known in the art were used to fabricate microfluidic devices according to the present invention from Schott D263 glass wafers (4 in. diameter, 1.1 mm thickness; S. I. Howard Glass Co. Worcester, Mass.). See Throckmorton et al. (2002) Anal. Chem. 77:4293-4299, which is herein incorporated by reference. The channels were about 40 µm deep×about 100 µm wide. To anchor the polymeric elements to the channel walls, the channel walls were first coated with acrylate-terminated self-assembled monolayers according to methods known in the art. See e.g. Herr & Singh (2004) Anal. Chem. 76:4727-4733, which is herein incorporated by reference. The channels were conditioned with 1M NaOH, rinsed with deionized water and purged by vacuum. The dried channels were loaded with a sonicated and degassed 2:3:5 (v/v/v) mixture of 3-(trimethoxysilyl)propylmethacrylate, glacial acetic acid, and deionized water. The mixture was incubated for 30 minutes to deposit a packed silane monolayer, rinsed with a 3:7 mixture of acetic acid and water, rinsed with deionized water and purged by vacuum.

IA. The SEP Element

To fabricate the SEP elements, the microchannels were loaded by capillary action with a degassed monomer/photoinitiator solution of 22% (15.7:1) acrylamide/bisacrylamide containing 0.2% (w/v) VA-086 photoinitiator. The inlet port was cleared and then all ports were filled with 1 µl of monomer/photoinitiator solution, covered to prevent evaporation, and equalized for 5 minutes to eliminate pressure driven flow. The narrow, about 50 µm, SEP element was photopolymerized with a 15 second exposure to a rectangular shaped 355-nm laser beam using an optical setup described previously. See Song et al. (2004) Anal. Chem. 76:4589 and Song et al. (2004) Anal. Chem. 76:2367, which are herein incorporated by reference. The unpolymerized monomer solution was purged from the channels by vacuum. The empty channels were then rinsed with either buffer or buffered monomer solution used to form the PP element.

IB. The PP Element

The PP element was photopolymerized after formation of the SEP element by loading a degassed solution of 8% (37.5:1) acrylamide/bisacrylamide and 0.2% (w/v) VA-086 in 1× tris/glycine/SDS buffer into the separation channel in an area contiguous to the SEP element. The area where the PP element was to be formed was patterned using a contact mask and exposed to light from a 100 W 365-nm lamp for 5 minutes to photopolymerize the PP element. The chips were stored in buffer at 5° C. when not in use.

IC. The Microfluidic Device

A custom manifold similar to that described by Renzi et al. was used to mount the chip to an optical setup, a supply sample and reagents, and interface power supply leads. See Renzi et al. (2005) Anal. Chem. 77:435, which is herein incorporated by reference. An aluminum backing plate secured the device against a custom machined acetal resin (Delrin®, DuPont, Wilmington, Del.) sample tray with O-ring compression fittings that sealed individual sample reservoirs over the chip inlets. The centers of the aluminum backing plate and sample tray were open for optical access to the chip. Programmable high-voltage power supplies with current monitoring capabilities were fabricated in-house according to Renzi et al. A custom high input resistance ($10^{11}$ ohm) voltage probe was used to track node voltages at channel intersections during chip operation while imposing a negligible load on the circuit.

Microscope images were captured by a 1300×1030 pixel, Peltier-cooled interline CCD camera (CoolSnap HQ, Roper Scientific, Trenton, N.J.) mounted on an inverted epifluorescence microscope (IX-70, Olympus, Melville, N.Y.). The images presented illustrate qualitative chip behavior; spatial nonuniformities in the excitation and collection efficiencies of the optical system were not corrected. Electropherograms were generated using an argon ion laser beam (488 nm) with a frequency modulated (220-Hz mechanical chopper) for excitation. Epifluorescence optics with a 40× objective and a Hamamatsu H5784 photomultiplier tube (PMT) were used for detection. The PMT signal was demodulated using a lock-in amplifier (Stanford Research Systems, Sunnyvale, Calif.). The demodulated PMT signal and voltage probe readings were captured using a data acquisition interface (6020E DAQPad, National Instruments, Austin, Tex.) controlled by a laptop and a custom LabVIEW (National Instruments, Austin, Tex.) program.

FIG. 2 schematically shows a device according to the present invention. A sample was loaded directly from the sample (S=ground) reservoir to the preconcentration waste (PW=300 V) reservoir to trap and preconcentrate proteins at the SEP element (E=135 V/cm). Sample was followed up with loading buffer for 30 seconds (LB=0, PW=300 V) to clean up protein remaining in the short microchannel segment leading to the SEP element. Trapped sample proteins were subsequently eluted and separated in a single step toward the buffer waste (BW=1200 V) reservoir with the buffer (B) reservoir grounded (other wells=float, E=320 V/cm).

To reduce concentration polarization in later experiments, fields were applied across the SEP element for only 10 seconds for elution (B=ground, BW=1200 V) and the elution was also pinched so that ⅓ of the current was from LB (set at 120 V in this case). For the remainder of the separation, LB was grounded instead of B so that the applied field bypassed the SEP element. For volume loading experiments, sample proteins were first loaded into a holding reservoir by applying the field between S and load waste (LW) reservoirs (S=ground, LW=500 V) rather than loading directly from sample toward the SEP element. The protein in the sample loop was then swept to the SEP element (LB=ground, PW=300 V).

QUANTIFYING PERFORMANCE. The peak areas in all cases were normalized by elution time (peak area/elution time). Concentration factors were determined by normalizing the electropherogram peak areas by corresponding peaks from control tests (preconcentrated peak area/control peak area). The control data was generated with a standard T-injection using a chip fabricated without a SEP element. Peak areas were calculated using methods known in the art.

II. Preconcentration and Separation

The layout of design used for different modes of preconcentration is shown in FIG. 2. To concentrate and separate proteins, chip operations were similar to established protocols for offset-T injections except that a SEP element was positioned in the offset (FIG. 2). During preconcentration, an electric field was applied across the SEP element between the sample (S) and preconcentration waste (PW) reservoirs (S=ground, PW=+V, other leads=float), causing negatively charged protein/SDS complexes to migrate toward the SEP element where they were trapped and concentrated.

FIG. 3A1 and the fluorescence micrographs in FIG. 3A2 show the accumulation of fluorescently-labeled BSA at the SEP element for different time points during the preconcentration step. Once the desired level of preconcentration was achieved, a separation step was commenced wherein the band of concentrated sample protein was eluted from the SEP element and injected into the separation channel.

Elution and injection were achieved by reversing the electrical field polarity across the SEP element between the buffer (B) and buffer waste (BW) reservoirs (B=ground, BW=+V, other leads=float). Proteins cleanly eluted from the SEP element and were separated into distinct bands within a short distance from the SEP element, as shown in FIGS. 3B1 and 3C1 and the fluorescence micrographs in FIGS. 3B2 and 3C2.

Refinements to the protocol, including incorporation of additional channels and manipulation steps, as discussed herein, were made to clear sample from the loading channel, pinch injections, minimize concentration polarization, and give the option of fixed-volume sample loading. Protein preconcentration may be further optimized by those skilled in the art using methods known in the art including varying the voltage during electrophoretic injection of the sample, controlling the sample volume loaded, and the like.

Proteins ranging in size from about 12 kDa to about 205 kDa were effectively trapped at the SEP element and eluted cleanly as shown in FIGS. 3A1-3C2. Fluorescence imaging showed that proteins in this range did not permeate or become entangled within the SEP element, but were instead concentrated within a narrow region immediately adjacent to the SEP element surface. The protein eluted as a sharp band when the field was reversed leaving a negligible trace of fluorescence indicating minimal fouling or non-specific interactions with the polymeric elements used. See FIG. 3B2. Unincorporated dye molecules present in trace quantities passed through the SEP element, as was verified by imaging of fluorescein transport during preconcentration. Thus, the SEP element may be used for rapid sample cleanup, e.g. for removing unincorporated dye or for buffer exchange.

III. Concentration Polarization

Figure 4A:
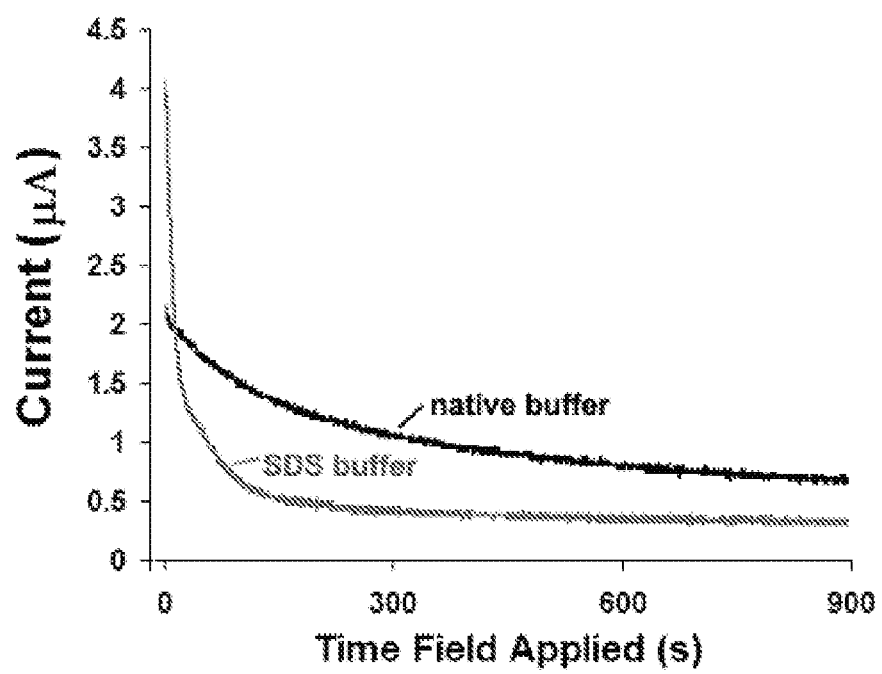
FIGS. 4A-4C show concentration polarization effects arising from electric fields applied across the size-exclusion polymeric element.

For the slightly basic conditions used herein, hydrolysis of a small percentage of polymer amide bonds can be expected leaving negatively charged carboxylic groups on the polymer. See Kleparnik & Mikuska (2004) J. Electrophoresis 25:2139, and Kurenkov et al. (2001) Russian J. of Applied Chem. 543, which are herein incorporated by reference. With the fixed polymer charge and small pore sizes in the SEP element, the thickness of the electrical double layer (EDL) can be on the order of the pore radius. The negative surface charge and EDL overlap imparts partial cation selectivity to the SEP element resulting in preferential enrichment of cations and exclusion of co-ions (anions). In the presence of an externally applied electrical field, the SEP element selectivity for cations induces concentration polarization in the bulk solution on both sides of the SEP element as illustrated in FIG. 4B. See Helfferich, F. (1962) J. Am. Chem. Society 84:3237; and Tallarek et al. (2005) Electrophoresis 26:3237, which are herein incorporated by reference. At the anodic side of the SEP element, counterions are depleted and, to maintain electroneutrality, total ion concentration decreases compared to the bulk. The decrease in ionic concentration in the boundary layer that extended well into the channel on the anode side, leading to a higher resistance, results in a net decrease in current as a function of time as shown in FIG. 4A. The drop in current is exponential—an initial sharp decline is followed by attainment of a limiting non-zero value when cation concentration reaches equilibrium. At this point electromigration of cations into the pores of the SEP element is counterbalanced by replenishment from the anodic side of the channel by electromigration and diffusion.

Concentration polarization effects were monitored by measuring resistance in different sections of the chip using a high voltage probe. See FIG. 4B. There was not a significant change in the resistance across the SEP element or on the cathodic side. However, there was a significant increase in resistance with time on the anodic side of the SEP element leading to a drop in current as shown in FIG. 4A. The drop in current was not only observed in experiments with SDS denatured proteins, but also with newly fabricated chips exposed only to native Tris glycine buffer (no SDS and no added protein). However, with SDS in the buffer, the drop in current was more rapid. Adding protein at the concentrations tested did not affect the rate of current drop, and current drops were only observed when field was applied across the SEP element (e.g. with a fresh or equilibrated chip, electric currents were stable when fields were applied along paths that bypassed the SEP element). A modest increase in local ionic strength was observed on the cathodic side of the SEP element which led to a destacking effect when the field was reversed for elution. The polarization gradually dissipated by diffusion after the applied field was removed.

Figure 4C:
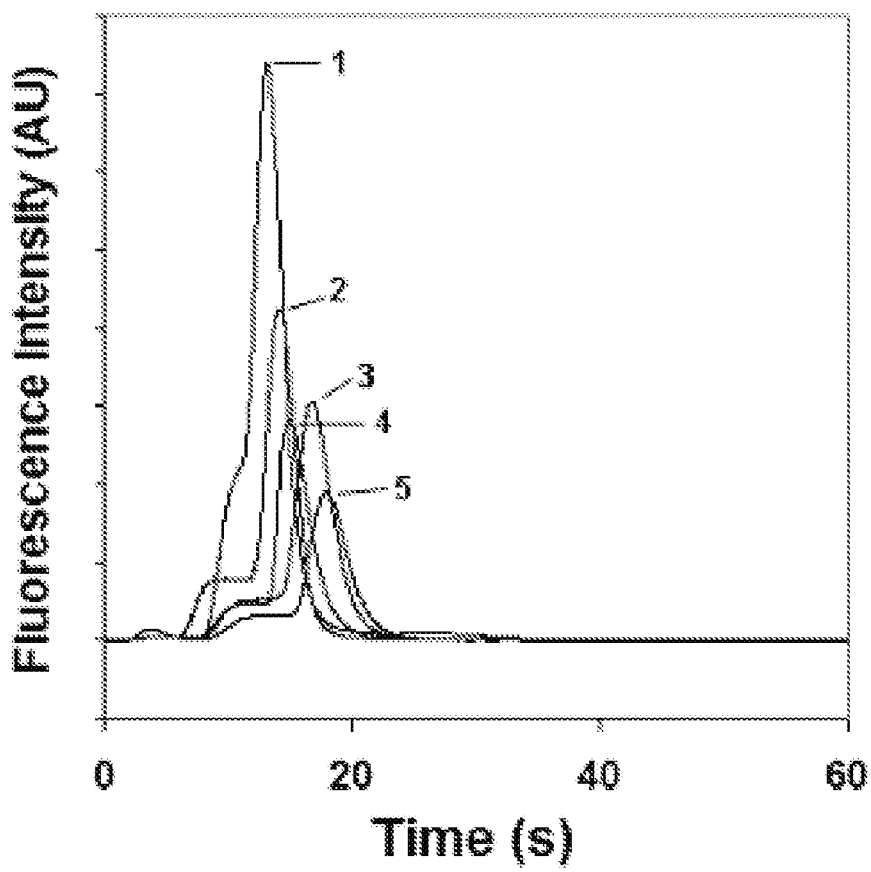
Figure 4B:
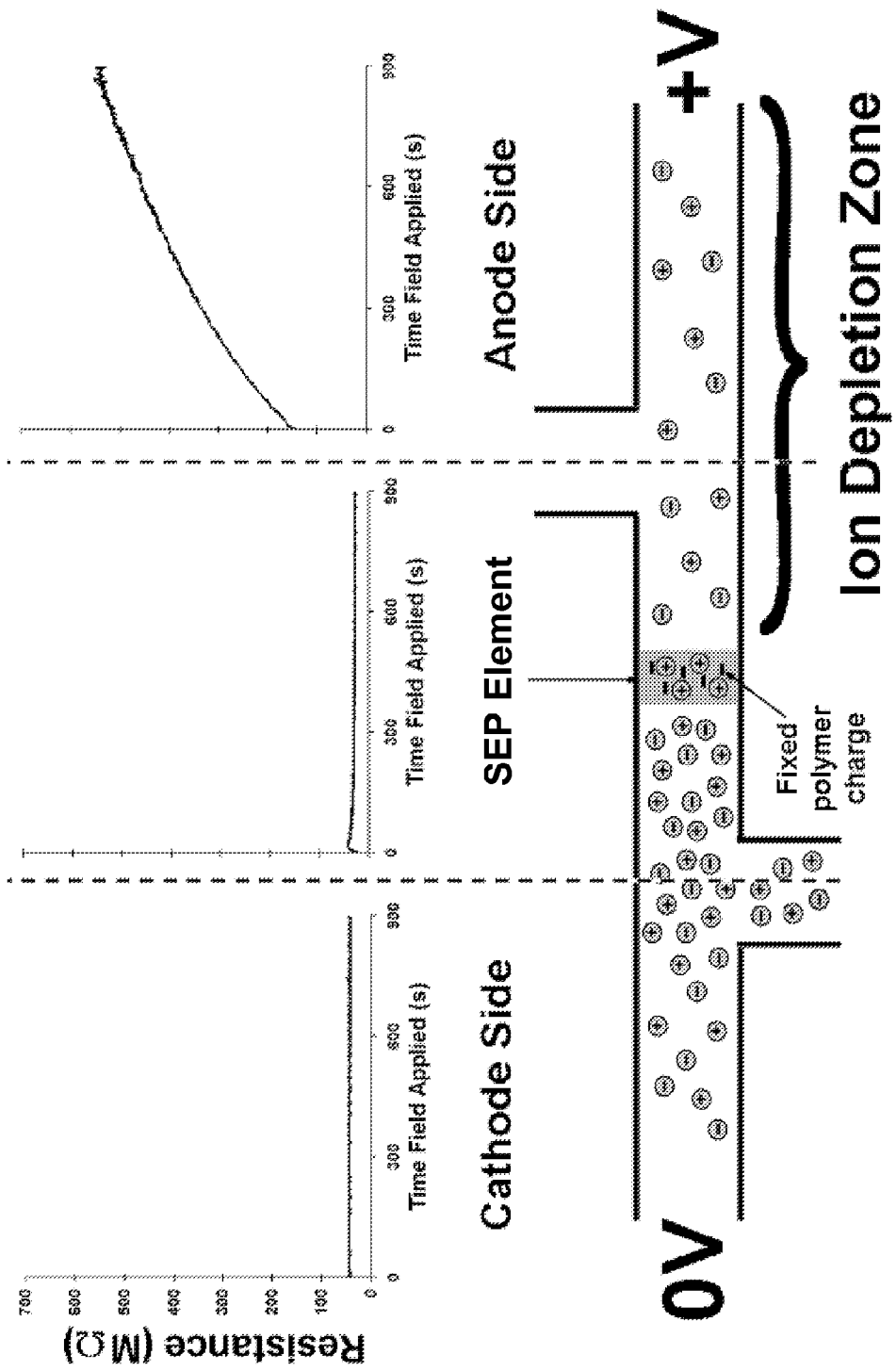

Before modifications were made to resolve concentration polarization, there were problems of irreproducible loading and separation of proteins as evidenced in FIG. 4C. A chip that was initially equilibrated overnight was subjected to consecutive replicates of a preconcentration and separation protocol (identical applied voltages and times). The current during the preconcentration step dropped over the course of these experiments with a concentration polarization induced drop in field strength on the cathode side that slowed the rate of protein loading. Thus, the total protein trapped at the SEP element dropped substantially with each test indicating that transport was reduced. The average resistance in the separation channel, measured during the separation phase, increased with consecutive testing. But there was also ion enrichment on that same side of the SEP element during each preconcentration step. Both a depletion zone in the separation channel and enrichment more immediate to the SEP element led to destacking of proteins that is also shown in FIG. 4C. The extent of protein loading and destacking was dependent on the magnitude and timing of applied fields and the dynamics of the localized gradients generated which were complicated by the reversal of fields across the SEP element and along different paths during each cycle.

Similar behavior has been reported for both cross-linked and linear polymer DNA capillary electrophoresis sequencing gels. See Bilenko et al. (2003) J. Electrophoresis 24:1176, which is herein incorporated by reference. Over the course of DNA sequencing runs, the current through the capillary has been reported to drop gradually as an ion depletion zone forms and expands within one end of the capillary. Left untreated, this effect has been shown to slow peak migration and reduce separation efficiency. The presence of large quantities of template DNA in CE experiments has also been shown to increase the propensity for ion depletion resulting in more rapid drops in current. See Figeys & Dovichi (1995) J. Chromatography A 717:113, which is herein incorporated by reference. The faster current drops are attributed to large negatively-charged DNA templates being trapped at the edge of the gel that contribute to ion selectivity.

A similar phenomenon occurred during preconcentration when SDS was added to the buffer. The increased rate of current drop (FIG. 3A) was attributed to stacking of SDS micelles at the edge of the membrane since the diameter of a pure SDS micelle is on the order of that for an SDS-protein complex (about 5.7 nm and about 6.2 nm respectively). See Samso et al. (1995) European J. of Biochem. 232:818, which is herein incorporated by reference. Further experiments with SDS below the critical micelle concentration (about a 5-fold reduction of SDS) indicated that SDS micelles, and not free SDS, contributed to the more pronounced current drop (data not shown). Based upon these observations, preconcentration with typical SDS PAGE conditions would result in concentration polarization which in turn leads to irreproducible elution times, thus requiring incorporation of steps to minimize charge polarization effects and ensure consistency.

As a result, two steps were taken to minimize concentration polarization. First, the PP element that was initially cast on both sides of the SEP element was limited to the separation side of the channel only. The channels on the preconcentration waste side of the SEP element were instead left open and were filled with buffer during experiments. Localization of the PP element to the separation channel enabled buffer replenishment from the buffer well via bulk flow (EOF or pressure driven) on the side of the SEP element having no gel. In accordance with the concentration polarization mechanism, the anodic side of the SEP element would be depleted of ions during the preconcentration step. Continual replenishment of the buffer on the anodic side served to stabilize currents during preconcentration.

Figure 4D:
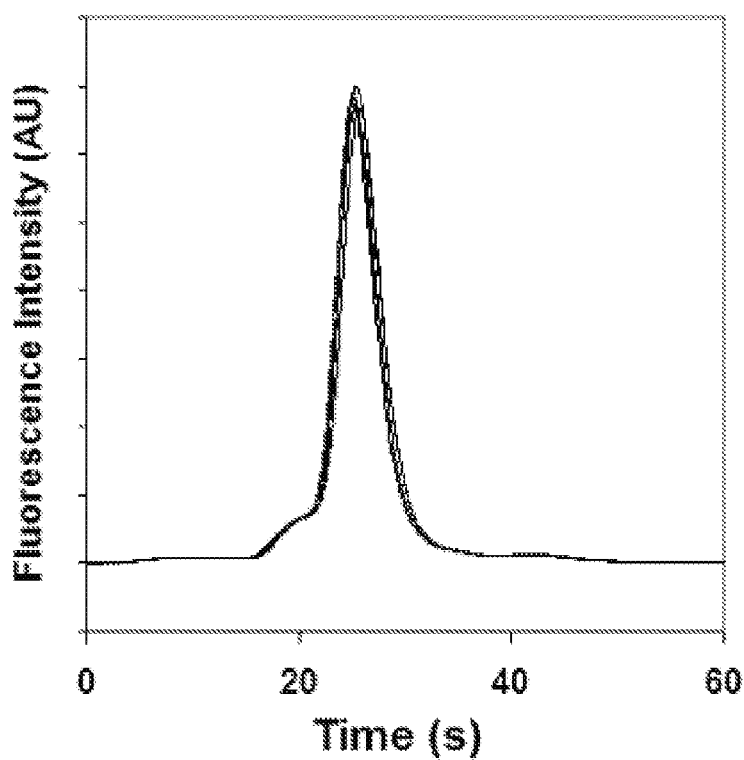
FIG. 4D is a graph showing reproducibility was dramatically improved when bypassing the SEP element during most of the separation step and when porous polymeric element was not polymerized in channels on the PW side of the SEP element (FIG. 2). Shown are 5 consecutive replicates obtained with the same preconcentration time and voltage used in FIG. 4C but with an altered elution protocol. The field was applied across the SEP for only 10 seconds and then the SEP element was electrically bypassed for the remainder of the separation.

Second, concentration polarization was minimized during the separation step by routing the electrical current so as to bypass the SEP element during the majority of the separation step. To elute protein as a sharp band, the field across the SEP element was applied for a short time (about 10 seconds) after which the SEP element was bypassed by switching the grounded electrode from B to LB. Bypassing the SEP element also proved to replenish ions depleted within the separation channel during the initial time in which the field was applied across the SEP element. For the geometry used, the peak shape of the eluted species was appreciably sharper if the duration of the applied elution field allowed the slowest migrating protein to move past the side channel (located about 100 microns away from the SEP element), prior to electrical bypass of the SEP element. Significantly improved reproducibility, FIG. 4D, was obtained with the described modified approach implemented to minimize concentration polarization. This modified approach was used in all experiments except those shown in FIGS. 4A, 4B, and 4C.

IV. Sample Loading

Two approaches, "direct loading" and "volume loading", were used to deliver proteins to the SEP element.

A. Preconcentration with Direct Loading

Figure 5A:
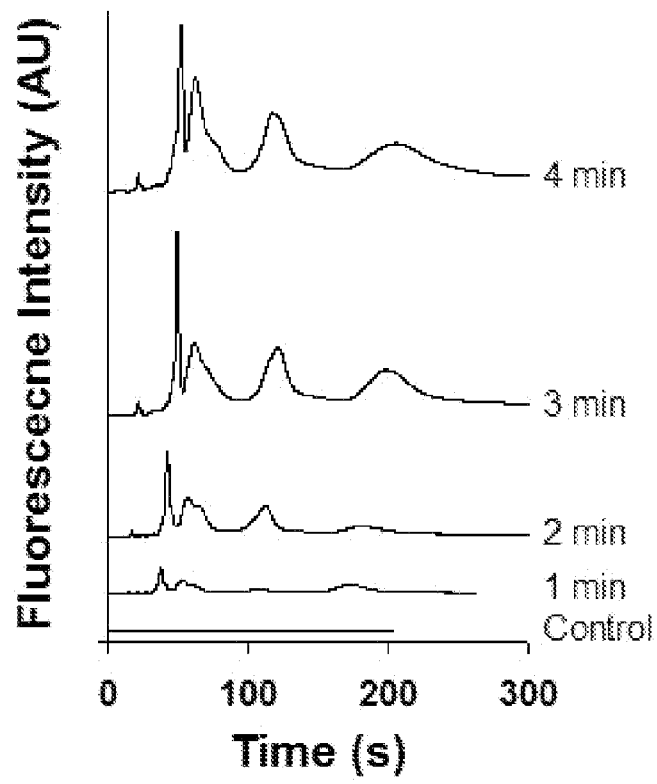
FIGS. 5A-5C shows preconcentration by direct loading of protein to the SEP element.
Figure 5B:
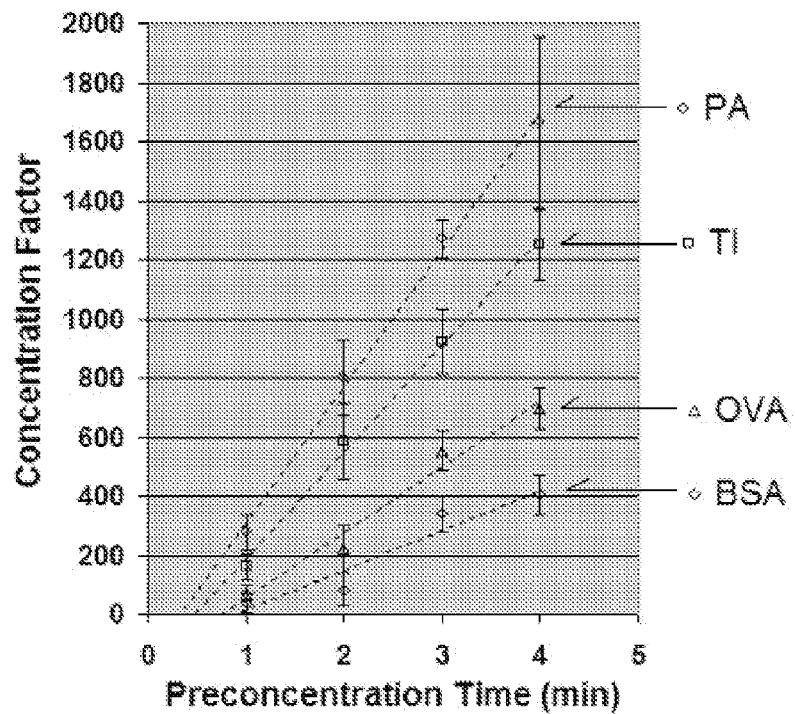

In the direct loading approach, the electric field was applied across the SEP element between S and PW reservoirs (S=ground, PW=+V). Thus, sample proteins were loaded directly from the sample well to the SEP element. FIG. 5A shows the electropherograms of protein samples separated by SDS-PAGE after 1 to 4 minutes preconcentration time. FIG. 5B shows concentration factors for BSA, PA, OVA, and TI as a function of the preconcentration time. As is shown, concentration factors with 4 minutes preconcentration ranged from 400 for BSA to well over 1,000 for the smaller proteins PA and TI. With direct loading, the concentration factor for each protein is a function of its electrophoretic mobility, the electric field strength, and time over which the field is applied. With SDS coated proteins, mobility is size dependent. Thus smaller proteins with higher mobility accumulate at the SEP element faster than larger proteins and therefore exhibit higher concentration factors with direct loading. The electropherograms therefore give a skewed representation of relative protein concentrations present in the original sample, but the data can be compensated, if desired, by normalizing by elution time for each species. Such compensation would be inaccurate if relative protein mobilities during separation were different than those during loading. For example, when a sieving gel is only present in the separation channel or if differences in sample and buffer pH caused different mobilities during loading vs. separation.

Figure 5C:
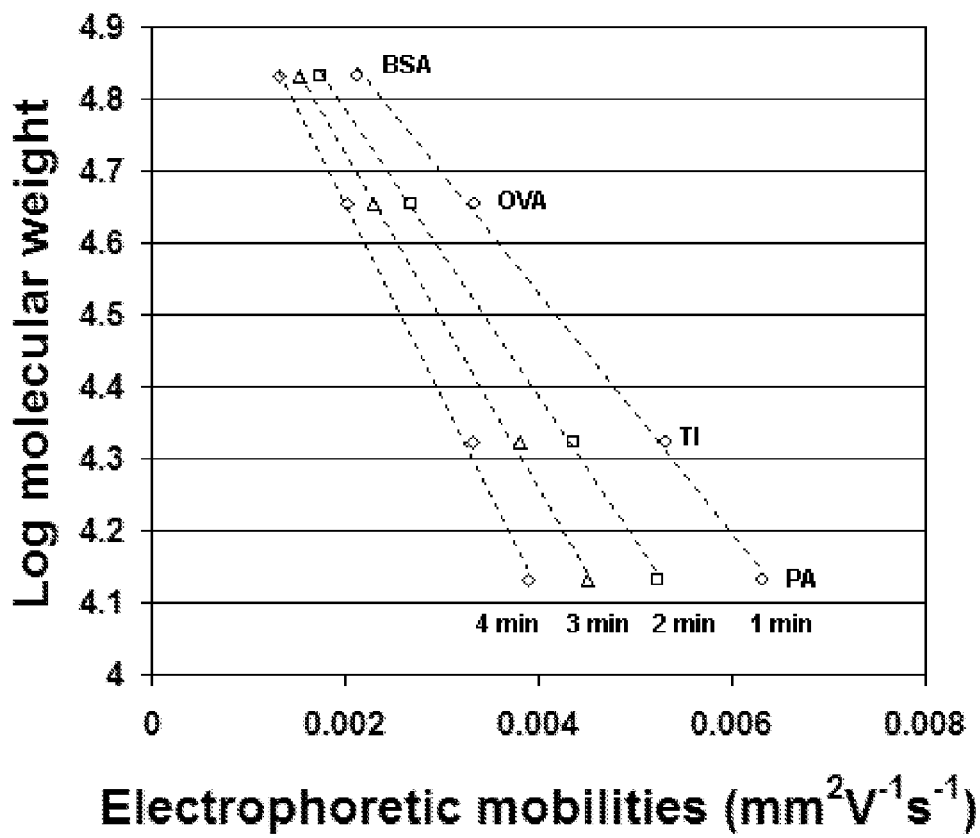

Concentration factors for each protein were roughly linear with respect to the time over which a given field strength was applied (within the time-ranges tested). However, with this direct loading approach, variations in preconcentration factors for any given time were quite high even though currents were stable. The substantial variation in concentration factors is attributed to concentration polarization effects that can affect the sample loading channel with extensive use, as the data presented in FIGS. 5A-5C were acquired from 50 separations run in immediate succession, but varied in order of preconcentration times. With long preconcentration times or continual testing, ion enrichment and associated changes in electrical resistance and pH could extend further and further into the sample loading channel.

Figure 7A:
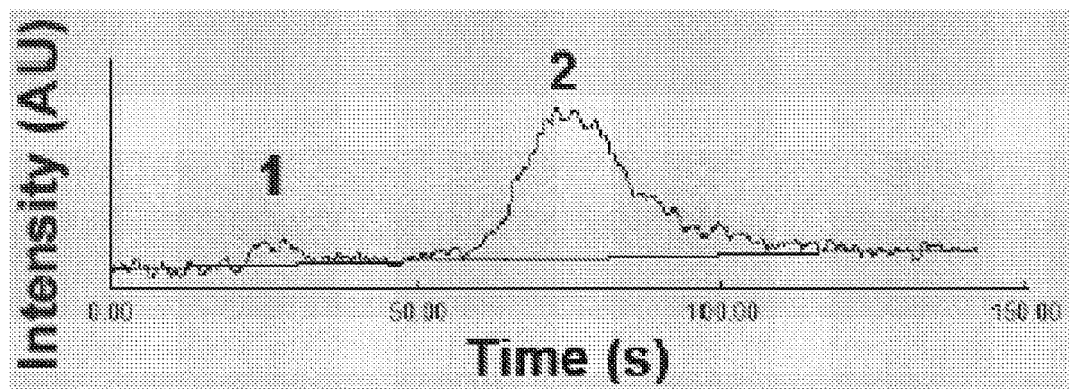
FIG. 7A shows detection of 50 fM protein after 30 minutes of preconcentration at an SEP element. The concentration factor was about 10,000 fold. Ovalbumin (1) initially at 50 fM and IgG (2) initially at 250 fM were detected under native PAGE conditions. The peak detection algorithm identified both peaks with discrimination greater than about 3× above the baseline noise. The solid line is the baseline fit.
Figure 7B:
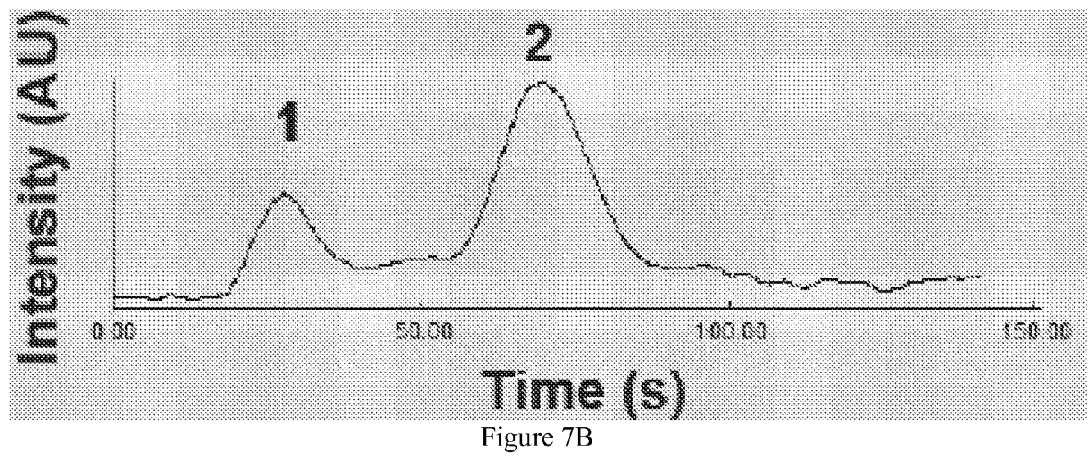
FIG. 7B shows detection of 50 fM protein with initial concentrations about 4× higher than for that showed in FIG. 7A.

As expected for SDS-PAGE, protein mobilities were found to be log-linear with molecular weight. See FIG. 5C. Therefore, a device comprising a SEP element adjacent to a PP element is useful for protein sizing applications. It was also found that with longer preconcentration times, protein mobilities were lower (similar to findings of Foote, et al. (2005) Anal. Chem. 77:57, but perhaps less pronounced) due to destacking of SDS micelles that are concentrated along with proteins which reduces separation resolution. However, for a given preconcentration time, protein mobilities and sizing capabilities with SDS-PAGE were fairly consistent. Attempts were made to limit stacking of SDS micelles by lowering the concentration of SDS in the sample below the critical micelle concentration (CMC) and then adding a bolus of SDS micelles from a second sample reservoir (containing SDS above the CMC) after sample proteins were concentrated, but lower concentration factors and large deviations in results were observed for the conditions tested. Reduced elution mobilities and shifted elution times were not apparent at these concentration factors when no SDS was present. See FIG. 6 and FIG. 7.

The detection limit with preconcentration was extended about 10,000-fold with 30 minutes of preconcentration time. Proteins were detected and resolved at concentrations as low as about 50 fM. See FIG. 7.

2. Preconcentration with Volume Loading

Figure 8B:
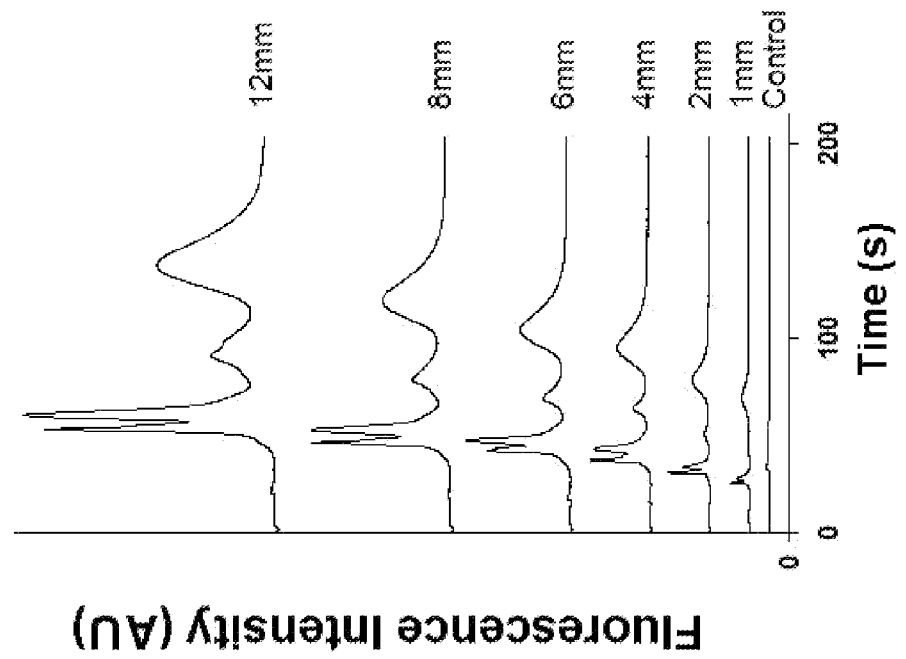
FIGS. 8A-8C show preconcentration by swept-volume loading of protein.
Figure 8A:
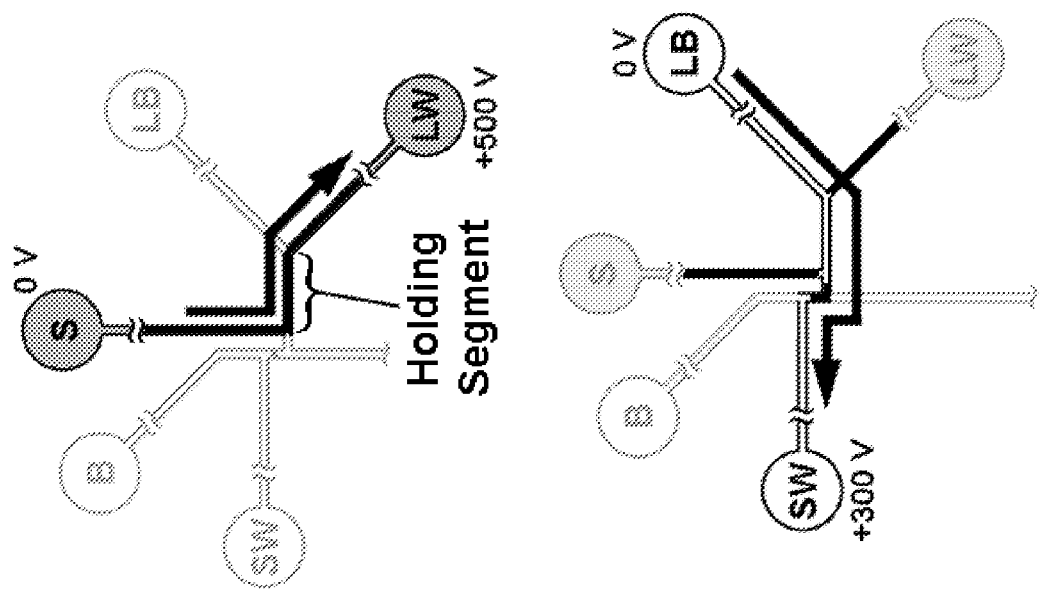

The volume loading approach is illustrated in FIG. 8A. A holding channel segment was filled with sample (analogous to a sample loop injection) by applying a field between the S and load waste (LW) reservoirs (S=ground, LW=+V). Protein was then swept from the holding segment to the SEP element by applying a field between the loading buffer (LB) and PW reservoirs (LB=ground, PW=+V). A defined volume of sample proteins were thereby concentrated at the SEP element without dependence on protein mobility. The concentration factor was then not affected by the size and net charge of proteins, changes in pH and ionic strength of the sample, or by the electrical resistance, viscosity and sieving properties of the loading channel. FIG. 8B show the electropherograms which evidence that without preconcentration, the proteins were just above the detector threshold.

Figure 8C:
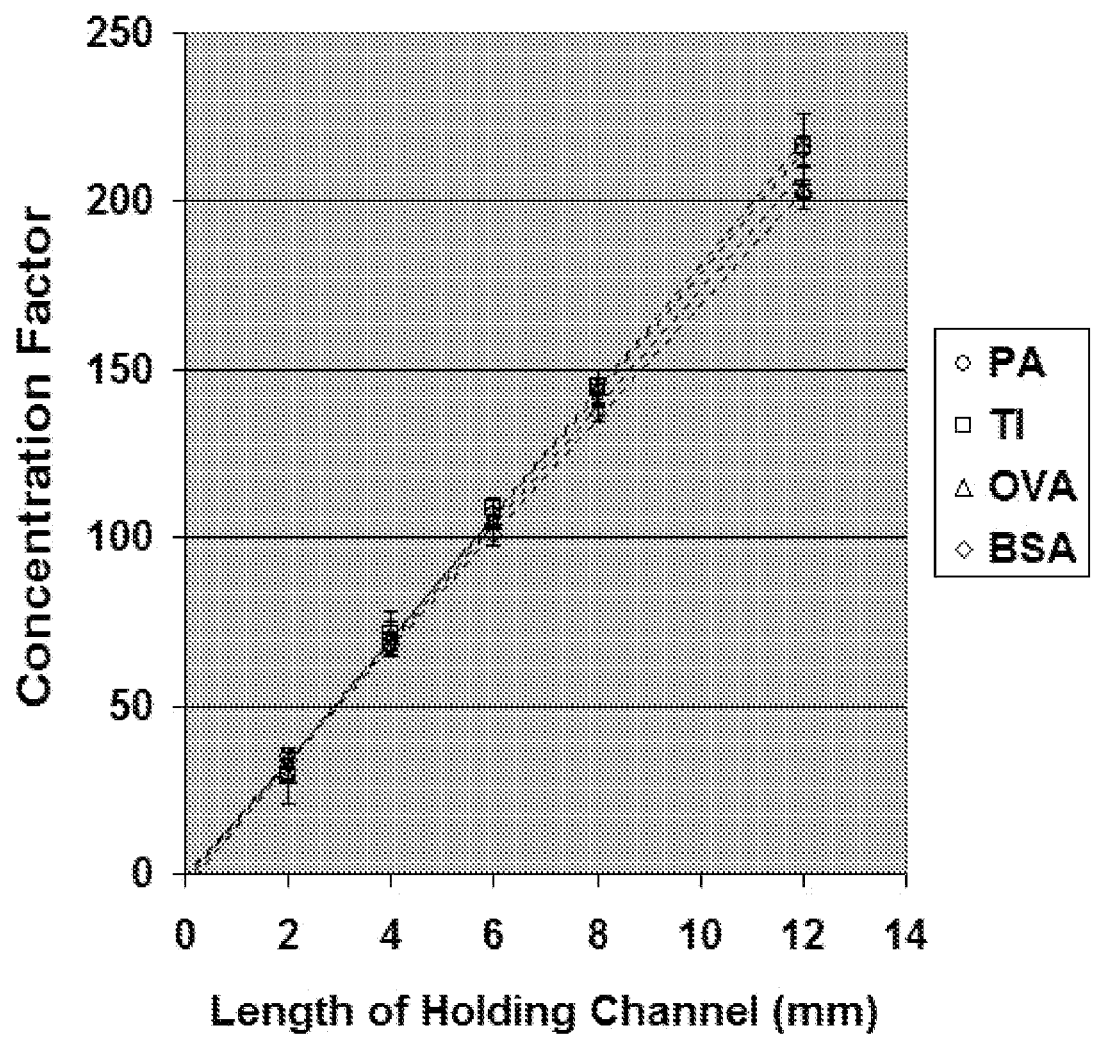

With volume loading, the observed concentration factors were proportional to the swept volume of the sample holding loop. See FIG. 8C. Sufficient time was allowed to fully sweep the holding segment of the proteins studied so that concentration factors were independent of protein mobility. Sample holding segments from about 1 mm to about 12 mm in length were loaded with sample and then swept toward the SEP element. Extra preconcentration time was also allowed to insure that the holding segment was fully swept of the largest species. The measured concentration factors were linear with swept volume, and as expected with volume loading, were equivalent for the 4 proteins showing no dependence on protein mobility. See FIG. 8C. In this case, all proteins were concentrated greater than about 200-fold within 8 minutes. The volume loading method requires time to fill the holding segment with sample before drawing proteins toward the SEP element, making the approach slower than that of direct loading. With the volume loading method, the standard deviations on the estimated concentration factors were lower than with the direct loading method (compare with FIG. 5). The reduced variability in concentration factors was attributed to lower susceptibility to concentration polarization effects. With a fixed material volume that is fully swept to the SEP element, net protein transfer is unaffected by concentration polarization induced changes in the rate of material transfer.

In contrast to the direct loading method, extension of the enrichment concentration polarization boundary layer along the path of loaded sample can be fully removed with the periodic flushing of this path during the SEP element bypass step, i.e. loading the sample fresh from the sample reservoir through the sample holding microchannel to load waste by either flow or electrophoresis to clear the sample holding microchannel of ion accumulation or depletion.

3. Other Loading Considerations

Although electrophoretic methods known in the art were used to place a sample comprising polypeptides (as the analytes) near the upstream side of the SEP element, other methods known in the art for introducing a sample to a microchannel may be employed.

In some embodiments, sample loading may be accelerated by combining flow by gravity, syringe pumps, electroosmosis, and the like with electrophoresis to deliver analyte to the SEP element. The flow may deliver analyte either adjacent to or near the upstream side of the SEP element and the electric field may be applied across the flow or a portion thereof and the SEP element to isolate and trap or filter molecules from the flowing solution at the SEP element. Net transfer of mass is then a function of both the flow velocity and electrophoretic mobility of molecules. For trapping of analyte at the SEP element, the preferred embodiment would prevent flow induced loss of molecules from the SEP element. This can be accomplished by using slow flow rates, high fields or both such that the electrophoretic forces holding particles at the SEP element dominate over flow. This can further be prevented by increasing flow resistance at or near the face of the SEP element with narrow access channels. The narrow access channels can be formed by shaping the SEP element such that molecules are trapped within narrow recesses having much higher flow resistance than the adjacent flow channel or by placing the SEP element so that it is recessed within a narrow device channel that intersects with a larger main flow channel.

The combination of flow and electrophoretic loading may be used to rapidly dialyze or remove small particles from a solution. In this combination, excluded molecules are not trapped at the SEP element, but continue traveling within the flow stream that passes by, near, or adjacent to as the SEP element will block flow and there will be little to no flow through the SEP element, but only electrophoresis or diffusion of molecules through the SEP element. The flow stream will flow near or adjacent to the surface of the SEP element and each molecule in the solution will do one of the following (1) continue flowing in the solution, (2) become trapped at or adjacent to the surface of the SEP element, (3) pass through the SEP element by electrophoresis, or (4) become trapped within the SEP element. With this configuration, flow forces are configured to dominate over electrophoretic trapping forces. Larger particles are thereby retained within the flowing solution while small molecules are rapidly removed or exchanged (buffer exchange) by electrophoresis through the SEP element. The size cutoff of molecule retention is determined by the SEP element cutoff. This is analogous to dialysis, however, the rate of dialysis is assisted by the electric field.

Figure 9:
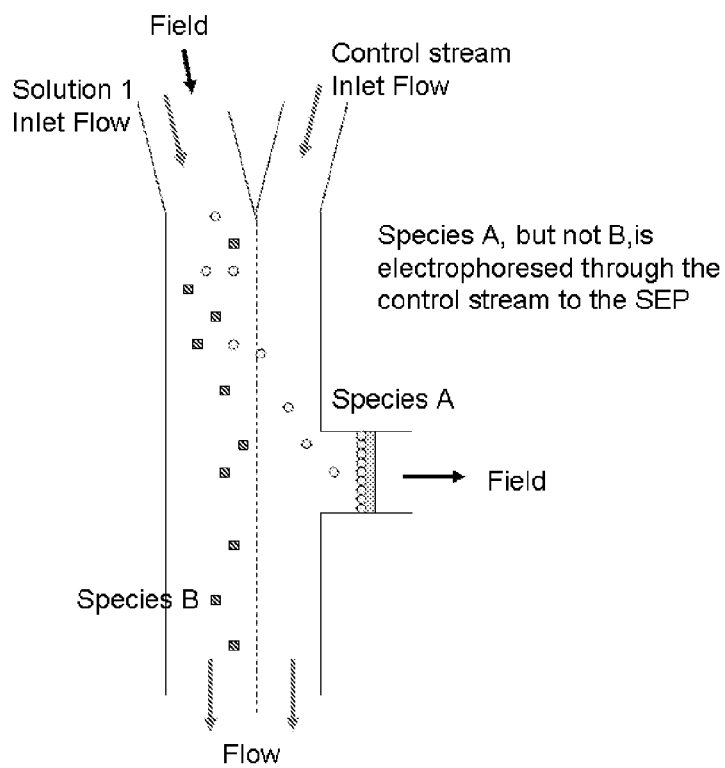
FIG. 9 shows a processing area having a control stream in an area adjacent to an SEP element that separates a sample stream from an SEP element.

Loading may be further controlled by manipulating properties of the sample either far upstream or adjacent to the SEP element. Properties that may be altered include ionic strength, pH and viscosity. Lowering ionic strength or decreasing viscosity can increase the electrophoretic loading rate. Adjusting pH can change the rate and direction of loading for different molecular species. pH adjustments can therefore be used for selective trapping, filtration, removal, and the like. In one embodiment, loading can be controlled by delivering the analyte solution under laminar flow conditions adjacent to a second laminar flow stream (the control stream) near the SEP element. The control stream can be in any orientation with respect to the analyte stream and the SEP element, but the preferred embodiment is to have the control stream oriented between the analyte stream and the SEP element so that all analyte reaching the SEP element must pass through the control stream by electrophoresis. The control stream determines the extraction or addition of species based on its pH, dimensions, conductivity, viscosity, and the like. For example, a control stream with a low pH and field applied as shown in FIG. 9 would only permit the electrophoretic transport of analytes having an isoelectric point lower than the pH of the control stream.

In some preferred embodiments, the control stream is narrow in the dimension separating the analyte stream from the SEP element so that electrophoretic transport of analyte across stream lines of the flow is rapid.

V. Device Components and Architectures

The methods and devices of the present invention may employ other components known and used in the micro- and nanofluidic arts, including manifolds, interfaces, optics, electronics, filters, sensors, pumps, valves, material coatings, and the like.

The methods and devices of the present invention may also employ a membrane such as that described in U.S. Patent Publication No. 20040084370, which is herein incorporated by reference. In some embodiments, the methods and devices may employ at least one chamber or reservoir wherein the sample to be tested can be processed or chemically modified prior to being separated or analyzed. For example, a chamber or reservoir may contain a label for the analyte to be analyzed that is released into an area when the sample comprising the analyte is present. Alternatively, the sample to be analyzed may pass through the chamber or reservoir that contains the label. In some embodiments, the methods and devices employ at least one chamber that contains reagents, such as buffers and enzymes, which are used in the operation of the device or conduct the given assay or method.

The devices of the present invention may have one or more microchannels attached to at least one loading structure. For example, the device of the present invention may comprise several microchannels attached to a single loading structure. One microchannel may be further separated into more than one microchannel to form a complex conformation of multiple microchannels having a single loading structure. The devices may comprise two or more microchannels with different polymeric elements of different properties. The devices also contain electrodes to provide a desired field or current.

In some embodiments, the devices of the present invention contain manifolds in which a wafer can be sandwiched. Such devices may be fabricated using methods known in the art. Specifically, fluidic reservoirs are fabricated from a single block of ULTEM™ polymer (GE Plastics, available from various commercial vendors) or fabricated as individual reservoirs, which can accommodate up to about 1.5 ml of buffer solutions. The electrical connection between the power supplies is facilitated by an electrode plate outfitted with spring loaded electrodes to make contact to fluid electrodes which extend into the buffer solutions. The bottom of these reservoirs are sealed with a threaded septum seal and a fluidic connection to the manifold is formed using methods known in the art.

Suitable light sources include various lamps and lasers such as a mercury lamp, longwave WV lamp, He—Ne laser, an argon ion laser, and the like. Preferred light sources are those which have a wavelength of about 320 to about 800 nm. In some preferred embodiments, a UV source is used to polymerize a UV photopolymerizeable gel. One skilled in the art may readily select an appropriate light source based upon the chemistry of the polymer to be affected by the source.

The devices according to the present invention may be assembled using methods known in the art. For example, microchannels are etched into a flat wafer, such as glass, using methods known in the art. Then a second wafer having holes is obtained and the holes of the second glass wafer are aligned with the end of channels in the first wafer using methods known in the art. The two wafers are aligned and bonded using methods known in the art, including thermal, anodical, or compression techniques. Reservoirs are attached on top of the holes. In some preferred embodiments, the reservoirs are attached by inserting thin glass or plastic vials with or without caps into the holes and then fixing the vials using a suitable glue or adhesive such as a UV-curable epoxy. In other preferred embodiments, plastic fittings are fixed on top of the holes using a suitable glue or adhesive such as a UV-curable epoxy. The fittings have holes through their centers and the bottoms of the fittings are aligned with the holes in the chip before fixing the fittings to the wafer. Then on the opposite sides of the holes (the sides opposite to having the fittings of vials affixed thereto), the holes are machined or manufactured such that a second piece, such as a plastic piece, may be affixed thereto. In preferred embodiments, the opposite sides of the holes have threads machined so that another piece may be screwed into the hole.

VI. Multiple Polymeric Elements

The methods and devices described herein may employ either a single SEP element or multiple SEP elements having the same or different properties, e.g. different pore size. Multiple SEP elements may be implemented for processing in a serial or parallel fashion. As provided herein, an "array" of SEP elements, PP elements, or both refer to two or more SEP elements or PP elements provided in a microfluidic device in a given pattern.

In serial fashion, SEP elements may be designed such that an analyte passes through one SEP element but is excluded by a second or subsequent SEP element. Alternatively, an analyte may be transferred from one SEP element to a successive SEP element by trapping and then eluting components using methods known in the art, e.g. by changing the field orientation. The electric field can be applied in either direction across the SEP element such that positive or negatively charged analytes can be directed toward or away from the SEP element. The field may also be applied in one direction and then reversed. The pH of solutions adjacent to the SEP element and on any side of the SEP element can also be manipulated by flow, diffusion, electrochemistry, and the like to further control the direction of analyte electrophoresis.

For example, an analyte may be directed to the SEP element at one pH and trapped followed by a change in pH of the surrounding solution (lowered or increased) until the pH at the SEP element is either above or below the isoelectric point of the analyte to selectively initiate redirection of the analyte without changing the field. Gradually changing pH at the SEP element allows selective redirection of different molecules in a stepwise manner.

Multiple SEP elements having different physical properties (pore size, charge, and the like) may be combined with microfluidic channels to enable selection of specific sample fractions for further analysis or collection. For example, tuning of pore size in serial SEPs (consecutively arranged) allows extraction of analytes that pass through a first SEP, but are excluded by a subsequent SEP. In one simple embodiment, larger and smaller analytes would be eliminated from the collected sample fraction using serial SEPs.

Combinations of SEP elements and PP elements could be used to perform any number of preparative and analytical steps. An additional sample would entail sample pre-processing (concentration, filtration) at an SEP element followed by sizing in a PP element, with subsequent size exclusion functionality at an SEP element for selection of a particular molecular weight analyte (possibly in a side channel). Sized fractions trapped at the SEP element could then be mixed with fluorescently-labeled immunoreagents (antibodies, aptamers, and the like) and subsequently immunoassayed in a second PP element for positive identification of the selected analyte fraction.

In some embodiments, multiple SEP elements and other integrated analysis gels known in the art, including a PP element disclosed herein, may fabricated within a single device according to the present invention in a desired arrangement or array, e.g. in parallel or serial format.

Figure 10A:
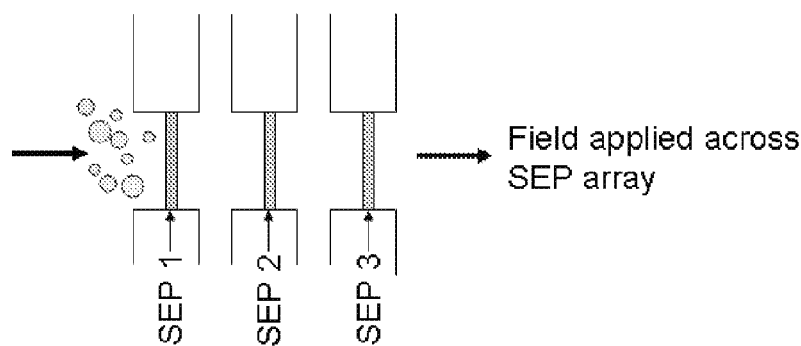
FIG. 10A shows an array of three SEP elements with SEP-1 having coarse pores, SEP-2 having medium size pores, and SEP-1 having fine pores.
Figure 10B:
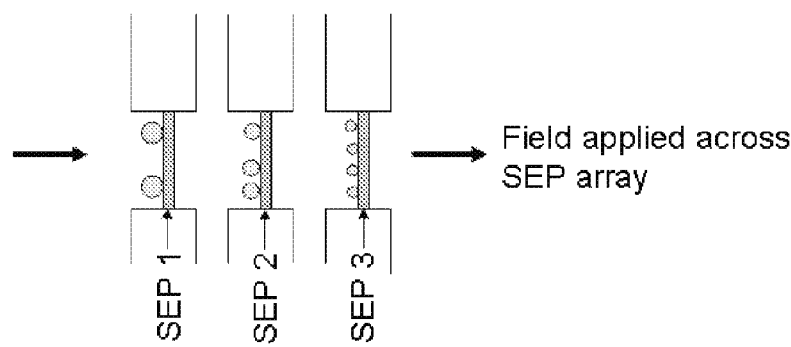
FIG. 10B shows analytes of different sizes being trapped at the three SEP elements of FIG. 10A when a field is applied.

For example, FIG. 10A shows an array of three SEP elements where the first SEP element (1) has coarse pores, the second SEP element (2) has medium size pores and the third SEP element (3) has fine pore size would result in large species being trapped at the first SEP element, intermediate size species at the second SEP element. As shown in FIG. 10B, a field applied across the SEP array results in the small species being trapped at the third SEP element. Different analytes in a sample may then be fractionated based on their relative sizes and then analyzed. For example, an intermediate size protein may be purified from proteins that are smaller or larger than the intermediate size protein in a sample by tailoring the pore sizes of an array of at least two SEP elements having at least two different pore sizes. The SEP element having a pore size which would trap the intermediate size protein would be placed after an SEP element having a larger pore size. A third SEP element having a pore size smaller than the SEP having the intermediate pore size may be placed after the intermediate SEP element, but it is not necessary as larger proteins would be trapped and removed at the first SEP element, intermediate proteins would be trapped at the second SEP element, and smaller proteins would pass through the second SEP element which may be trapped at a third SEP element or not.

In some embodiments, one or more PP elements may be integrated with one or more SEP elements of an array of SEP elements to facilitate analysis of fractions collected at each SEP element. For example, a large protein fraction can be separated and analyzed within a first PP element contiguous with the first SEP element. The medium size protein fraction can be separated and analyzed with a PP element fabricated contiguous with the second SEP element, etc. The PP elements can be tailored for optimal separation of each fraction using methods known in the art. For example, a lower percent acrylamide gel can be used to separate large proteins and higher percentage acrylamide gel for small proteins.

Figure 11A:
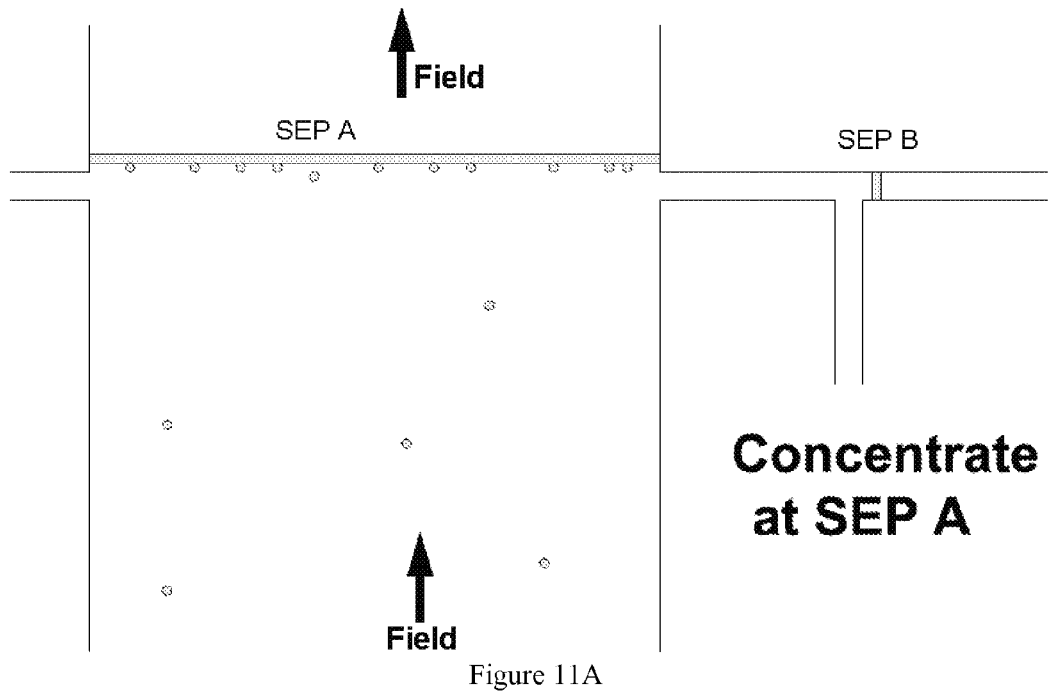
FIG. 11A and FIG. 11B are schematics showing faster processing of sample with multiple SEP stages having different cross-sectional area.

The SEP elements of the present invention may be readily arranged by those skilled in the art in order to provide faster loading and preconcentration. For example, the cross-sectional area of the SEP element in the plane perpendicular to the applied field may be increased. By using multiple SEP elements where each SEP element has a larger cross-sectional area than the next, a faster concentration rates can be achieved at each SEP element as compared to that of a single SEP element. See e.g. FIGS. 11A and 11B. FIG. 11A shows two SEP elements in a microchannel. The pore sizes of the two SEP elements may be the same or different.

Figure 11B:
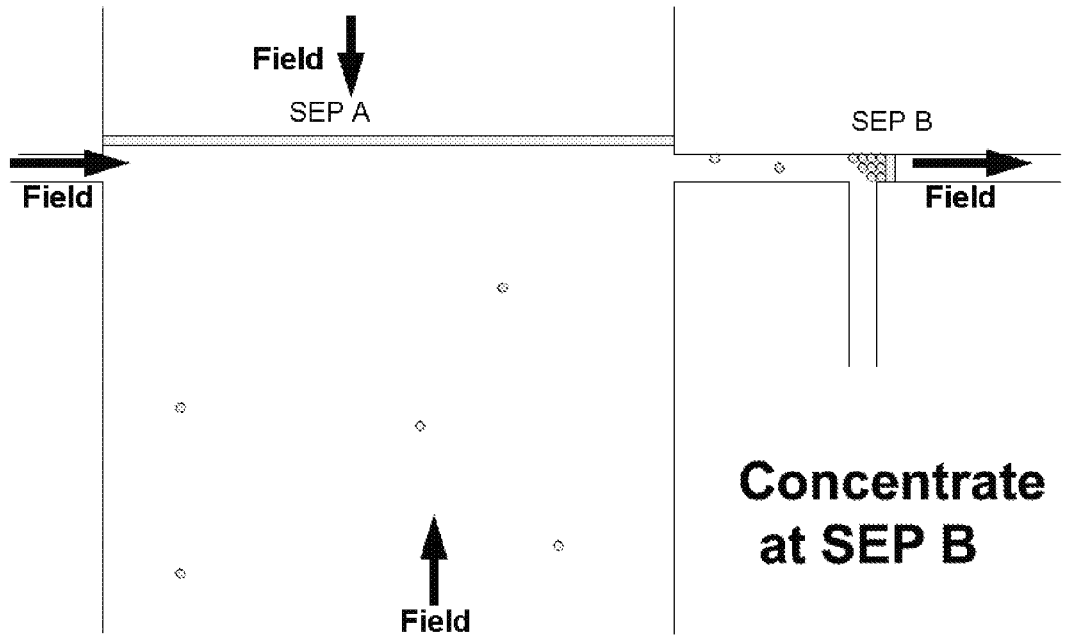

Analytes may be concentrated at an SEP element for a given time as provided in FIG. 11A and then the concentrated analytes may be further concentrated at a subsequent SEP element (having a smaller cross-sectional area than the previous SEP element) for a time shorter than the previous time as provided in FIG. 11B. Instead of the linear rate of concentration observed with a single SEP element, the rate of concentration for multiple SEP elements would follow a power law of the type, $r \sim r_o A^N$, where $r_o$ is the maximum rate for one SEP element, A is the ratio of cross-sectional areas of successive SEP elements, and N is the number of SEP elements.

To illustrate this concept, consider a device comprising three SEP elements where the cross-sectional area of the first SEP element is 10 times larger than the second and the second SEP element is 10 times larger than the third SEP element, the rate of concentration would be $10^3$ or 1,000 times faster than that obtained with a single stage having a cross-sectional area that is substantially equivalent to the first SEP element in the 3-SEP system. An added advantage of employing multiple SEP elements is that concentration polarization type effects are dramatically decreased as there is less time for ion depletion accumulation effects to build up and such effects would be dispersed over multiple SEP elements.

In some embodiments, the last SEP element in a series of SEP elements is preferably located in an area of a given device which is suitable for further processing or analysis and a length scale suited for the processing or analysis. For example, concentrating sample 1,000-fold may be desired. If, however, a sample is concentrated 1,000-fold with an SEP element having a length scale 100-fold smaller than that of the detector or processing/analysis channel it is delivered to, then the advantage at the processing/analysis stage would likely be greatly diminished.

1. Continuous Processing

In some embodiments, an array of SEP elements may be employed to allow continuous processing of a sample. As long as a field is applied, analytes in a sample may make their way through an SEP array until trapped. Devices and methods employing an array of SEP elements which are arranged for continuous processing of a sample or multiple samples are especially useful for environmental monitoring and sampling. Specifically, samples from the environment such as water or air may be continuously or consecutively taken, assayed, concentrated simultaneously concentrated in different fractions, and the fractionated samples may be monitored either in real-time at the SEP elements or at given intervals, which may or may not be combined with downstream analysis and processing. See, for example, the arrangement of the substrate in U.S. patent application Ser. No. 11/076,971, which is herein incorporated by reference, for batch and continuous flow. Thus, similar to the substrate, the SEP elements of the present invention may be arranged transverse to the flow of a fluid sample, normal to or substantially aligned with the flow of the fluid sample, or at an angle, e.g. about 80 degrees to about 10 degrees incident to the flow of the fluid sample.

2. Concentration Focusing

Figure 12:
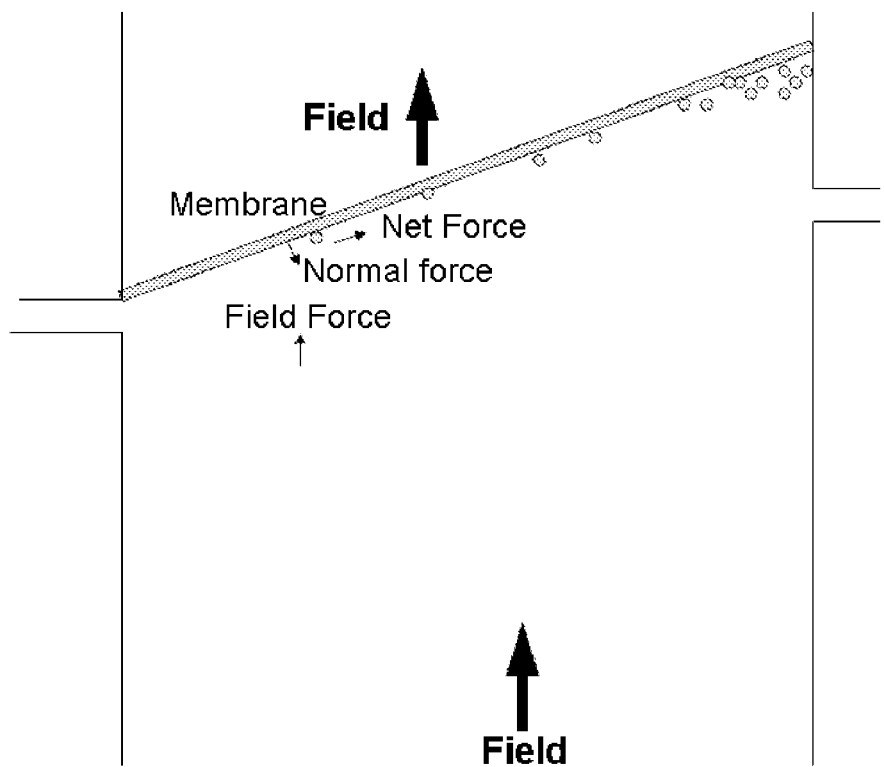
FIG. 12 is a schematic showing an SEP element with an orientation at an angle to applied electric field. This orientation drives concentrated species to a point rather than uniformly across the SEP element.

The shape and position of an SEP element may be readily optimized for a given application or condition, including integrated analysis, integrated processing volume, analysis zone, patterned analysis surface, flowing stream, separation channel, detection area, and the like. For example, an SEP element interface that is angled with respect to the field applied may be desired and optimized for preconcentrating to a point, a shape or angle that results in a tightly focused band into a separation channel, or for preventing loss of analyte by flow forces adjacent to the channel. Specifically, the orientation and shape of the SEP element surface may be modified using methods known in the art in order to optimize the location where the analytes are concentrated. See, for example, FIG. 12 which shows an SEP element at having a surface which is at an angle which is not perpendicular with the applied field direction, thereby resulting in net force which focuses the accumulation of analytes in a certain location.

Figure 13A:
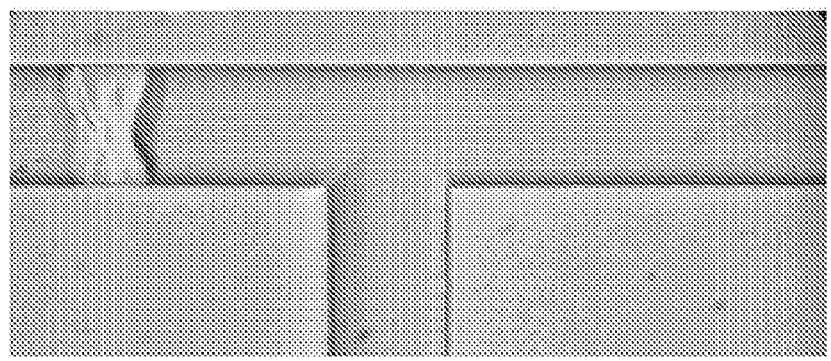
FIG. 13 shows images of a shaped SEP that was angled with respect to the field and with different resistances across the SEP face. Protein was concentrated to a point. Having protein concentrated to the center of the SEP helped prevent dispersion of concentrated protein during elution into a PP element.
Figure 13B:
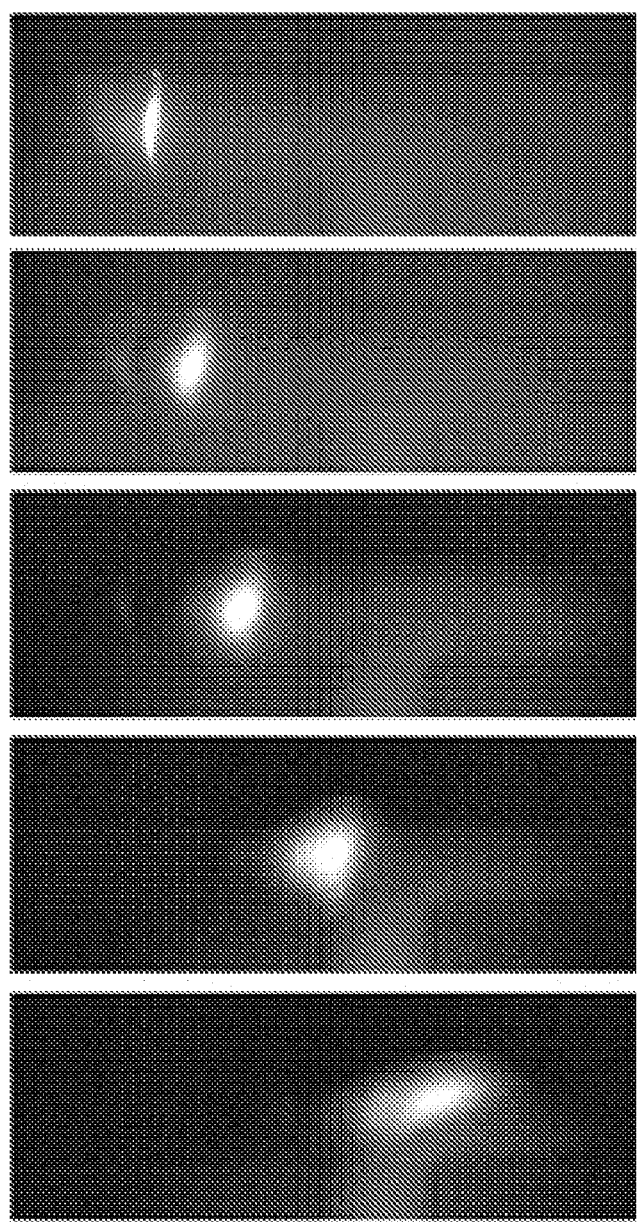

The shape of the surface of the SEP element which interfaces with the analytes determines the location where the analytes are concentrated. The location where the analytes are concentrated has an effect on the manner and location in which the analytes are further mobilized. For example, FIG. 13A shows a bright field image of an SEP element having a v-shaped interface surface. The analytes (proteins) are substantially concentrated and focused at the point in the "v". FIG. 13B shows a series of fluorescent micrographs at various times when the concentrated protein was mobilized through a PP element. As shown in FIG. 13B, the v-shaped interface surface provided a higher concentration factor in a given location and reduced dispersion during elution in the PP element as compared with the substantially planar interface as shown in FIG. 3. For example, in FIGS. 3A2 and 3B2, the protein is distributed in a tight and evenly distributed band along the entire SEP element face. In some embodiments, an SEP element may be arranged such that concentrated analytes are directed to a desired microchannel or region of a microchannel.

As shown in FIG. 13B, the microchannel intersecting with the microchannel comprising the PP element modifies the field gradient in the area where the two channels intersect. Thus, the shape of the SEP element which interfaces with the analytes may have a shape which would account for an undesired downstream change in the field gradient such that analytes of the same species move through the microchannel segment after the change in the field gradient in a manner that is consistent and similar, e.g. all of the analytes of the same species move through the microchannel in a plane that is substantially perpendicular to the length of the microchannel.

Figure 16A:
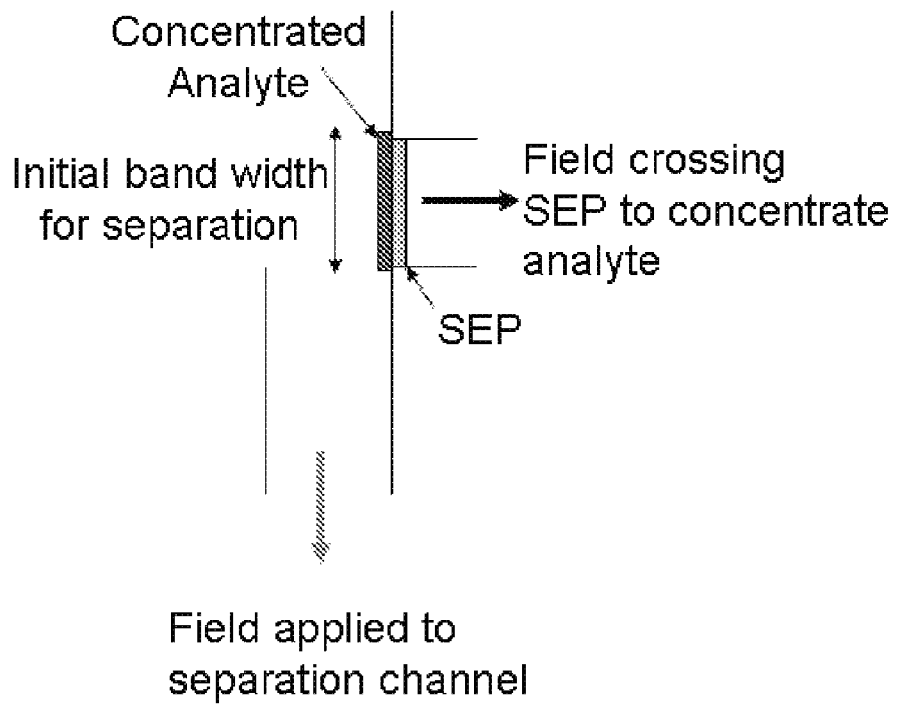
FIG. 16A shows an example where the SEP element has an interface which is in a plane parallel to the separation microchannel.
Figure 16B:
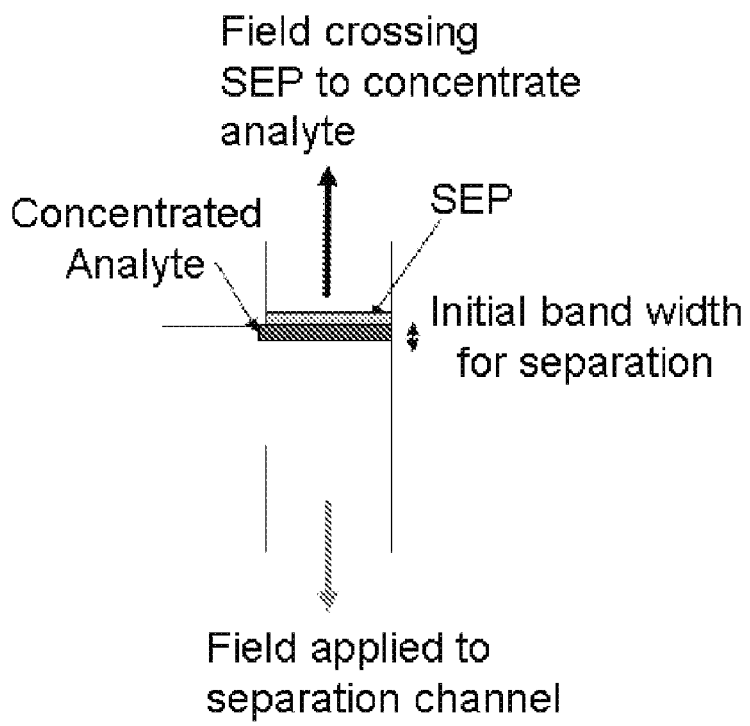
FIG. 16B shows an example where the SEP element has an interface which is in a plane that is perpendicular to the direction a field is applied to elute and separate the sample, e.g. perpendicular to the separation microchannel.

FIG. 16A shows an example where the SEP element has an interface which is in a plane parallel to the separation microchannel. FIG. 16B shows an example where the SEP element has an interface which is in a plane that is perpendicular to the direction a field is applied to elute and separate the sample, e.g. perpendicular to the separation microchannel. When the interface is in a plane that is parallel with the microchannel, the concentrated analytes are spread out along the interface surface such that the eluted band has dimensions which are initially at least as long as the length of the interface surface. When the interface is in a plane that is perpendicular with the microchannel, the eluted band is about as narrow as the confined layer of analytes, e.g. thinner than 100 micron wide channels. Thus, an SEP element having an interface in a plane that is perpendicular with the microchannel yields higher separation resolution and efficiency in polyacrylamide gel electrophoresis (PAGE) separations than an SEP element having an interface in a plane that is parallel with the microchannel. See Hatch et al. (2006) Anal. Chem. 78(14):4976-4984, which is herein incorporated by reference.

VII. Applications

In addition to loading and concentrating an analyte in a microchannel, the SEP element may be used for (1) isolating a desired analyte and removing undesired compounds and particles such as contaminants, (2) adding compounds and solutions to a sample, (3) mixing a sample, and (4) changing reaction rates.

1. Isolating Analytes and Removing Contaminants

The SEP element of the present invention may be used to isolate a desired analyte and remove undesired compounds and particles such as contaminants. In some embodiments, the desired analyte to be isolated is larger than the particles or compounds to be removed. In these situations, the SEP element has a pore size that is smaller than the analyte to be isolated, but larger than the particles or compounds to be removed such that the desired analyte is trapped at the SEP element and the contaminants pass through the pores to the other side of the SEP element.

In other embodiments, the desired analyte to be isolated is smaller than the contaminants to be removed. In these situations, the SEP element has a pore size that is larger than the analyte to be isolated, but smaller than the particles or compounds to be removed such that the contaminants are trapped at the SEP element and the desired analytes pass through the pores to the other side of the SEP element.

2. Adding Compounds and Solutions to a Sample

The SEP element of the present invention may be used to add compounds and solutions, such as reagents and buffers for a given application to a sample. For example, a compound located upstream of an SEP element is to be added to a sample that is downstream of the SEP element. The SEP element has pore sizes which allow the compound to pass through the pores to the sample. In some embodiments, the SEP element may be used to recycle and reuse or add unreacted compounds to a sample. For example, where unbound dyes and labels pass through the pores of an SEP element while dyes and labels bound to an analyte do not, the SEP element may be used to collect the unreacted reagents for adding to a subsequent sample.

3. Mixing

In some embodiments, the SEP element may be used to mix a sample or analytes with buffers, labeling chemicals, enzymes, and the like. For example, as shown in FIGS. 14A and 14B, analytes from a sample may be concentrated at the SEP element and then a reagent, such as a label, is added using methods known in the art such as electrophoretically loading to the SEP element from a separate microchannel or inlet. The reagent can either pass through or be trapped by the SEP element. In either case, the reagent and analyte are effectively mixed in the small channel volume adjacent to the SEP element.

With the label passing through the SEP element, the mixing and chemical reaction occurring at the SEP element can serve to modify the trapped analyte (e.g., for a complex between the label and analyte) and simultaneously remove unreacted reagents which may otherwise interfere with detection or downstream processing. In chemical reactions, continued addition of a reactant and removal of a reaction product can serve to increase efficiency and product yield.

Although sequential loading of solutions are preferred for mixing because of perfect overlap between electric field lines (i.e. transport paths overlap, an ideal condition for mixing) as provided in FIG. 14A, solutions may also be loaded simultaneously by fields from different channel segments or reservoirs across the SEP element as provided in FIG. 14B. For simultaneous loading, the field lines cross different sections of the SEP element, but different molecules may still mix effectively by diffusion across a short distance defined by the length scale of the SEP element.

4. Changing Rates of Reaction

Because concentrations are higher in the volume adjacent to the SEP element than in the original solution samples, increased binding and chemical reaction efficiency can be achieved at the SEP element based on the dependence of reaction equilibrium and rate constants on reagent concentration. Therefore, reactions that may not be successful by simply mixing original stock solutions or sample at any given stoichiometry, can be rendered successful by mixing of at the SEP element at optimal stoichiometric concentrations. The reaction stoichiometry may also be easily controlled by adjusting the time each reagent is loaded to the SEP element or the volume of each solution swept to the SEP element, or both without adjusting bulk solution concentrations, which is advantageous over many other mixing methods known in the art.

VIII. Multiplexing

The methods and devices of the present invention may be multiplexed with other detection methods known in the art such as UV detection, post-separation labeling, dynamic labeling methods, non-fluorescence techniques, and the like. See Liu, Y et al. (2000) Anal. Chem. 72:4608-4613; Swinney, K and D J Bornhop (2000) Electrophoresis 21:1239-1250; and Jin, L G, et al. (2001) Anal. Chem. 73:4994-4999, which are herein incorporated by reference.

The present invention also provides a means for integration and multiplexing of various unit operations based on combining SEP elements with additional, non-PPE based analysis. SEP elements would be used to prepare a sample prior to on-chip non-PPE based analyses such as protein or DNA microarray characterization or off-chip methods such as mass spectrometry.

The present invention provides a means for integration and multiplexing of various unit operations based on combining SEP elements with PP elements in a microfluidic chip. Any one of numerous combinations, comprised of multiple microchannels, could be applied to provide for post-analysis manipulation of analytes (filtering, concentrating, buffer exchange, size selection) as, for example, part of tandem analytical separations joined by SEP elements. Generically, sample preparation (concentration, filtration, buffer exchange) at an SEP element followed by bioanalytical separation (protein sizing, gel electrophoresis, chromatography) in a PP element may be joined with subsequent molecular weight based selection of analyzed analyte fractions using a second SEP element just prior to a secondary bioanalysis in a PP element having different characteristics (pore size, buffer conditions, applied electric field strengths) than the first PP element. Sample preparation operations (buffer exchange, mixing, filtration, concentration) could be combined sequentially or in parallel by routing sample fluids through multiple SEP elements either in a single channel or in multiple channels.

EXAMPLES

Polymer Formulation

Figure 17A:
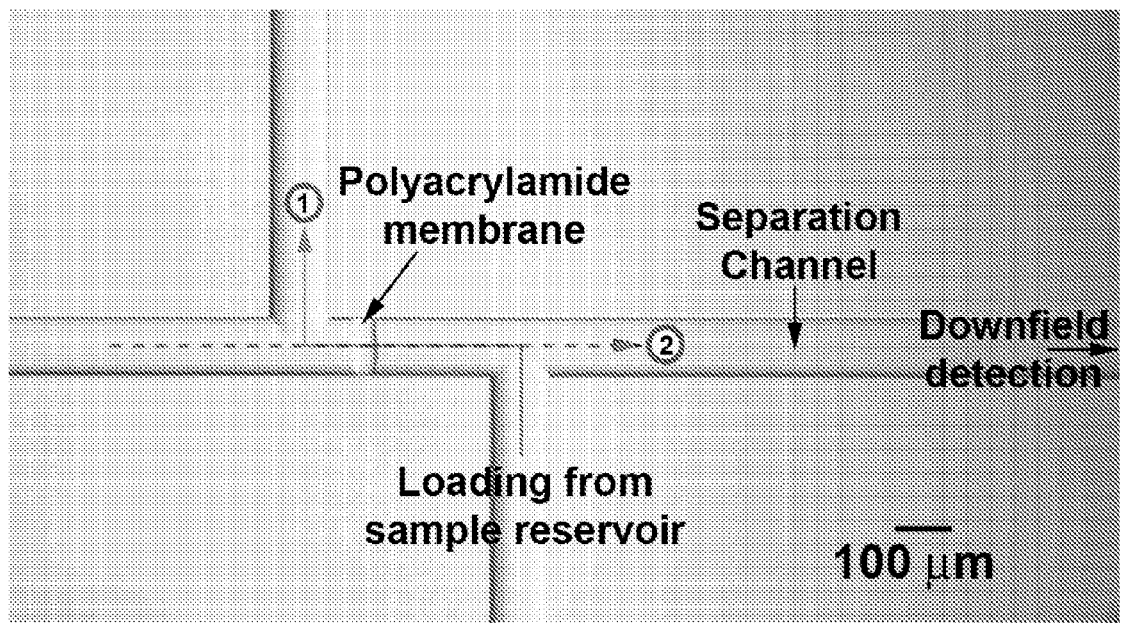
FIG. 17A shows a bright field image of a polyacrylamide SEP element in a glass microchip. Lines show direction of electric fields applied for (1) sample concentration step and (2) elution and PAGE separation. A 6% polyacrylamide sieving gel is photopolymerized in the separation channel
Figure 17B:
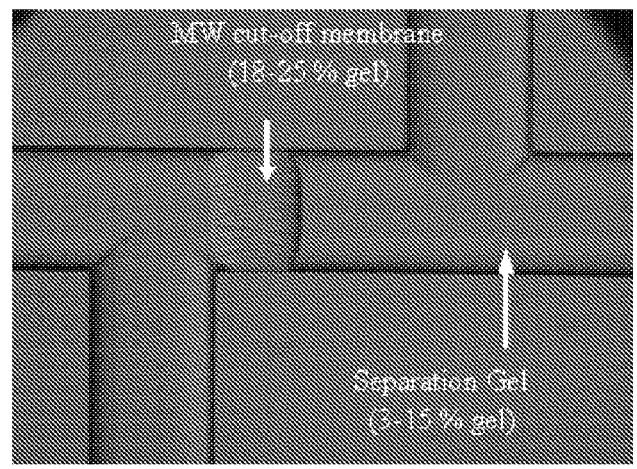
FIG. 17B shows a magnified view of an off-set "T" microchip having an in-situ polymerized SEP element and a separation gel placed therein to provide a means for integrated concentration and separation of proteins (the separation gel is invisible because it contains bigger pores that do not scatter light).
Figure 17C:
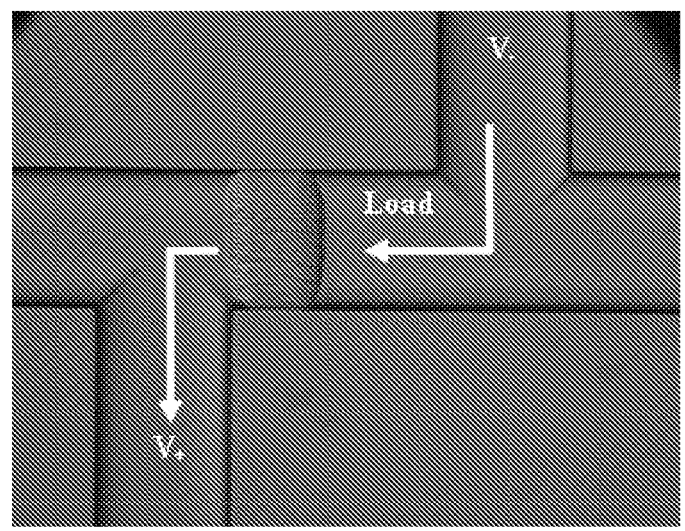
FIG. 17C shows a schematic of the process wherein a sample containing analytes is loaded by applying voltage across the membrane.
Figure 17D:
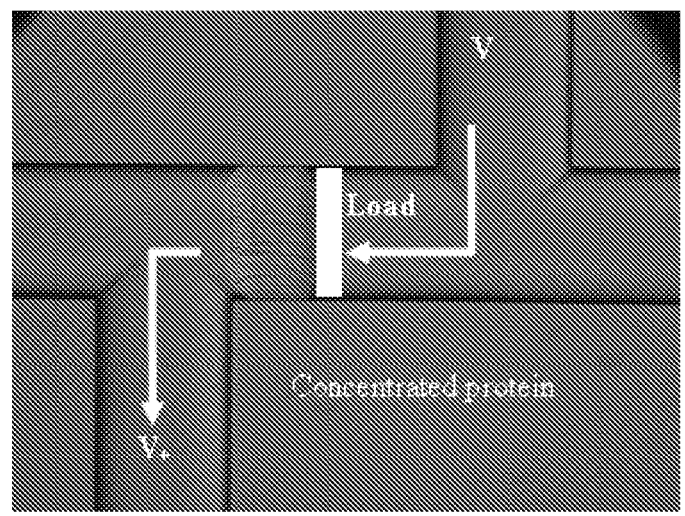
FIG. 17D shows a schematic of proteins and/or other biomolecules bigger than the pores of membrane being concentrated on the upstream side of membrane.
Figure 17E:
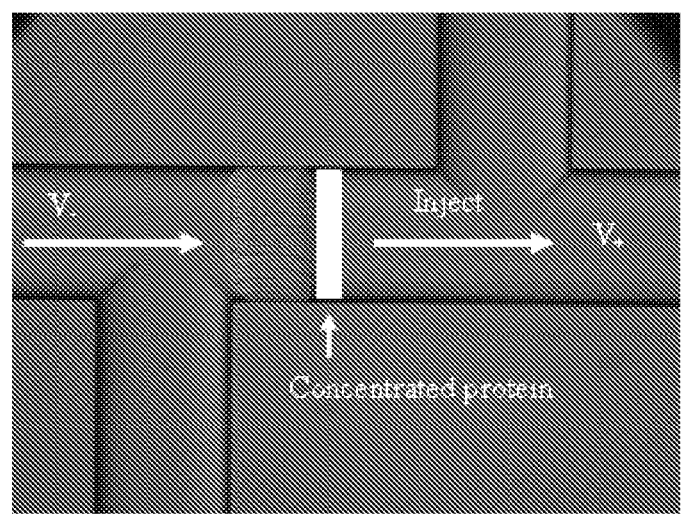
FIG. 17E shows a schematic of the process of changing the electric field direction in order to elute the prior concentrated group of molecules after obtaining the desired concentration.
Figure 17F:
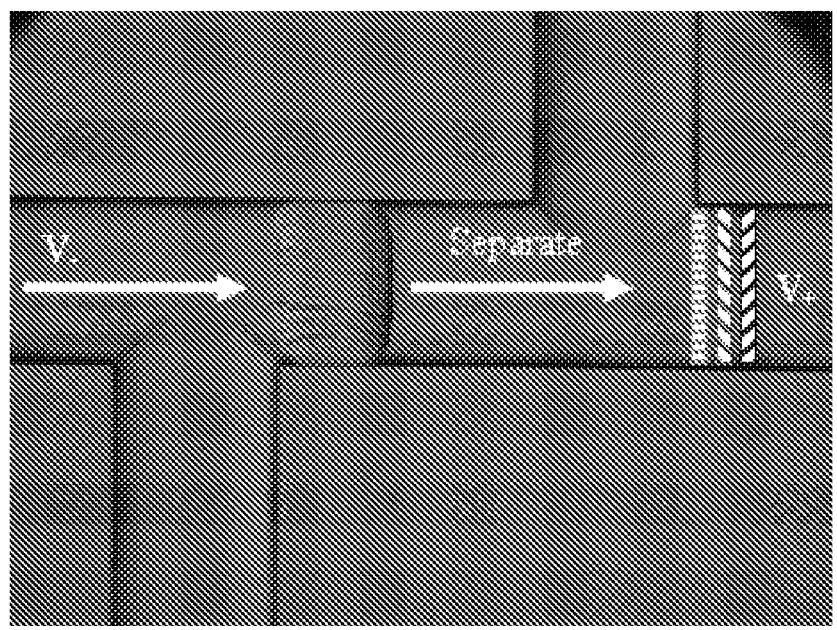
FIG. 17F shows a schematic showing the concentrated molecules being separated as they migrate through the separation gel.

With the exception of the SEP elements, glass chip fabrication was as described previously. See Herr, et al. (2005) Anal. Chem. 77(2):585-590, which is herein incorporated by reference. The etched microchannels were about 100 μm wide and about 40 μm deep. The channel surface was coated with an acrylate-terminated layer to anchor the gels. Crosslinked gels were polymerized in situ by loading solutions of acrylamide/bisacrylamide monomer containing 0.2% VA-086 photoinitiator and exposing to UV light. Narrow (about 30-50 μm) cross-linked polyacrylamide SEP elements were defined with a shaped laser beam (described by Song, et al. (2004) Anal. Chem. 76:4589-4592, which is herein incorporated by reference. Unpolymerized monomer (15-27% T) was flushed from the device and replaced with lower percentage acrylamide solution (6-8% T) that was subsequently photopolymerized to form the PP element shown in FIG. 17A. Images showing species transport behavior were taken with a digital camera and epifluorescent microscopy. Laser-induced fluorescence (LIF) was used for sensitive detection of immunoassay separations. Fields greater than about 150 V/cm were applied for preconcentrating and greater than about 350 V/cm for the separation step using programmable power supplies fabricated in-house. Commercially available monoclonal IgG antibodies were labeled with Alexafluor 647 (obtained from Molecular Probes™, a division of the Invitrogen Corporation, Carlsbad, Calif.). Patient samples were collected at the University of Michigan and stored at −40° C. until use. Tris/glycine (obtained from BioRad Laboratories, Inc., Hercules, Calif.) was the run buffer for electrophoresis.

Standard cross-shaped glass microchips were microfabricated using standard photolithography and bonding techniques; chemicals were obtained from Aldrich and used as received. To facilitate bonding between the polymeric elements and the glass surfaces, the latter were first exposed to a 5:3:2 (by volume) mixture of water, glacial acetic acid, and 3-(trimethoxysilylpropyl)acrylate for a period of 30 minutes, covalently linking the acrylate silane functionality, or "tail," to the glass surface walls and disposing the acrylate functional group toward the interior of the channel. The silane solution was made just prior to use.

The microchips were flushed with the freshly made silane solution by loading one of the via holes connected to the interior separation channels using pipette tip, while applying a vacuum to the remaining via holes and allowing capillary action to assist in solution migration. The microchip was then covered with a small glass dish (to minimize evaporation) and allowed to incubate for not more than 30 minutes total, after which the silane solution was removed by again attaching a vacuum to one or more of the via holes.

The functionalized separation channels were then rinsed twice with degassed 30% acetic acid (covering entire surface of chip), then rinsed twice with deionized water and dried thoroughly in a vacuum. A stock solution of a 22% T, 6% C acrylamide and VA-86 photoinitiator was prepared and degassed thoroughly in an Eppendorf® tube using vacuum and sonication just prior to loading the separation channels of the microchip. This mixture was then introduced into the microchip as described above and subsequently polymerize SEP element using a 12 kHz, 800 ps-pulse, frequency-tripled Nd:YAG laser and an exposure time of about 15 seconds (SEP element formation was visible with low level bright-field illumination).

Unpolymerized solution was removed by using a brief exposure to vacuum and by thoroughly flushing a quantity of the acrylamide solution required for eventually forming the PP element (typically 3-15% T, 2.5% C acrylamide) through the separation channels and the SEP element. The microchip was then exposed for 10 minutes in a XL 1500 Spectrolinker™ (available from the Spectronics Corporation, Westbury, N.Y.) ultraviolet ("UV") oven operating at 365 nm. Polymerized microchips thus formed were stored in a buffer-filled container. Gels up to 27% T, 9% C were tested although most experiments were with 22% T, 6% C acrylamide.

Example 1

On-Chip Mixing at the SEP Element

Mixing of sample with buffer and reagents is a vital component of most integrated microfluidic processes. It is also a challenge for which a number of novel approaches have been employed. Some of the key factors that define the effectiveness of a mixer are the (i) time and (ii) space required for mixing and (iii) the complexity of device fabrication added by the mixing element. Also relevant is whether the mixing depends on the size of the species being mixed or other properties of the sample such as viscosity or pH.

The processing area adjacent to an SEP element serves as a suitable mixer in terms of device space used for mixing and time required. In the assays tested, proteins from solution 1 can be trapped at the SEP element followed by proteins from solution 2. The components are fully mixed at the SEP element as soon as they are trapped. This could easily be extended to additional solutions. Another advantage is that the ratio of components from each solution that are mixed are easily controlled by the duration and strength of the field (or swept volume) applied. There does not have to be a change in mixing time, channel geometries or mixer length common with many approaches. At the SEP element, the electric field lines are perfectly overlapping leading to ideal conditions for mixing (perfect overlap of fluid components) giving incredibly rapid mixing, even for large, slowly diffusing molecules.

For immunoassay testing, antibody was first trapped at the SEP element followed by loading of buffer or saliva samples that contained specific antigen. The perfect mixing at the SEP element resulted in rapid binding of antigen and antibody. In all cases tested, binding was completed during the normal course of loading (about 60 seconds or more for the assays tested) and compared well with control experiments where reagents were premixed. No extra time (beyond the already necessary loading step) was required for mixing or to allow binding, nor was there a need for extra channel segments or chip real estate. An additional advantage can be expected by combining mixing with preconcentration for applications where molecular binding interactions are important. This is because the extent of binding is concentration dependent, with higher concentrations resulting in greater extent of binding. For immunoassays where native concentrations of antigen are low, it can be difficult to overcome the limitations of antibody affinity. Preconcentration helps alleviate this problem by raising concentrations to levels where appreciable binding will occur. In most applications, the sample is diluted in each mixing step, whereas with the size exclusion SEP element, concentrated sample can be exposed to multiple additions of other components and have the buffer ions exchanged without reduction.

One example of mixing has been achieved with a device arrangement shown in FIG. 14. Fluorescently labeled monoclonal IgG specific to MMP-8 at an original concentration of 500 pM in 1× tris glycine buffer was loaded from the left channel as shown in FIG. 14A1 for duration of 1 minute at a field of 100 V/cm to trap and concentrate antibody at the SEP element. The channel dimensions and SEP fabrication were the same as described by Hatch et al. (2006) Anal. Chem. 78(14):4976-4984, which is herein incorporated by reference. The field was then immediately switched as shown in FIG. 14A2 so that antigen (MMP-8) contained in a second fluid sample was electrophoretically trapped and concentrated at the SEP element. The antigen was loaded for different times ranging from 1 to 8 minutes at a field of 50 V/cm. While the antigen was being loaded, mixing and binding between antigen and already trapped IgG occurred at the SEP element; no mixing element or off-chip mixing was required. This allowed very small amounts of IgG reagent to be used for each sample that was tested. The concentrated mixture modified by binding between antibody and antigen was also separated and analyzed by having a third channel segment with a PP element.

Example 2

Preconcentration Followed by SDS-PAGE of Proteins in a Microchip

SDS-PAGE is a commonly used protein separation technique for protein size determination and expression profiling. Only more abundant proteins are detectable with standard methods leaving out many important low-abundance proteins from analysis. Using an integrated SEP element and cross-linked PP element for preconcentration and separation of proteins, greater than about a 1,000-fold improvement can be achieved without loss of separation resolution. See Hatch et al. (2006) Anal. Chem. 78(14):4976-4984, which is herein incorporated by reference.

Figure 18A:
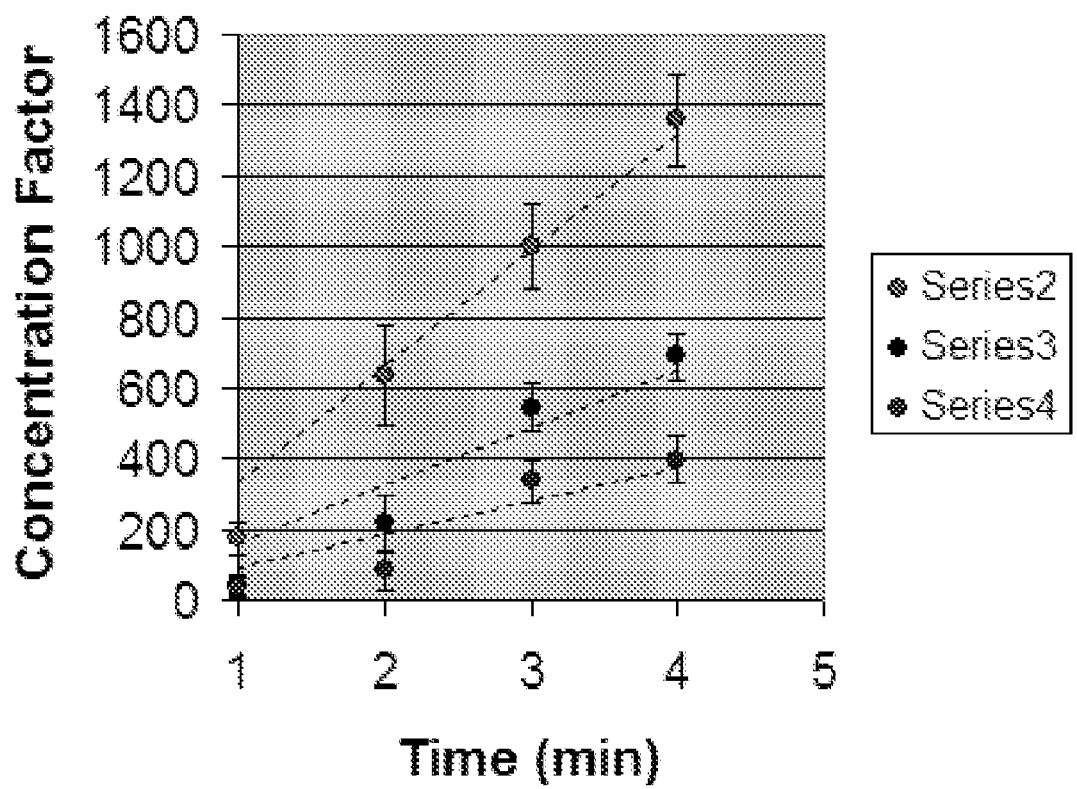
FIG. 18A shows several electropherograms depicting SDS-PAGE of a mixture of proteins. It is evident that without preconcentration, the proteins cannot be detected. As proteins are concentrated prior to separation, the peak height increases.
Figure 18B:
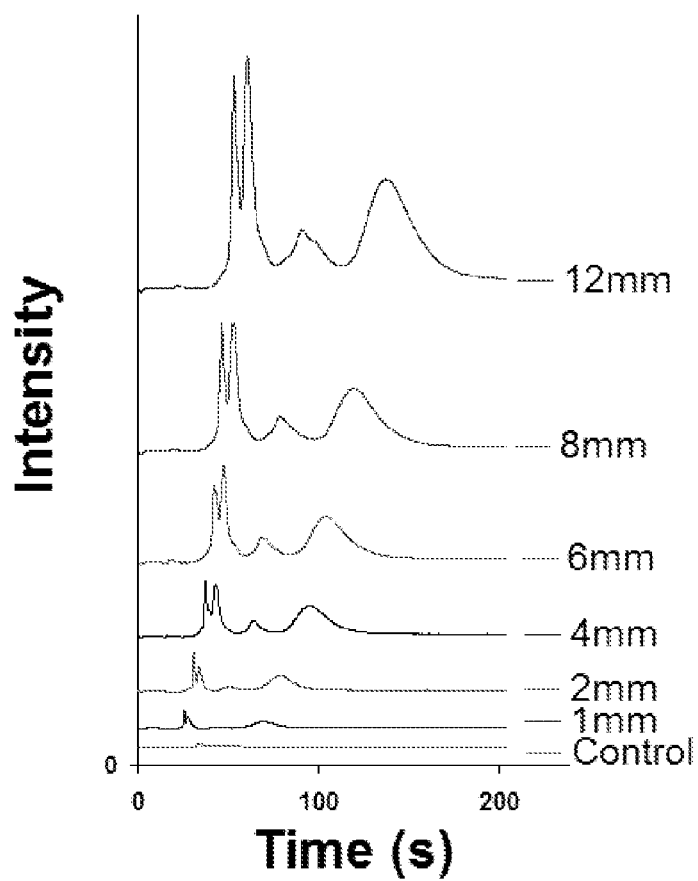
FIG. 18B shows the concentration factor obtained as a function of time of loading. Proteins could be concentrated up to 1400-fold upon 4 minutes of preconcentration (concentration was proportional to time and mobility of SDS-protein complex).

FIG. 18A shows electropherograms depicting SDS-PAGE of a mixture of proteins. It is evident that without preconcentration, the proteins cannot be detected. As proteins are concentrated prior to separation, the peak height increases. FIG. 18B shows the concentration factor obtained as a function of time of loading. Proteins could be concentrated up to 1400-fold upon 4 minutes of preconcentration. Concentration was proportional to time and mobility of SDS-protein complex.

Example 3

Preconcentration Followed by PAGE of DNA in a Microchip

Figure 15:
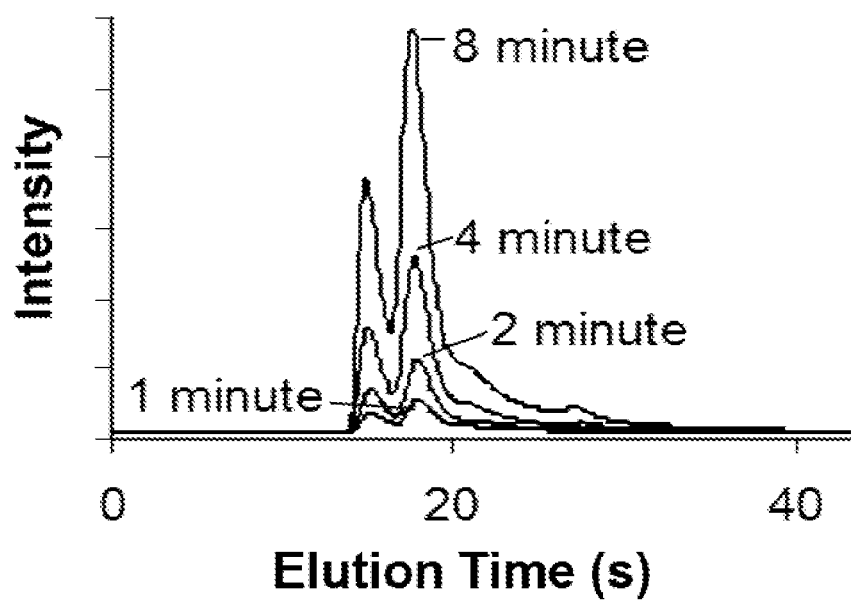
FIG. 15 shows electropherograms of 51 base double stranded DNA that was preconcentrated and analyzed with integrated PAGE. The preconcentration times ranged from about 1 to about 8 minutes with an applied field of 150 V/cm and the SEP element was 22% T 6% C crosslinked polyacrylamide/bisacrylamide. Separation in the PP element was with 8% T 5% C PAGE. The initial DNA concentration was 100 nM and the nucleic acid molecule was stained non-covalently with fluorescent dye (SYTO 64, Invitrogen, Carlsbad, Calif.). The electropherograms were captured by laser induced fluorescence.

Although there are many techniques for amplifying nucleic acid molecules, e.g., PCR, known in the art, there are instances where concentrating the nucleic acid molecules is preferred. Integrated preconcentration and analysis of nucleic acid molecules was achieved using a device and protocol similar to that described in Hatch et al. (2006) Anal. Chem. 78(14):4976-4984, which is herein incorporated by reference. However, as provided herein, the PP element was 8% T 5% C in order to separate smaller nucleic acid molecules. The SEP element dimensions and pore size was as previously described (22% T 6% T). The applied field for preconcentrating nucleic acid molecules was 150 V/cm for times ranging from about 1 to about 8 minutes and the field applied for separation was 300 V/cm. Nucleic acid molecules ranging from about 20 to greater than about 1,000 bp have been effectively preconcentrated and separated using these methods, including a commercially available 25 bp DNA ladder (Invitrogen, Carlsbad, Calif.). The nucleic acid molecules were labeled prior to preconcentration with intercalating dye such as Syto 64 (Invitrogen, Carlsbad, Calif.). FIG. 15 shows electropherograms depicting PAGE separations of Syto 64 labeled, 51 bp double stranded nucleic acid molecule, initially at 100 nM concentration. The electropherogram signal increased dramatically in proportion to preconcentration time.

Example 4

Preconcentration of Proteins as a Function of Volume Injected

Figure 19A:
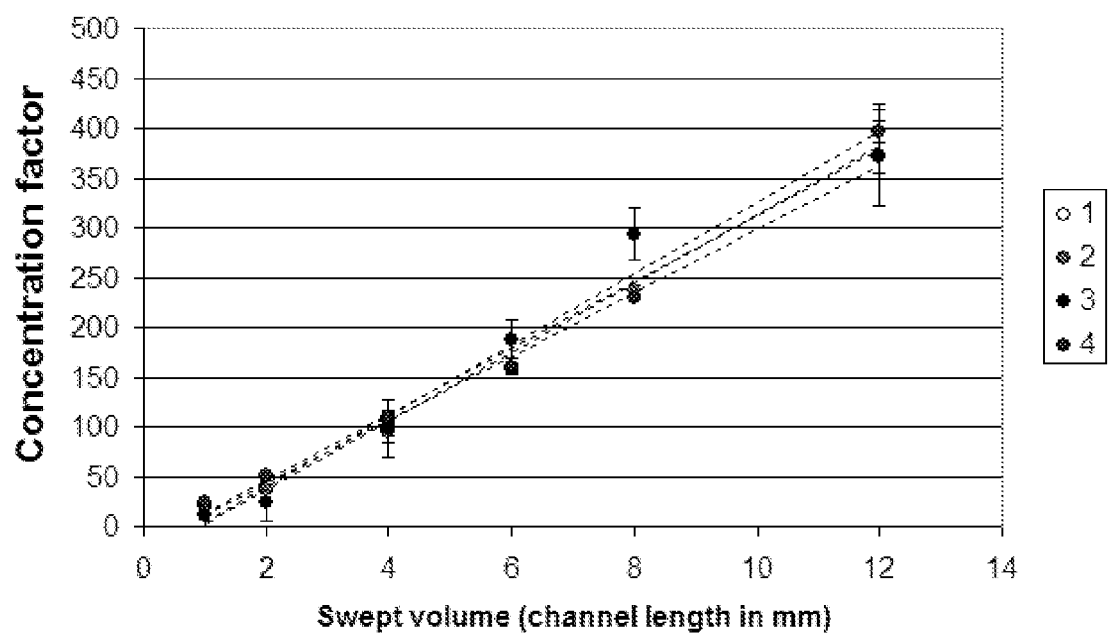
FIG. 19A shows the preconcentration of a protein as a function of volume injected showing that a concentration factor of over 350 can be obtained by using an injection channel 12 mm long as compared with a 1 mm-long channel. 1: parvalbumin, 12 kDa, 2: trypsin inhibitor, 20.1 kDa, 3: ovalbumin, 45 kDa, 4: bovine serum albumin, 66 kDa.
Figure 19B:
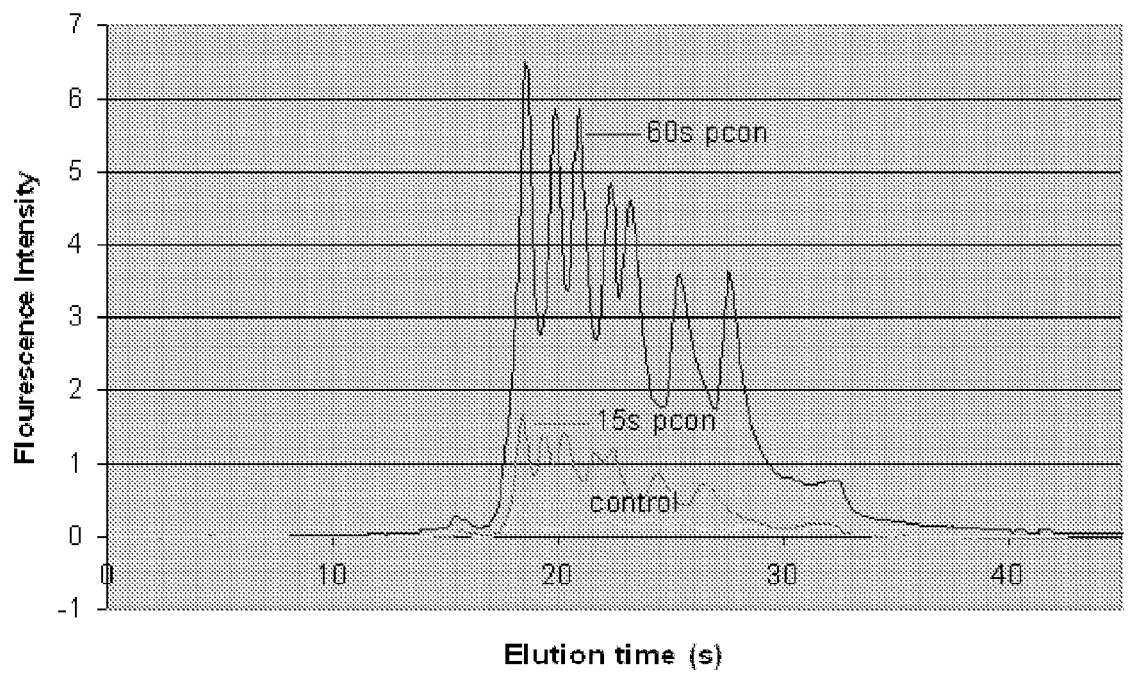
FIG. 19B shows the effect of increased pre-concentration of separation resolution.

In this implementation, a fixed volume defined by length of the injection channel is swept past the nanoporous membrane. FIG. 19A and FIG. 19B show preconcentration of a protein as a function of volume injected. A concentration factor of over 350 can be obtained by using an injection channel 12 mm long compared to a standard cross-T injection of sample (without preconcentration). See Hatch et al. (2006) Anal. Chem. 78(14):4976-4984, which is herein incorporated by reference. By sweeping a fixed channel volume to the SEP element, concentration factors of all excluded analyte is the same regardless of mobility. The concentration factors are also consistent from sample to sample and run to run because there is no dependence on ionic strength, concentration polarization, or conductivity.

Example 5

Integrated Preconcentration Followed by CGE (Capillary Gel Electrophoresis) Using Liquid Sieving Gel In this example, proteins are pre-concentrated on the SEP element prior to separation using a liquid sieving gel such as commercially-available Beckman 14-200 gel. The chip and experimental setup are the same as that described in Hatch et al. (2006) Anal. Chem. 78(14):4976-4984, which is herein incorporated by reference, except that the separation channel and loading channels are filled with the liquid sieving gel rather than a PP element. This example demonstrates that the SEP element is compatible with open channel separation methods such as gel electrophoresis and zone electrophoresis.

Example 6

Integrated Preconcentration and Electrophoretic Immunoassays

Immunoassays are one of the most widely used and sensitive techniques for detection and quantitation of analytes. Immunoassays are based on specific recognition and binding of a biological ligand to another molecule, the prominent example being binding of an antibody to an antigen. The generality of immunoassays stems from the fact that most of the analytes are either antigens or antibodies or are molecules against which an antibody can be generated by utilizing the immune system of a host animal. Typically either the antibody or the analyte, or in many cases a second antibody, is labeled with a signal-generating molecule such as an enzyme or fluorophore to tranduce the binding into a signal.

A typical immunoassay is performed using a solid surface to immobilize one of the components (antibody or antigen) with multiple subsequent incubations and washing steps to separate the bound from unbound species. However, conventional assay methods generally require long "incubation" periods (hours) and appreciable amounts of sample and reagents in order to obtain the desired response. Electrophoresis in microchannels has been demonstrated as an efficient means to separate an immune complex from free antibody or antigen. In such systems, an immune complex and an analyte are separated based upon differences in their charge-to-mass ratios. Specific advantages of microdevice-based separations relevant to electrophoretic-based immunoassays include the potential for shortened incubation times (as compared to solid-phase systems), simplified assay protocols as compared to the multiple wash and detection steps required for conventional immunodiagnostics such as ELISA, and device form-factors amenable to system integration and automation. Additionally, electrophoretic separation-based immunoassays eliminate the need to immobilize analytes on a solid surface, thus avoiding complexities associated with the solid-phase.

Figure 20A:
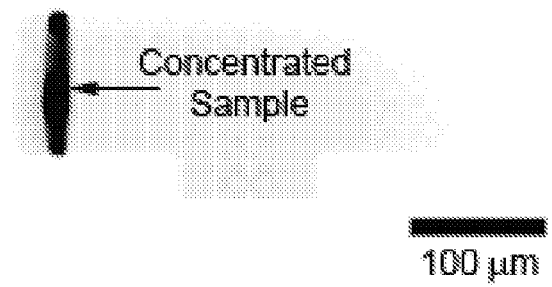
FIGS. 20A-20D show inverted fluorescence micrographs of preconcentration and elution of protein.
Figure 20B:
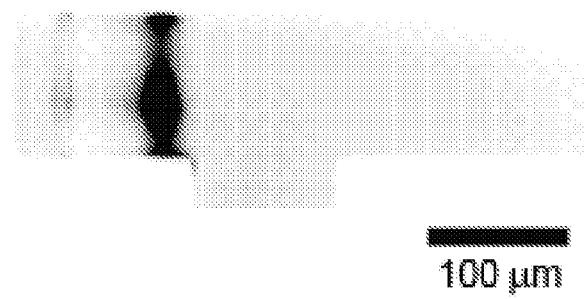
Figure 20C:
Figure 20D:
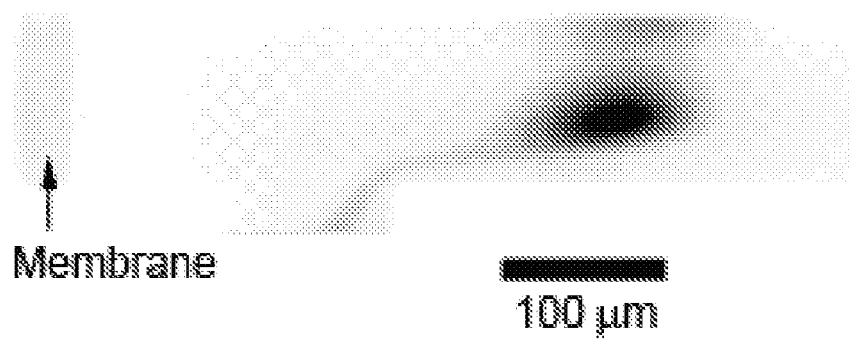
Figure 21A:
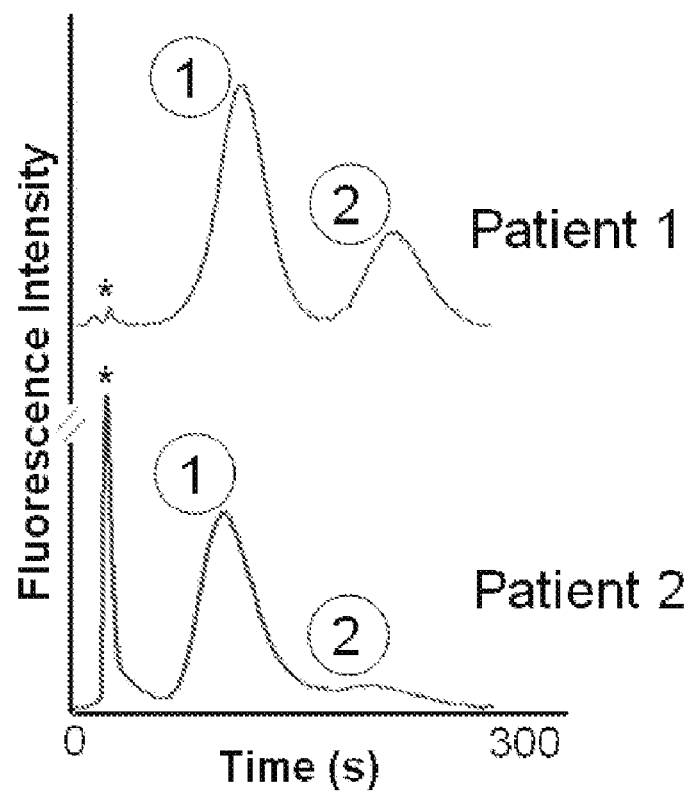
FIG. 21A show an "on-chip" IL-6 immunoassays of diseased saliva samples. Patient 1 exhibited higher levels of IL-6 evidenced by more immune complex (peak 2) than observed for patient 2. A significant fraction of reporter antibody (initially at 160 pM, peak 1) remains unbound. No complex has been observed with healthy samples.
Figure 21B:
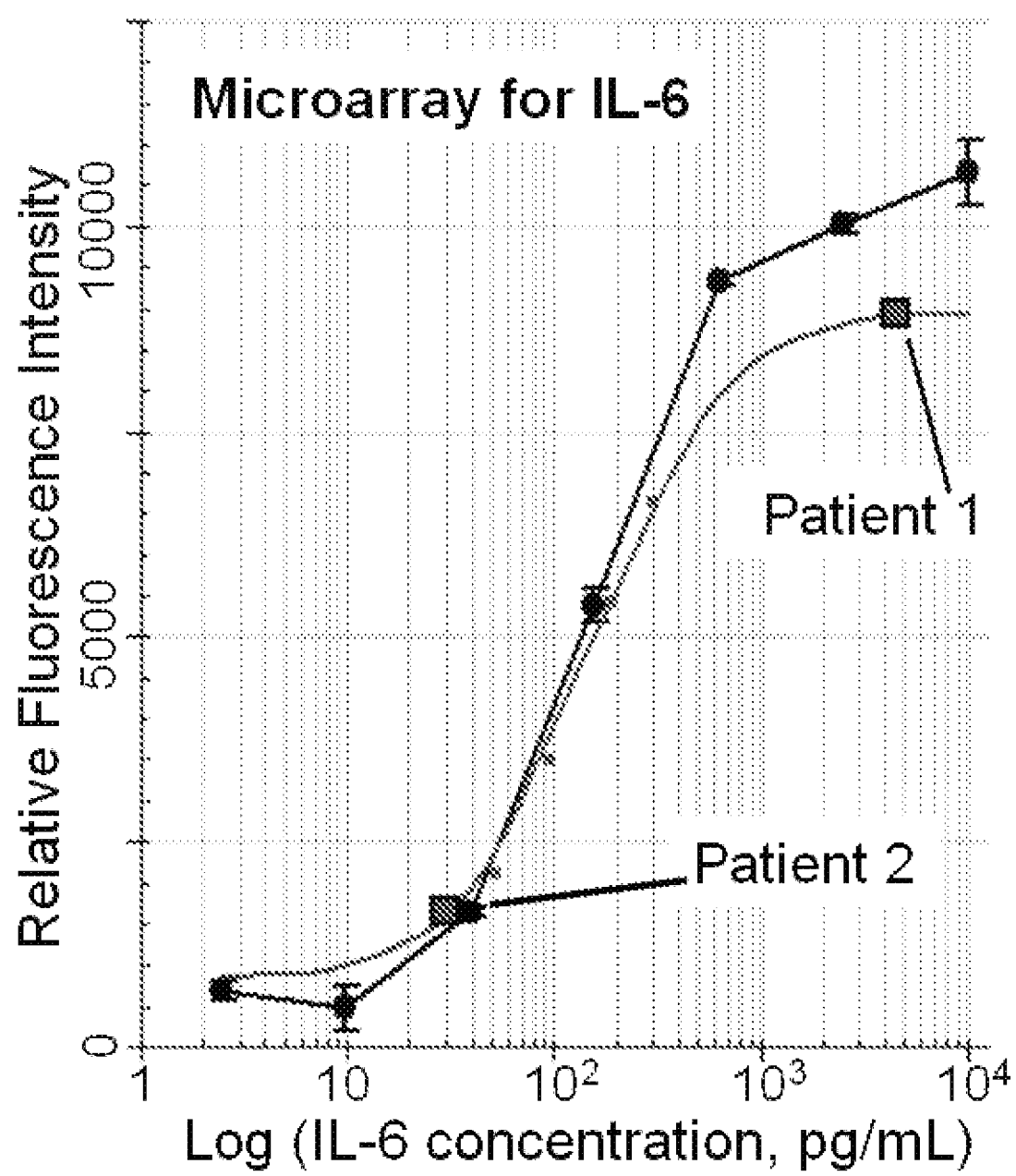
FIG. 21B shows a microarray immunoassays for benchmark comparison. Patient samples 1 and 2 (same as in FIG. 20A) are plotted on the calibration curve confirming higher IL-6 in patient 2 sample (Patient 1: 4600 pg/mL, 177 pM; Patient 2: 30 pg/mL, 1.2 pM).

Four disease biomarkers (IL-6, IL1$\beta$, TNF$\alpha$, and CRP) were detected in human saliva at concentrations (1-500 pM) undetectable without pre-concentration. The SEP element served to concentrate the biomarkers and, additionally, enabled rapid mixing of reporter molecules and sample—expediting sample preparation, conserving device real estate, and allowing integration of multiple processing steps. FIGS. 20A through 20D show separation of preconcentrated. Trapping of analytes in the small volume adjacent to the SEP element obviated the need for sample incubation and reporter binding steps, beyond the sample loading step (5 min.) (FIG. 20A). The concentrated reporter-sample mixture was eluted from the SEP element for subsequent PAGE immunoanalysis (FIG. 20B) where free antibody was separated from immune complex. The electropherograms shown in FIG. 21A demonstrate the rapid detection of IL-6 levels in diseased saliva samples. The PAGE immunoassay results compared well with gold-standard, sensitive protein microarray data (FIG. 21B)—with immunodetection of biomarkers at the sub-picoMolar level.

An immunoassay for the analyte C-reactive protein (CRP) upon concentration for 5 minutes was conducted (data not shown). Without the preconcentration, the detection limit is about 600 pM and with preconcentration it is about 40 pM, hence preconcentration leads to detection of CRP at 15-fold lower concentration.

The reported immunodiagnostic has demonstrated robust, yielding reproducible greater than about 100-fold concentration factors of protein biomarkers in unadulterated human saliva samples in less than about 5 minutes for detection of low-abundance protein biomarkers. Reagent mixing, preconcentration, and PAGE separations were seamlessly integrated on-chip in a portable format that holds promise for rapid point-of-care screening.

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

We claim:

1. A microfluidic device comprising
a microfluidic channel having
at least one in situ polymerized size-exclusion polymeric element having a first side and a second side, and
at least one porous polymeric element adjacent to the second side,
wherein the size-exclusion polymeric element has a length that is thinner than the length of the porous polymeric element,
a loading channel in fluidic communication with a portion of the microfluidic channel containing the porous polymeric element,
a sample reservoir in fluidic communication with a first waste reservoir, said sample reservoir is configured for containing a sample, wherein the sample reservoir and the first waste reservoir are configured to apply a first electric field from the sample reservoir through the loading channel and from the second side to the first side to the first waste reservoir, and
a first buffer reservoir and a second waste reservoir configured to apply a second electric field from the first buffer reservoir and from the second side to the second waste reservoir through the length of the porous polymeric element, wherein the second electric field bypasses the size-exclusion polymeric element.

2. The microfluidic device of claim 1, and further comprising a second size-exclusion polymeric element.

3. The microfluidic device of claim 2, wherein the size-exclusion polymeric element has pores that are larger than the pores of the second size-exclusion polymeric element.

4. The microfluidic device of claim 2, wherein the size-exclusion polymeric element has a cross-sectional area that is greater than the than the cross-sectional area of the second size-exclusion polymeric element.

5. The microfluidic device of claim 2, wherein the size-exclusion polymeric elements are arranged in series.

6. The microfluidic device of claim 1, wherein the size of the pores of the size-exclusion polymeric element are smaller than the size of an analyte of interest in the sample so as to prevent the analyte from passing through the size-exclusion polymeric element under application of the first electric field.

7. The microfluidic device of claim 1, wherein the length of the size-exclusion polymeric element is about 10 µm to about 50 µm.

8. The microfluidic device of claim 1, wherein the microfluidic device is configured to apply a third electric field from the first waste reservoir or a second buffer reservoir to the second waste reservoir and from the first side to the second side.

9. A method for processing an analyte in a sample in a microfluidic device comprising a microfluidic channel having at least one in situ polymerized size-exclusion polymeric element having a first side and a second side, and at least one porous polymeric element adjacent to the second side, wherein the size-exclusion polymeric element has a length that is thinner than the length of the porous polymeric element, a loading channel in fluidic communication with a portion of the microfluidic channel containing the porous polymeric element, a sample reservoir in fluidic communication with a first waste reservoir, said sample reservoir is configured for containing a sample, wherein the sample reservoir and the first waste reservoir are configured to apply a first electric field from the sample reservoir through the loading channel and from the second side to the first side to the first waste reservoir, and a first buffer reservoir and a second waste reservoir configured to apply a second electric field from the first buffer reservoir and from the second side to the second waste reservoir through the length of the porous polymeric element, wherein the second electric field bypasses the size-exclusion polymeric element, wherein the method comprises
concentrating the analyte on the second side of the size-exclusion polymeric element, and
moving the analyte through the porous polymeric element.

10. The method of claim 9, wherein the analyte is concentrated by applying the first electric field.

11. The method of claim 9, wherein the analyte is moved through the porous polymeric element by applying the second electric field.

12. The method of claim 9, which further comprises
eluting the analyte off the second side by applying the third electric field.

13. The method of claim 9, which further comprises
washing the analyte with a buffer solution applied at the second side under a mobilization field which moves the buffer solution from the second side to the first side.

14. The method of claim 13, wherein the direction of the mobilization field is from a wash reservoir, which may be the same or different from the first buffer reservoir, to a wash waste reservoir, which may be the same or different from the first waste reservoir.

15. The method of claim 9, which further comprises
adding a reagent to the analyte concentrated on the second side by concentrating the reagent on the second side with a mobilization field that crosses the size-exclusion polymeric element from the second side to the first side, wherein the mobilization field may be the same or different from the first electric field.

16. The method of claim 9, which further comprises
loading the sample from the loading channel into the porous polymeric element by applying a mobilization field that does not cross the size-exclusion polymeric element.

17. The method of claim 16, wherein the mobilization field is from the loading channel to the second waste reservoir.

18. The method of claim 9, which further comprises
loading the sample from the loading channel into the porous polymeric element by applying a mobilization field that crosses the size-exclusion polymeric element.

19. The method of claim 9, which further comprises
processing or assaying the analyte in the porous polymeric element by electrophoretic separation, chromatography, electrochromatography, immunochemistry, or a combination thereof.

20. The method of claim 19, wherein the electrophoretic separation is capillary zone electrophoresis, capillary gel electrophoresis, native PAGE, SDS-PAGE, or a combination thereof.

21. A method for processing an analyte in a sample in a microfluidic device comprising a microfluidic channel having at least one in situ polymerized size-exclusion polymeric element having a first side and a second side, and at least one porous polymeric element adjacent to the second side, wherein the size-exclusion polymeric element has a length that is thinner than the length of the porous polymeric element, a loading channel in fluidic communication with a portion of the microfluidic channel containing the porous polymeric element, a sample reservoir in fluidic communication with a first waste reservoir, said sample reservoir is configured for containing a sample, wherein the sample reservoir and the first waste reservoir are configured to apply a first electric field from the sample reservoir through the loading channel and from the second side to the first side to the first waste reservoir, and a first buffer reservoir and a second waste reservoir configured to apply a second electric field from the first buffer reservoir and from the second side to the second waste reservoir through the length of the porous polymeric element, wherein the second electric field bypasses the size-exclusion polymeric element, wherein the method comprises subjecting the sample to the microfluidic device to concentrate the analyte, filter the sample, exchange buffer, mix, react or bind the analyte with a reagent, or a combination thereof, and moving the sample or the analyte through the porous polymeric element.

\* \* \* \* \*